(12) United States Patent
Kumano

(10) Patent No.: US 10,753,951 B2
(45) Date of Patent: Aug. 25, 2020

(54) METHOD FOR DETERMINING BLOOD SPECIMEN

(71) Applicant: SYSMEX CORPORATION, Kobe-shi, Hyogo (JP)

(72) Inventor: Osamu Kumano, Hyogo (JP)

(73) Assignee: SYSMEX CORPORATION, Kobe-shi, Hyogo (JP)

(*) Notice: Subject to any disclaimer, the term of this patent is extended or adjusted under 35 U.S.C. 154(b) by 205 days.

(21) Appl. No.: 15/883,568

(22) Filed: Jan. 30, 2018

(65) Prior Publication Data

US 2018/0217169 A1 Aug. 2, 2018

(30) Foreign Application Priority Data

Jan. 31, 2017 (JP) .................................. 2017-016089

(51) Int. Cl.
*G01N 33/86* (2006.01)
*G01N 33/68* (2006.01)
(Continued)

(52) U.S. Cl.
CPC ............... *G01N 33/86* (2013.01); *C12Q 1/56* (2013.01); *G01N 33/4905* (2013.01);
(Continued)

(58) Field of Classification Search
CPC ...... G01N 33/86; G01N 33/683; G01N 33/92; G01N 2800/104; G01N 33/4905; C12Q 1/56
See application file for complete search history.

(56) References Cited

U.S. PATENT DOCUMENTS 8,557,592 B2 * 10/2013 Okuda ................. G01N 33/564
422/430
2003/0104493 A1 * 6/2003 Ortel ..................... G01N 21/77
435/7.9
(Continued)

FOREIGN PATENT DOCUMENTS

EP 1 469 317 A1 10/2004
EP 2 492 685 A1 8/2012
(Continued)

OTHER PUBLICATIONS

Jennings I, Mackie I, Arnout J, Preston FE on behalf of the UK National External Quality Assessment Scheme for Blood Coagulation. Lupus anticoagulant testing using plasma spiked with monoclonal antibodies: performance in the UK NEQAS proficiency testing programme. J Thromb Haemost 2004; 2: 2178-84. (Year: 2004).*

(Continued)

*Primary Examiner* — Benjamin R Whatley
*Assistant Examiner* — Jean Caraballo-Leon
(74) *Attorney, Agent, or Firm* — Sughrue Mion, PLLC

(57) ABSTRACT

Disclosed is a method for determining a blood specimen, comprising preparing a first measurement sample by mixing a blood specimen of a subject with a first coagulation time measurement reagent and measuring first coagulation time, preparing a second measurement sample by mixing the blood specimen with a second coagulation time measurement reagent and measuring second coagulation time, and acquiring a value based on the first coagulation time and the second coagulation time, wherein the second coagulation time measurement reagent contains a metal ion and/or normal plasma, and the value is used to determine whether the blood specimen of a subject is a blood specimen con- (Continued)

taining a lupus anticoagulant or a blood specimen containing a direct anticoagulant.

12 Claims, 44 Drawing Sheets

(51) Int. Cl.
*C12Q 1/56* (2006.01)
*G01N 33/92* (2006.01)
*G01N 33/49* (2006.01)

(52) U.S. Cl.
CPC ........... *G01N 33/683* (2013.01); *G01N 33/92* (2013.01); *G01N 2800/104* (2013.01)

(56) References Cited

U.S. PATENT DOCUMENTS

| | | | |
|---|---|---|---|
| 2004/0091952 A1 | 5/2004 | Okuda | |
| 2007/0026467 A1* | 2/2007 | Greenfield | G01N 33/564 435/7.21 |
| 2011/0159597 A1* | 6/2011 | Yoshida | C12Q 1/56 436/69 |
| 2014/0038205 A1* | 2/2014 | Raynard | C12Q 1/56 435/7.8 |
| 2014/0127725 A1* | 5/2014 | Ieko | G01N 33/86 435/13 |
| 2014/0127726 A1* | 5/2014 | Ieko | C12Q 1/56 435/13 |
| 2014/0295470 A1* | 10/2014 | Okuda | G01N 33/86 435/13 |

FOREIGN PATENT DOCUMENTS

| | | |
|---|---|---|
| EP | 2 423 687 B1 | 5/2016 |
| EP | 3 076 173 A1 | 10/2016 |

OTHER PUBLICATIONS

Lindhoff-Last E, Humpich M, Schmitt J, Rodiger S, Seifried E, Bauersachs R (2002) MIXCON-LA: a precise, sensitive and specific aPTT-based assay for detection of lupus anticoagulant. Clin Appl Thromb Hemost 8:163-167 (Year: 2002).*

Moore GW. Current controversies in lupus anticoagulant detection. Antibodies. 2016;5(4):22. (Year: 2016).*

Communication pursuant to Article 94(3) EPC dated Jun. 11, 2019 in a counterpart European patent application No. 18153181.5.

Rosner et al., "Detection and Quantitative Evaluation of Lupus Circulating Anticoagulant Activity", Thrombosis and Haemostasis, Schattauer Verlag GmbH, Germany, vol. 57, No. 2, Jan. 1, 1987, pp. 144-147, XP008024540 (4 pages total).

Communication, dated Feb. 12, 2020, issued by European Patent Office in European Application No. 18 153 181.5.

* cited by examiner

FIG. 10

JOB LIST (DATE DESIGNATION-227/10000)

| | MENU | REAGENT INFORMATION | CALIBRATION CURVE | QC CHART | ORDER | | JOB LIST | | CONDITION DISPLAY | MAINTENANCE | | SHUTDOWN | | STAT | | INTERRUPTION | START |
|---|---|---|---|---|---|---|---|---|---|---|---|---|---|---|---|---|---|

| | | | | | | | | | | | EXPORT |
| | | | | | | | | | | | CUSTOMIZE |
| | | | | | | | | | | | SPECIMEN INTEGRATION |

| ∨ | Dt | CONDITION | RACK NUMBER-POSITION | SPECIMEN NUMBER | START TIME | END TIME sec | APTT sec | APTT sec | TC APTT sec | LA1 1-1 sec | LA2 1-1 sec |
|---|---|---|---|---|---|---|---|---|---|---|---|
| | | | 000025-08 | RCaiL 501-1 Mn | 21:22 | 21:33 | | | | 51.0 | 45.7 |
| | | | 000025-09 | RCaiL 501-1 Cu | 21:23 | 21:33 | | | | 40.3 | 36.4 |
| | | | 000026-01 | RCaiL 502-2 Bla | 21:24 | 21:34 | | | | 61.3 | 47.1 |
| | | | 000026-02 | RCaiL 502-2 Mix | 21:24 | 21:35 | | | | 46.0 | 39.0 |
| | | | 000026-03 | RCaiL 502-2 Ni | 21:25 | 21:35 | | | | 63.5 | 47.4 |
| | | | 000026-04 | RCaiL 502-2 Co | 21:25 | 21:36 | | | | 97.2 | 54.8 |
| | | | 000026-05 | RCaiL 502-2 Zn | 21:26 | 21:36 | | | | 89.0 | 56.3 |
| | | | 000026-06 | RCaiL 502-2 Al | 21:27 | 21:37 | | | | 60.9 | 46.6 |
| | | | 000026-07 | RCaiL 502-2 Fe | 21:27 | 21:38 | | | | 62.0 | 47.1 |
| | | | 000026-08 | RCaiL 502-2 Mn | 21:28 | 21:38 | | | | 89.1 | 62.9 |
| | | | 000026-09 | RCaiL 502-2 Cu | 21:28 | 21:39 | | | | 63.8 | 47.6 |
| | | | 000027-01 | RCaiL 502-3 Cu | 21:30 | 21:40 | | | | 79.5 | 55.5 |
| | | | 000027-02 | RCaiL 502-3 Mix | 21:30 | 21:41 | | | | 53.9 | 43.5 |
| | | | 000027-03 | RCaiL 502-3 Ni | 21:31 | 21:41 | | | | 84.4 | 55.6 |
| | | | 000027-04 | RCaiL 502-3 Co | 21:31 | 21:42 | | | | 131.0 | 65.5 |
| | | | 000027-05 | RCaiL 502-3 Zn | 21:32 | 21:42 | | | | 116.5 | 67.7 |
| | | | 000027-06 | RCaiL 502-3 Al | 21:33 | 21:43 | | | | 77.4 | 54.1 |
| | | | 000027-07 | RCaiL 502-3 Fe | 21:33 | 21:44 | | | | 78.7 | 55.0 |
| | | | 000027-08 | RCaiL 502-3 Mn | 21:34 | 21:44 | | | | 115.2 | 45.7 |
| | | | 000027-09 | RCaiL 502-3 Bla | 21:34 | 21:45 | | | | 82.8 | 56.0 |

CS-5100 OFF

OTHERS (3/3)

CLOSE

8:37

METHOD FOR DETERMINING BLOOD SPECIMEN

CROSS REFERENCE TO RELATED APPLICATIONS

This application claims priority from prior Japanese Patent Application No. 2017-016089, filed on Jan. 31, 2017, entitled "Method for determining blood specimen, apparatus and computer program for analysis of blood specimen", the entire contents of which are incorporated herein by reference.

TECHNICAL FIELD

The present invention relates to a method for determining a blood specimen. The present invention also relates to an apparatus and a computer program for analysis of a blood specimen.

BACKGROUND

A lupus anticoagulant (LA) is an autoantibody that inhibits a phospholipid-dependent coagulation reaction. LA is detected in a patient with antiphospholipid antibody syndrome that exhibits thrombosis and pregnancy complications. Since LA inhibits phospholipids required for a phospholipid-dependent coagulation reaction, coagulation time is prolonged in the blood of an LA-positive patient. On the other hand, coagulation time is prolonged even in the blood of a patient who received an anticoagulant such as warfarin. Therefore, in order to accurately detect a blood specimen of an LA-positive patient, it is necessary to discriminate a blood specimen containing LA and a blood specimen containing an anticoagulant. However, it is difficult to distinguish between the two in a normal coagulation test.

In the case where the subject is suspected of being LA positive, a mixing test is performed as a test of LA. In the mixing test, plasma of a subject and normal plasma are mixed, and the coagulation time of the obtained mixed plasma is measured. When the subject is an LA-positive patient, prolongation of coagulation time is not improved even when a mixing test is performed. Furthermore, an index for quantitatively evaluating the result of the mixing test such as ICA (Index of Circulating Anticoagulant) or LR (Lupus Ratio) value is calculated from the coagulation time of the plasma of a subject, normal plasma and mixed plasma, and a method of detecting LA based on this index is also known. Also, in the confirmatory test of LA, it is confirmed whether prolongation of coagulation time depends on phospholipid. Specifically, the coagulation time is measured using two kinds of coagulation time measurement reagents having different concentrations of phospholipids, and based on the ratio of the coagulation time obtained from each reagent, prolongation of the coagulation time dependent on the phospholipid concentration is confirmed to detect a specimen containing LA. For example, US 2004/091952 describes that a specimen containing LA and a specimen containing warfarin could be discriminated by combining a mixing test and a phospholipid dependent confirmatory test. Specifically, the coagulation times of mixed plasma and normal plasma were measured using two kinds of coagulation time measurement reagents having different concentrations of phospholipids, and the LR values calculated from these coagulation times were used to discriminate plasma of LA-positive patients and plasma of patients who received warfarin.

Conventionally, warfarin is often used as an anticoagulant. Warfarin, also called vitamin K antagonist, inhibits vitamin K necessary for the production of coagulation factors, thereby suppressing the formation of coagulation factors in the liver and exhibiting an anticoagulation effect. In recent years, novel anticoagulants with an action mechanism different from warfarin are also used. Such an anticoagulant exhibits an action of binding to a coagulation factor and directly inhibiting the coagulation reaction mediated by the coagulation factor. Hereinafter, the anticoagulant having an action of directly inhibiting a coagulation reaction is also referred to as "direct anticoagulant" or "DAC". Coagulation time is prolonged even in the blood of a patient who received DAC. When the blood specimen of the subject who received DAC was determined to be a specimen containing LA by mistake, excessive anticoagulation therapy may be given to the subject. Excessive anticoagulation therapy increases the risk of bleeding. Therefore, discrimination between blood specimens containing LA and blood specimens containing DAC is clinically important. However, it has been difficult to make such discrimination by conventional methods. Therefore, it is desirable to develop means capable of discriminating a blood specimen containing LA and a blood specimen containing DAC.

SUMMARY OF THE INVENTION

Accordingly, a first aspect provides a method for determining a blood specimen. This method includes preparing a first measurement sample by mixing a blood specimen of a subject with a first coagulation time measurement reagent and measuring first coagulation time; preparing a second measurement sample by mixing the blood specimen with a second coagulation time measurement reagent and measuring second coagulation time; and acquiring a value based on the first coagulation time and the second coagulation time. In this method, the second coagulation time measurement reagent contains a metal ion and/or normal plasma. The above value is used to determine whether the blood specimen of a subject is a blood specimen containing LA or a blood specimen containing DAC.

BRIEF DESCRIPTION OF THE DRAWINGS

FIG. 10 is a view showing an example of a screen for displaying a measurement result by the blood specimen analyzer.

DETAILED DESCRIPTION OF THE PREFERRED EMBODIMENTS

Figure 1:
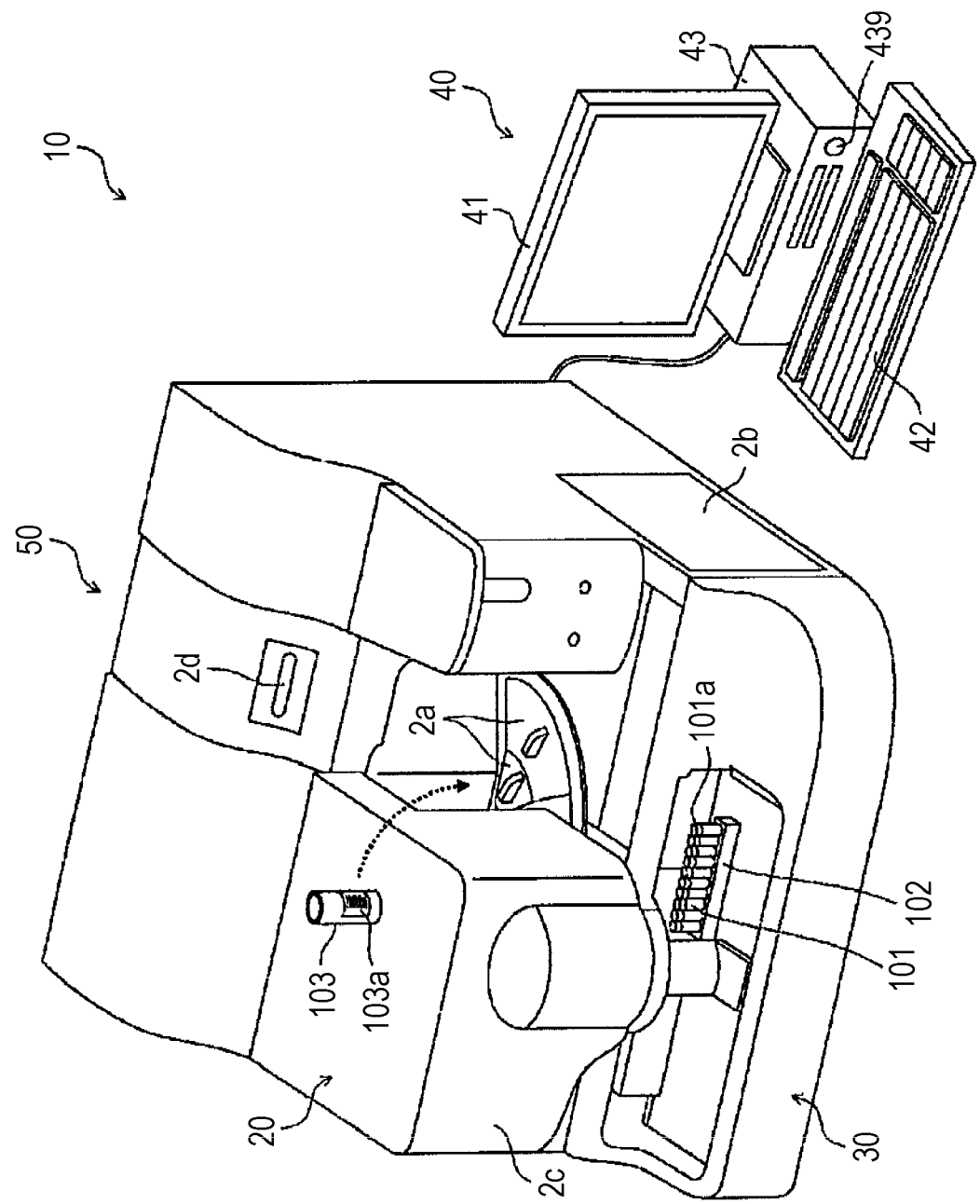
FIG. 1 is a perspective view showing the configuration of an appearance of a blood specimen analyzer.

Accordingly, a first aspect provides a method for determining a blood specimen. This method includes preparing a first measurement sample by mixing a blood specimen of a subject with a first coagulation time measurement reagent and measuring first coagulation time; preparing a second measurement sample by mixing the blood specimen with a second coagulation time measurement reagent and measuring second coagulation time; and acquiring a value based on the first coagulation time and the second coagulation time. In this method, the second coagulation time measurement reagent contains a metal ion and/or normal plasma. The above value is used to determine whether the blood specimen of a subject is a blood specimen containing LA or a blood specimen containing DAC.

A second aspect provides a method for determining a blood specimen using plural kinds of coagulation time measurement reagents with different phospholipid concentrations. This method includes preparing a first measurement sample by mixing a blood specimen of a subject with a first coagulation time measurement reagent and measuring first coagulation time; preparing a second measurement sample by mixing the blood specimen with a second coagulation time measurement reagent and measuring second coagulation time; preparing a third measurement sample by mixing the blood specimen with a third coagulation time measurement reagent and measuring third coagulation time; preparing a fourth measurement sample by mixing the blood specimen with fourth coagulation time measurement reagent and measuring a fourth coagulation time; and acquiring the value of the index calculated by equation (4) or (5) described later. In this method, the second coagulation time measurement reagent contains a metal ion and/or normal plasma. The third coagulation time measurement reagent contains phospholipids at a concentration higher than that of the first coagulation time measurement reagent. The fourth coagulation time measurement reagent contains a metal ion and/or normal plasma and also contains phospholipid at a concentration higher than that of the second coagulation time measurement reagent.

A third aspect provides a method for determining a blood specimen using two kinds of coagulation time measurement reagents having different phospholipid concentrations and also containing a metal ion and/or normal plasma. This method includes preparing a first measurement sample by mixing a blood specimen of a subject with a first coagulation time measurement reagent and measuring first coagulation time; preparing a second measurement sample by mixing the blood specimen with a second coagulation time measurement reagent and measuring second coagulation time; and acquiring a value based on the first coagulation time and the second coagulation time. In this method, the first coagulation time measurement reagent contains a coagulation time measurement reagent containing phospholipids and a preparation reagent containing a metal ion and/or normal plasma. The second coagulation time measurement reagent contains a coagulation time measurement reagent containing phospholipids at a concentration higher than that of the first coagulation time measurement reagent and a preparation reagent containing a metal ion and/or normal plasma. The above value is used to determine whether the blood specimen of a subject is a blood specimen containing LA or a blood specimen containing DAC.

A fourth aspect provides a blood specimen analyzer. This apparatus comprises a measurement sample preparing section for preparing a measurement sample, an optical information acquiring section for irradiating the prepared measurement sample with light and acquiring optical information on the light amount from the measurement sample, a control unit, an input unit, and a display unit. The measurement specimen preparing section of this apparatus prepares a first measurement sample by mixing a blood specimen of a subject with a first coagulation time measurement reagent, and prepares a second measurement sample by mixing the blood specimen with a second coagulation time measurement reagent. The optical information acquiring section acquires first optical information from the first measurement sample, and acquires second optical information from the second measurement sample. The control unit acquires first coagulation time based on the first optical information and acquires second coagulation time based on the second optical information, and acquires a value based on the first coagulation time and the second coagulation time. Here, the second coagulation time measurement reagent is a coagulation time measurement reagent containing a metal ion and/or normal plasma. The above value is used to determine whether the blood specimen of a subject is a blood specimen containing LA or a blood specimen containing DAC.

A fifth aspect provides a blood specimen analyzer using plural kinds of coagulation time measurement reagents with different phospholipid concentrations. This apparatus comprises a measurement sample preparing section for preparing a measurement sample, an optical information acquiring section for irradiating the prepared measurement sample with light and acquiring optical information on the light amount from the measurement sample, a control unit, an input unit, and a display unit. The measurement specimen preparing section of this apparatus prepares a first measurement sample by mixing a blood specimen of a subject with a first coagulation time measurement reagent, prepares a second measurement sample by mixing the blood specimen with a second coagulation time measurement reagent, prepares a third measurement sample by mixing the blood specimen of a subject with a third coagulation time measurement reagent, and prepares a fourth measurement sample by mixing the blood specimen with a fourth coagulation time measurement reagent. The optical information acquiring section acquires first optical information from the first measurement sample, acquires second optical information from the second measurement sample, acquires third optical information from the third measurement sample, and acquires fourth optical information from the fourth measurement sample. The control unit acquires first coagulation time based on the first optical information, acquires second coagulation time based on the second optical information, acquires third coagulation time based on the third optical information and acquires fourth coagulation time based on the fourth optical information, and acquires the value of the index calculated by equation (4) or (5) described later. Here, the second coagulation time measurement reagent is a coagulation time measurement reagent containing a metal ion and/or normal plasma. The third coagulation time measurement reagent is a coagulation time measurement reagent containing phospholipids at a concentration higher than that of the first coagulation time measurement reagent. The fourth coagulation time measurement reagent is a coagulation time measurement reagent containing a metal ion and/or normal plasma and also containing phospholipids at a concentration higher than that of the second coagulation time measurement reagent.

A sixth aspect provides a blood specimen analyzer using two kinds of coagulation time measurement reagents having different phospholipid concentrations and also containing a metal ion and/or normal plasma. This apparatus comprises a measurement sample preparing section for preparing a measurement sample, an optical information acquiring section for irradiating the prepared measurement sample with light and acquiring optical information on the light amount from the measurement sample, a control unit, an input unit, and a display unit. The measurement specimen preparing section of this apparatus prepares a first measurement sample by mixing a blood specimen of a subject with a first coagulation time measurement reagent, and prepares a second measurement sample by mixing the blood specimen with a second coagulation time measurement reagent. The optical information acquiring section acquires first optical information from the first measurement sample, and acquires second optical information from the second measurement sample. The control unit acquires first coagulation time based on the first optical information and acquires second coagulation time based on the second optical information, and acquires a value based on the first coagulation time and the second coagulation time. Here, the first coagulation time measurement reagent is a coagulation time measurement reagent containing a coagulation time measurement reagent containing phospholipids and a preparation reagent containing a metal ion and/or normal plasma. The second coagulation time measurement reagent is a coagulation time measurement reagent containing a coagulation time measurement reagent containing phospholipids at a concentration higher than that of the first coagulation time measurement reagent and a preparation reagent containing a metal ion and/or normal plasma. The above value is used to determine whether the blood specimen of a subject is a blood specimen containing LA or a blood specimen containing DAC.

A seventh aspect provides a computer program for analysis of a blood specimen, which is recorded on a computer readable medium. This computer program makes a computer execute the steps of: acquiring first optical information from a first measurement sample containing a blood specimen of a subject and a first coagulation time measurement reagent, and acquiring second optical information from a second measurement sample containing the blood specimen and a second coagulation time measurement reagent; acquiring first coagulation time based on the first optical information and acquiring second coagulation time based on the second optical information; and acquiring a value based on the first coagulation time and the second coagulation time. Here, the second coagulation time measurement reagent is a coagulation time measurement reagent containing a metal ion and/or normal plasma. The above value is used to determine whether the blood specimen of a subject is a blood specimen containing LA or a blood specimen containing DAC.

An eighth aspect provides a computer program for analysis of a blood specimen, which is recorded on a computer readable medium. This computer program makes a computer execute the steps of: acquiring first optical information from a first measurement sample containing a blood specimen of a subject and a first coagulation time measurement reagent, acquiring second optical information from a second measurement sample containing the blood specimen and a second coagulation time measurement reagent, acquiring third optical information from a third measurement sample containing the blood specimen and a third coagulation time measurement reagent, and acquiring fourth optical information from a fourth measurement sample containing the blood specimen and a fourth coagulation time measurement reagent; acquiring first coagulation time based on the first optical information, acquiring second coagulation time based on the second optical information, acquiring third coagulation time based on the third optical information, and acquiring fourth coagulation time based on the fourth optical information; and acquiring the value of the index calculated by equation (4) or (5) described later. Here, the second coagulation time measurement reagent is a coagulation time measurement reagent containing a metal ion and/or normal plasma. The third coagulation time measurement reagent is a coagulation time measurement reagent containing phospholipids at a concentration higher than that of the first coagulation time measurement reagent. The fourth coagulation time measurement reagent is a coagulation time measurement reagent containing a metal ion and/or normal plasma and also containing phospholipids at a concentration higher than that of the second coagulation time measurement reagent.

A ninth aspect provides a computer program for analysis of a blood specimen, which is recorded on a computer readable medium. This computer program makes a computer execute the steps of: acquiring first optical information from a first measurement sample containing a blood specimen of a subject and a first coagulation time measurement reagent and acquiring second optical information from a second measurement sample containing the blood specimen and a second coagulation time measurement reagent; acquiring first coagulation time based on the first optical information and acquiring second coagulation time based on the second optical information; and acquiring a value based on the first coagulation time and the second coagulation time. Here, the first coagulation time measurement reagent is a coagulation time measurement reagent containing a coagulation time measurement reagent containing phospholipids and a preparation reagent containing a metal ion and/or normal plasma. The second coagulation time measurement reagent is a coagulation time measurement reagent containing a coagulation time measurement reagent containing phospholipids at a concentration higher than that of the first coagulation time measurement reagent and a preparation reagent containing a metal ion and/or normal plasma. The above value is used to determine whether the blood specimen of a subject is a blood specimen containing LA or a blood specimen containing DAC.

According to the present invention, it is possible to quantitatively determine on whether a blood specimen of a subject is a blood specimen containing LA (hereinafter also referred to as "LA specimen") or a blood specimen containing DAC (hereinafter also referred to as "DAC specimen").

[1. Method for Determining Blood Specimen]

The method for determining a blood specimen of this embodiment (hereinafter also simply referred to as "method") is a method of discriminating an LA specimen and a DAC specimen. As described above, a direct anticoagulant (DAC) refers to an agent that binds to a coagulation factor and directly inhibits the coagulation reaction mediated by the coagulation factor. The direct anticoagulant that can be administered orally is called DOAC (direct oral anticoagulant). As DAC, factor Xa inhibitors and thrombin inhibitors are known in the art. The factor Xa inhibitor can bind directly to factor Xa and inhibits the conversion of prothrombin to thrombin. Examples of the factor Xa inhibitor include rivaroxaban, apixaban, edoxaban, betrixaban, otamixaban, razaxaban, darexaban, letaxaban, eribaxaban, antistasin, and the like. The thrombin inhibitor can bind directly to thrombin and inhibits thrombin-mediated fibrinogen activation. Examples of the thrombin inhibitor include dabigatran, bivalirudin, hirudin, lepirudin, desirudin, argatroban, melagatran, ximelagatran, and the like.

In the method of this embodiment, a first measurement sample is prepared by mixing a blood specimen of a subject with a first coagulation time measurement reagent, and first coagulation time is measured. The first coagulation time corresponds to the coagulation time of a blood specimen of a subject measured by a general coagulation test.

The blood specimen of a subject may be blood (whole blood) collected from the subject or plasma prepared from the blood. Among them, plasma is preferable, and platelet-removed plasma is more preferable. The platelets can be removed by a known method such as centrifugation or filter separation. In this embodiment, the blood specimen of a subject is preferably a blood specimen suspected of containing LA. Examples of such a blood specimen include blood specimens in which coagulation time is found to be prolonged by an ordinary coagulation test, blood specimens obtained from a thrombosis patient or a person suspected of having thrombosis, and the like.

The first coagulation time measurement reagent may be a reagent for measuring coagulation time based on the measurement principle known in the art. Examples thereof include reagents for measuring at least one kind of dilute Russell viper venom coagulation time (dRVVT), activated partial thromboplastin time (APTT), dilute activated partial thromboplastin time (dAPTT), kaolin coagulation time (KCT), prothrombin time (PT), dilute prothrombin time (dPT), thrombin time (TT), and dilute thrombin time (dTT). Among them, a dRVVT measuring reagent, an APTT measuring reagent and a dAPTT measuring reagent are preferable. Commercially available coagulation time measurement reagents and reagent kits may be used.

The first coagulation time measurement reagent contains a component necessary for coagulation according to the type of the coagulation time to be measured. The component necessary for coagulation herein refers to a component necessary for causing blood coagulation in vitro. Such component is known in the art, and examples thereof include activators, snake venom, tissue factors, and the like. As the activator, a contact factor activator is preferable, and examples thereof include ellagic acid, kaolin, celite, silica, and the like. The ellagic acid may be an ellagic acid in a state of forming a chelate with a metal ion. Examples of the snake venom include Russell viper venom, Textarin snake venom, and Ecarin snake venom. Examples of the tissue factor include tissue factors derived from rabbit brain or human placenta, recombinant tissue factors, and the like.

The first coagulation time measurement reagent may contain phospholipid to promote blood coagulation. Examples of the phospholipid include phosphatidylethanolamine (PE), phosphatidylcholine (PC) and phosphatidylserine (PS). The first coagulation time measurement reagent contains one kind, preferably two kinds, and more preferably all kinds of phospholipids selected from PE, PC and PS. The phospholipid may be a naturally occurring phospholipid or a synthetic phospholipid. From the viewpoint of improving the sensitivity to LA, synthetic phospholipids or naturally occurring phospholipids purified to a purity of 99% or more are preferable. The fatty acid side chains of PE, PC and PS are not particularly limited, and examples thereof include palmitic acid, oleic acid, stearic acid, and the like. Among them, oleic acid is preferable.

The concentration of phospholipids in the first coagulation time measurement reagent can be appropriately determined according to the type of the coagulation time to be measured. For example, in the case where the first coagulation time measurement reagent is a dRVVT or dAPTT measurement reagent and the blood specimen and the reagent are mixed in a volume ratio of 1:1, the concentration of phospholipids in the reagent is usually 20 to 150 µg/mL, and preferably 30 to 70 µg/mL. In the case where the first coagulation time measurement reagent is an APTT measurement reagent and the blood specimen and the reagent are mixed in a volume ratio of 1:1, the concentration of phospholipids in the reagent is usually 150 to 2000 µg/mL, and preferably 150 to 600 µg/mL. In the case where the mixing ratio of the blood specimen and the first coagulation time measurement reagent is not 1:1, the concentration of phospholipids in the reagent may be appropriately adjusted according to the mixing ratio.

In the case where the first coagulation time measurement reagent contains kaolin as an activating agent and is a reagent based on the principle of KCT measurement, the reagent may not contain phospholipid. In the KCT measurement, the endogenous phospholipid contained in the blood specimen is used for coagulation reaction.

The first coagulation time measurement reagent may contain calcium ions, in order to initiate blood coagulation. In this case, the first coagulation time measurement reagent may be a one-liquid type reagent containing a component necessary for coagulation and calcium ions, or a component necessary for coagulation, phospholipids and calcium ions. Alternatively, the first coagulation time measurement reagent may be a two-liquid type reagent comprising a first partial reagent containing a component necessary for coagulation or containing the component and phospholipids, and a second partial reagent containing calcium ions.

It is preferable that calcium ions are supplied into the first coagulation time measurement reagent with a calcium salt or an aqueous solution thereof. Examples of the calcium salt include calcium chloride and the like. The content of calcium ions in the first coagulation time measurement reagent may be an amount sufficient to cause coagulation, and is, for example, usually 2 mmol/L or more and 40 mmol/L or less, and preferably 4 mmol/L or more and 30 mmol/L or less, in terms of calcium chloride concentration. In the case where the first coagulation time measurement reagent is a two-liquid type reagent, the second partial reagent containing calcium ions is preferably an aqueous solution of a calcium salt. Herein, "mmol/L" is also expressed as "mM".

In the case where the first coagulation time measurement reagent contains Russell viper venom as a component necessary for coagulation and is a reagent based on the principle of dRVVT measurement, the reagent may not contain calcium ions. Russell viper venom directly activates coagulation factor X to cause blood coagulation.

The first measurement sample is prepared by mixing the blood specimen with the first coagulation time measurement reagent. The reaction condition of the blood specimen and the first coagulation time measurement reagent can be appropriately determined according to the kind of the reagent. In the case where the first coagulation time measurement reagent is a two-liquid type reagent, the reaction time of the blood specimen with the first partial reagent is usually from 1 minute or more and 10 minutes or less, and preferably from 3 minutes or more and 5 minutes or less. The temperature condition is usually 25° C. or more and 45° C. or less, and preferably 35° C. or more and 38° C. or less. The preparation of the measurement sample may be carried out by a manual method or may be carried out by a fully automatic measurement device. Examples of the device include CS-5100 (Sysmex Corporation), CS-2400 (Sysmex Corporation), CS-2000i (Sysmex Corporation), and the like.

Measurement of first coagulation time is carried out promptly after preparation of the first measurement sample. Specifically, in the case where the first coagulation time measurement reagent is a two-liquid type reagent, measurement of first coagulation time is started, from the time when the second partial reagent containing calcium ions is added to the mixture of the blood specimen and the first partial reagent. In the case where the first coagulation time measurement reagent is a one-liquid type reagent containing calcium ions or snake venom, measurement of first coagulation time is started from the time when the reagent is added to the blood specimen.

Measurement of first coagulation time may be carried out by a manual method or may be carried out by the above fully automated coagulation time measurement device. Preferably, measurement is carried out by a fully automated coagulation time measurement device. In the case where the coagulation time is measured by this device, the measurement sample is irradiated with light, and the coagulation time is calculated based on the obtained optical information. The light to be irradiated may be light which is usually used for measuring coagulation time, and is, for example, light having a wavelength of around 660 nm. A light source is not particularly limited, and examples thereof include a light emitting diode, a halogen lamp, and the like. By irradiating the measurement sample with light from the light source, scattered light and transmitted light are generated from the measurement sample. In this embodiment, examples of the optical information on the light amount include the amount of scattered light or the amount of transmitted light, and scattered light intensity, transmittance, absorbance and the like are preferable.

In the method of this embodiment, a second measurement sample is prepared by mixing a blood specimen of a subject with a second coagulation time measurement reagent, and second coagulation time is measured. The second coagulation time is coagulation time measured in order to acquire parameters capable of discriminating an LA specimen and a DAC specimen, in combination with the above first coagulation time. The second coagulation time measurement reagent contains a metal ion and/or normal plasma. In this embodiment, the metal ion and the normal plasma are reagents added to the blood specimen of a subject in order to acquire such a second coagulation time. Hereinafter, "a metal ion and/or normal plasma" contained in the coagulation time measurement reagent of this embodiment is also referred to as "preparation reagent".

The second coagulation time measurement reagent may be a reagent for measuring coagulation time based on the measurement principle known in the art. In a preferred embodiment, the second coagulation time measurement reagent is a reagent for measuring the same type of coagulation time as the first coagulation time measurement reagent. The second coagulation time measurement reagent contains the above component necessary for coagulation according to the type of the coagulation time to be measured. In this embodiment, the second coagulation time measurement reagent may be a one-liquid type reagent containing a component necessary for coagulation and a preparation reagent. In addition, the second coagulation time measurement reagent may be a two-liquid type reagent containing a first partial reagent containing a component necessary for coagulation and a second partial reagent containing a preparation reagent. In this case, the first partial reagent containing a component necessary for coagulation may be the same as the first coagulation time measurement reagent.

The second coagulation time measurement reagent may contain phospholipid. Details of the phospholipid are as described above. In the case where the second coagulation time measurement reagent is the above two-liquid type reagent, the phospholipid may be contained in either the first partial reagent or the second partial reagent. In a preferred embodiment, the phospholipid is contained in the first partial reagent.

The second coagulation time measurement reagent may contain calcium ions, in order to initiate blood coagulation. Details of the calcium ion are as described above. In the case where the second coagulation time measurement reagent is the above two-liquid type reagent, calcium ions may be contained in either the first partial reagent or the second partial reagent. In a preferred embodiment, calcium ions are contained in the first partial reagent. Alternatively, the second coagulation time measurement reagent may be a two-liquid type reagent containing a first partial reagent containing a component necessary for coagulation and a preparation reagent, or a component necessary for coagulation, a preparation reagent and phospholipid, and a third partial reagent containing calcium ions. Alternatively, the second coagulation time measurement reagent may be a three-liquid type reagent containing a first partial reagent containing a component necessary for coagulation or a component necessary for coagulation and phospholipid, a second partial reagent containing a preparation reagent, and a third partial reagent containing calcium ions. The second partial reagent of the first coagulation time measurement reagent and the third partial reagent of the second coagulation time measurement reagent may be the same reagent.

The second measurement sample is prepared by mixing the blood specimen with the second coagulation time measurement reagent. In the case where the second coagulation time measurement reagent is a two-liquid type reagent containing, for example, a first partial reagent containing a component necessary for coagulation and a second partial reagent containing a preparation reagent, the order of mixing the blood specimen and these partial reagents is not particularly limited. In a preferred embodiment, the blood specimen and the preparation reagent are mixed first. Specifically, the second measurement sample is prepared as follows. First, the second partial reagent containing a preparation reagent is added to the blood specimen to prepare a mixture. Subsequently, the resulting mixture is mixed with the first partial reagent containing a component necessary for coagulation. The reaction time of the blood specimen with the second partial reagent (preparation reagent) is not essentially, but usually 180 minutes or less, and preferably 30 minutes or less. The temperature condition is usually 15° C. or more and 45° C. or less, and preferably 15° C. or more and 38° C. or less. The reaction conditions of the above mixture with the first partial reagent may be the same as the reaction conditions of the blood specimen with the first coagulation time measurement reagent.

In this embodiment, the preparation reagent shows different reactivity to LA and DAC, respectively. Here, LA is involved in an antigen-antibody reaction against phospholipid, and DAC is involved in an enzymatic reaction between a coagulation factor and a substrate. Therefore, the preparation reagent has different reactivity to the enzyme reaction and the antigen-antibody reaction, respectively. By adding a preparation reagent having such properties to the blood specimen, the above second coagulation time can be acquired.

A metal ion as a preparation reagent shows different reactivity for LA and DAC, respectively. Examples of such a metal ion include a nickel ion, a cobalt ion, a manganese ion, a zinc ion, an aluminum ion and an iron ion, a sodium ion, and a potassium ion. Among them, a cobalt ion, a zinc ion, an aluminum ion, a sodium ion and a potassium ion are preferable. In this embodiment, two or more kinds of metal ions may be used as a preparation reagent.

It is preferable that the metal ion as a preparation reagent is supplied into the second measurement sample by a metal compound soluble in an aqueous solvent or a solution thereof. Such a compound is not particularly limited as long as the metal ion is generated in the blood specimen and the anion generated from the compound does not inhibit the coagulation reaction. In this embodiment, a salt of at least one metal selected from nickel, cobalt, manganese, zinc, aluminum, iron, sodium and potassium with an inorganic acid or an organic acid is preferable. In particular, a salt of the above metal and an inorganic acid is preferable, and examples include salts of a strong acid such as hydrochloric acid, sulfuric acid or nitric acid and the above metal. Among them, chlorides of the above metal and sodium sulfate are particularly preferable. The salt may be an anhydride or a hydrate. In this embodiment, it is preferable to use the preparation reagent in the form of a solution in which a salt capable of generating the above metal ion is dissolved in an appropriate solvent, particularly in the form of an aqueous solution.

When the preparation reagent is at least one metal ion selected from a cobalt ion, a nickel ion, a manganese ion, a zinc ion, an aluminum ion and an iron ion, the concentration of the added metal ion is preferably 0.01 mmol/L or more and 100 mmol/L or less, in the mixture of the blood specimen and the preparation reagent. When the preparation reagent is at least one metal ion selected from a sodium ion and a potassium ion, the concentration of the added metal ion is preferably 1 mmol/L or more and 5 mol/L or less, in the mixture of the blood specimen and the preparation reagent. Here, the "concentration of the added metal ion" refers to the concentration of the metal ion supplied by the preparation reagent, and it is intended that the concentration of the metal ion contained in the blood specimen itself is not included. In this embodiment, in the case of using an aqueous solution of an inorganic acid salt of the above metal as a preparation reagent, the concentration of the metal ion in the mixture of the blood specimen and the preparation reagent may be represented by the concentration of the inorganic acid salt.

The present inventors have found that normal plasma shows different reactivity for LA and DAC, respectively. Normal plasma as a preparation reagent may be plasma derived from a healthy subject. For example, normal pooled plasma prepared in a medical institution or the like may be used, or commercially available normal plasma may be used. In this embodiment, it is preferable to prepare a second measurement sample by mixing the blood specimen and normal plasma at a volume ratio of 1:1 and mixing the resulting mixture with the first coagulation time measurement reagent.

Measurement of second coagulation time is carried out promptly after preparation of the second measurement sample. Specifically, in the case where the second coagulation time measurement reagent is a two-liquid type or three-liquid type reagent containing a preparation reagent and calcium ions as separate partial reagents, the measurement of the second coagulation time is started, from the time when the partial reagent containing calcium ions is added to the mixture of the blood specimen and the partial reagent containing a preparation reagent. When the second coagulation time measurement reagent is a one-liquid type reagent containing calcium ions or snake venom, the measurement of the second coagulation time is started from the time when the reagent is added to the blood specimen.

Measurement of second coagulation time may be carried out by a manual method or may be carried out by the above fully automated coagulation time measurement device. Preferably, the second coagulation time is measured by the same means as the first coagulation time. In this embodiment, the first coagulation time and the second coagulation time may be simultaneously measured or sequentially measured. In the case of sequentially measuring the first coagulation time and the second coagulation time, the measurement order is not particularly limited.

In general, in the test of LA, the coagulation time of normal plasma derived from a healthy subject may be measured as a control. However, the present inventors have found that the blood specimen can be determined whether it is an LA specimen or a DAC specimen, based on the parameters acquired from the coagulation time of the blood specimen of a subject (first coagulation time) and the coagulation time of the mixture of the blood specimen and a preparation reagent (second coagulation time). That is, according to the method of this embodiment, the coagulation time of normal plasma itself is not required for determination.

In the method of this embodiment, a value based on the first coagulation time and the second coagulation time is acquired. Such values are preferably at least one of a value related to the product of the first coagulation time and the second coagulation time and a value related to the ratio of the first coagulation time and the second coagulation time. These values are parameters used for discriminating an LA specimen and a DAC specimen. As described above, in the method of this embodiment, the coagulation time of normal plasma is not required, so that the coagulation time of normal plasma is not used when acquiring the above values related to the product and the ratio.

The value related to the product of the first coagulation time and the second coagulation time includes not only the value itself of the product of the first coagulation time and the second coagulation time but also values calculated from the value of the product. Examples of the values calculated from the value of the product of the first coagulation time and the second coagulation time include a value obtained by multiplying the value of the product by a constant, a value obtained by adding a constant to the value of the product, a value obtained by subtracting a constant from the value of the product, a reciprocal of the value of the product, values obtained by combining these calculations, and the like. In this embodiment, the value related to the product of the first coagulation time and the second coagulation time is preferably a value calculated by equation (1) below.

(Value related to product of first coagulation time and second coagulation time)=(First coagulation time)×(Second coagulation time)   Equation (1)

The value related to the ratio of the first coagulation time and the second coagulation time includes not only the value itself of the ratio of the first coagulation time and the second coagulation time but also values calculated from the value of the ratio. Examples of the value calculated from the value of the ratio of the first coagulation time and the second coagulation time include a value obtained by multiplying the value of the ratio by a constant, a value obtained by adding a constant to the value of the ratio, a value obtained by subtracting a constant from the value of the ratio, a reciprocal of the value of the ratio, values obtained by combining these calculations, and the like. In this embodiment, the value related to the ratio of the first coagulation time and the second coagulation time is preferably a value calculated by equation (2) or (3) below.

(Value related to ratio of first coagulation time and second coagulation time)=(First coagulation time)/(Second coagulation time)   Equation(2) or (Value related to ratio of first coagulation time and second coagulation time)=(Second coagulation time)/(First coagulation time)   Equation (3)

According to the method of this embodiment, it is possible to determine whether the blood specimen of a subject is a blood specimen containing LA or a blood specimen containing DAC, based on the acquired value. In a preferred embodiment, the acquired value is compared with a threshold value corresponding to the acquired value, and determination is made on the blood specimen of a subject, based on the comparison result.

For example, the value of the product calculated by equation (1) tends to be higher in the DAC specimen than in the LA specimen regardless of which preparation reagent is used. Therefore, when the value of the product calculated by equation (1) is lower than the predetermined threshold value, the blood specimen of a subject may be determined to be a specimen containing LA. When the value of the product calculated by equation (1) is higher than the predetermined threshold value or is equal to the predetermined threshold value, the blood specimen of a subject may be determined to be a specimen containing DAC.

The value related to the ratio of the first coagulation time and the second coagulation time differs in the result of comparison with the predetermined threshold value, depending on the kind of the preparation reagent. For example, when a nickel ion, a cobalt ion, a manganese ion, a sodium ion or a potassium ion is used as a preparation reagent, the value of the ratio calculated by equation (2) tends to be higher in the LA specimen than in the DAC specimen. Therefore, in the case of using these preparation reagents, when the value of the ratio calculated by equation (2) is higher than the predetermined threshold value or is equal to the predetermined threshold value, the blood specimen of a subject may be determined to be a specimen containing LA. When the value of the ratio calculated by equation (2) is lower than the predetermined threshold value, the blood specimen of a subject may be determined to be a specimen containing DAC.

On the other hand, when normal plasma, a zinc ion, an aluminum ion or an iron ion is used as a preparation reagent, the value of the ratio calculated by equation (2) tends to be higher in the DAC specimen than in the LA specimen. Therefore, in the case of using these preparation reagents, when the value of the ratio calculated by equation (2) is lower than the predetermined threshold value, the blood specimen of a subject may be determined to be a specimen containing LA. When the value of the ratio calculated by equation (2) is higher than the predetermined threshold value or is equal to the predetermined threshold value, the blood specimen of a subject may be determined to be a specimen containing the DAC.

The ratio calculated by equation (3) is the reciprocal of the ratio calculated by equation (2). Therefore, the determination result using the value of the ratio calculated by equation (3) is opposite to the determination result using the value of the ratio calculated by equation (2). Specifically, in the case of using a nickel ion, a cobalt ion, a manganese ion, a sodium ion or a potassium ion as a preparation reagent, when the value of the ratio calculated by equation (3) is lower than the predetermined threshold value, the blood specimen of a subject may be determined to be a specimen containing LA. When the value of the ratio calculated by equation (3) is higher than the predetermined threshold value or is equal to the predetermined threshold value, the blood specimen of a subject may be determined to be a specimen containing DAC.

In the case where normal plasma, a zinc ion, an aluminum ion or an iron ion is used as a preparation reagent, when the value of the ratio calculated by equation (3) is higher than the predetermined threshold value or is equal to the predetermined threshold value, the blood specimen of a subject may be determined to be a specimen containing LA. When the value of the ratio calculated by equation (3) is lower than the predetermined threshold value, the blood specimen of a subject may be determined to be a specimen containing DAC.

In this embodiment, the numerical value itself of the predetermined threshold value is not particularly limited. For example, the predetermined threshold value can be empirically set by accumulating data on the coagulation time of blood specimens of the LA-positive patients and blood specimens of the patients who received DAC. Alternatively, values related to the product and values related to the ratio of the first coagulation time and the second coagulation time were acquired from each of the group of blood specimens of the LA-positive patients and the group of blood specimens of the patients who received DAC, and a value that can clearly distinguish both groups can be set as the predetermined threshold value, based on the acquired values. For the calculation of the predetermined threshold value, a statistical method such as ROC analysis may be used.

[2. Method for Determining Blood Specimen Using Plural Kinds of Coagulation Time Measurement Reagents with Different Phospholipid Concentrations]

In a further embodiment, the method of this embodiment may be carried out using plural kinds of coagulation time measurement reagents with different phospholipid concentrations. Hereinafter, a method for determining a blood specimen according to the second aspect will be described.

In this embodiment, a first coagulation time measurement reagent, a second coagulation time measurement reagent containing a preparation reagent, a third coagulation time measurement reagent containing phospholipids at a concentration higher than that of the first coagulation time measurement reagent and a fourth coagulation time measurement reagent containing a preparation reagent and containing phospholipids at a concentration higher than that of the first coagulation time measurement reagent are used. Details of the preparation reagent are as described above.

The first and second coagulation time measurement reagents may not contain phospholipid. In a preferred embodiment, the first coagulation time measurement reagent contains phospholipids at a concentration lower than that of the second coagulation time measurement reagent, and the second coagulation time measurement reagent contains phospholipids at a concentration lower than that of the fourth coagulation time measurement reagent. In this case, in the case where the blood specimen and the reagent are mixed in a volume ratio of 1:1, the concentration of phospholipids in the first and second coagulation time measurement reagents is usually 20 to 150 µg/mL, and preferably 30 to 70 µg/mL. The phospholipid concentrations of the first and second coagulation time measurement reagents may be the same or different. In the case where the blood specimen and the reagent are mixed in a volume ratio of 1:1, the concentration of phospholipids in the third and fourth coagulation time measurement reagents is usually 150 to 2000 µg/mL, and preferably 150 to 600 µg/mL. The phospholipid concentrations of the third and fourth coagulation time measurement reagents may be the same or different. In the case where the mixing ratio of the blood specimen and each coagulation time measurement reagent is not 1:1, the concentration of phospholipids in each reagent may be appropriately adjusted according to the mixing ratio. The kinds of the phospholipids are as described above.

The first, second, third and fourth coagulation time measurement reagents contain the component necessary for coagulation described above according to the type of the coagulation time to be measured. Commercially available coagulation time measurement reagents and reagent kits may be used. It is the mainstream in the art to first measure dRVVT for screening of LA specimens. Therefore, in this embodiment, it is preferred that the first coagulation time measurement reagent is a reagent containing snake venom and phospholipids (dRVVT measurement reagent), and the third coagulation time measurement reagent is a reagent containing snake venom and phospholipids at a concentration higher than that of the first coagulation time measurement reagent. In this case, it is preferred that the second coagulation time measurement reagent is a reagent containing snake venom, phospholipids and a preparation reagent, and the fourth coagulation time measurement reagent is a reagent containing snake venom, phospholipids at a concentration higher than that of the first coagulation time measurement reagent and a preparation reagent.

The first, second, third and fourth coagulation time measurement reagents may contain calcium ions, in order to initiate blood coagulation. In this case, the first and third coagulation time measurement reagents may be one-liquid type reagents containing a component necessary for coagulation, phospholipids, and calcium ions. In addition, the second and fourth coagulation time measurement reagents may be one-liquid type reagents containing a component necessary for coagulation, a preparation reagent, phospholipids, and calcium ions. Alternatively, the first and third coagulation time measurement reagents may be two-liquid type reagents comprising a first partial reagent containing a component necessary for coagulation and phospholipids and a second partial reagent containing calcium ions. The second and fourth coagulation time measurement reagents are two-liquid type reagents containing a first partial reagent containing a component necessary for coagulation, a preparation reagent and phospholipids, and a third partial reagent containing calcium ions. Alternatively, the second coagulation time measurement reagent may be a three-liquid type reagent containing a first partial reagent containing a component necessary for coagulation and phospholipids, a second partial reagent containing a preparation reagent, and a third partial reagent containing calcium ions. Partial reagents containing calcium ions of each coagulation time measurement reagent may be the same reagent. Details of the calcium ion are as described above.

In this embodiment, first coagulation time and second coagulation time are measured, using the first and second coagulation time measurement reagents, respectively, as described above. Furthermore, third coagulation time and fourth coagulation time are measured, using the third and fourth coagulation time measurement reagents, respectively. Specifically, a third measurement sample is prepared by mixing the blood specimen of a subject with the third coagulation time measurement reagent, and third coagulation time is measured. A fourth measurement sample is prepared by mixing the blood specimen of a subject with the fourth coagulation time measurement reagent, and fourth coagulation time is measured.

In this embodiment, measurement of third coagulation time can be performed in the same manner as measurement of first coagulation time except that the third coagulation time measurement reagent is used in place of the first coagulation time measurement reagent. Similarly, measurement of fourth coagulation time can be performed in the same manner as measurement of second coagulation time except that the fourth coagulation time measurement reagent is used in place of the second coagulation time measurement reagent. These four coagulation times are preferably measured by the same means. In this embodiment, these four coagulation times may be simultaneously measured or sequentially measured. In the case of sequentially measuring these four coagulation times, the measurement order is not particularly limited.

In the method of this embodiment, a value based on the first coagulation time and the second coagulation time is acquired as described above. Preferably, at least one of values related to the product of the first coagulation time and the second coagulation time and values related to the ratio of the first coagulation time and the second coagulation time is acquired. Further, values based on the third coagulation time and the fourth coagulation time are acquired. Preferably, at least one of values related to the product of the third coagulation time and the fourth coagulation time and values related to the ratio of the third coagulation time and the fourth coagulation time is acquired. The coagulation time of normal plasma is not used when acquiring the above values related to the product and the ratio.

The values related to the product of the third coagulation time and the fourth coagulation time include not only the value itself of the product of the third coagulation time and the fourth coagulation time but also values calculated from the value of the product. Examples of the values calculated from the value of the product of the third coagulation time and the fourth coagulation time include a value obtained by multiplying the value of the product by a constant, a value obtained by adding a constant to the value of the product, a value obtained by subtracting a constant from the value of the product, a reciprocal of the value of the product, values obtained by combining these calculations, and the like. In this embodiment, the value related to the product of the third coagulation time and the fourth coagulation time is preferably a value calculated by equation (1') below.

(Values related to product of third coagulation time and fourth coagulation time)=(Third coagulation time)×(Fourth coagulation time)   Equation (1')

The value related to the ratio of the third coagulation time and the fourth coagulation time includes not only the value itself of the ratio of the third coagulation time and the fourth coagulation time but also values calculated from the value of the ratio. Examples of the value calculated from the value of the ratio of the third coagulation time and the fourth coagulation time include a value obtained by multiplying the value of the ratio by a constant, a value obtained by adding a constant to the value of the ratio, a value obtained by subtracting a constant from the value of the ratio, a reciprocal of the value of the ratio, values obtained by combining these calculations, and the like. In this embodiment, the value related to the ratio of the third coagulation time and the fourth coagulation time is preferably a value calculated by equation (2') or (3') below.

(Value related to ratio of third coagulation time and fourth coagulation time)=(Third coagulation time)/(Fourth coagulation time)   Equation (2') or (Value related to ratio of third coagulation time and fourth coagulation time)=(Fourth coagulation time)/(Third coagulation time)   Equation (3')

According to the method of this embodiment, it is possible to determine whether the blood specimen of a subject is a blood specimen containing LA or a blood specimen containing DAC, based on the acquired value. For example, it is possible to make a determination on the blood specimen of a subject based on the value related to the ratio of the first coagulation time and the second coagulation time and the value related to the ratio of the third coagulation time and the fourth coagulation time. In a preferred embodiment, the value of the index calculated by equation (4) or (5) below is compared with the threshold value corresponding to the index, and a determination is made based on the comparison result.

(Index)=[(Second coagulation time)/(First coagulation time)]×[(Fourth coagulation time)/(Third coagulation time)]   Equation (4) or (Index)=[(First coagulation time)/(Second coagulation time)]×[(Third coagulation time)/(Fourth coagulation time)]   Equation (5)

The value of the index calculated by equation (4) differs in the result of comparison with the predetermined threshold value, depending on the kind of the preparation reagent. For example, when a nickel ion, a cobalt ion, a manganese ion, a sodium ion or a potassium ion is used as a preparation reagent, the value of the index calculated by equation (4) tends to be higher in the DAC specimen than in the LA specimen. Therefore, in the case of using these preparation reagents, when the value of the index calculated by equation (4) is lower than the predetermined threshold value, the blood specimen of a subject may be determined to be a specimen containing LA. When the value of the index calculated by equation (4) is higher than the predetermined threshold value or is equal to the predetermined threshold value, the blood specimen of a subject may be determined to be a specimen containing DAC.

On the other hand, when normal plasma, a zinc ion, an aluminum ion or an iron ion is used as a preparation reagent, the value of the index calculated by equation (4) tends to be higher in the LA specimen than in the DAC specimen. Therefore, in the case of using these preparation reagents, when the value of the index calculated by equation (4) is higher than the predetermined threshold value or is equal to the predetermined threshold value, the blood specimen of a subject may be determined to be a specimen containing LA. When the value of the index calculated by equation (4) is lower than the predetermined threshold value, the blood specimen of a subject may be determined to be a specimen containing DAC.

The index calculated by equation (5) is the reciprocal of the index calculated by equation (4). Therefore, the determination result using the value of the index calculated by equation (5) is opposite to the determination result using the value of the index calculated by equation (4). Specifically, in the case of using a nickel ion, a cobalt ion, a manganese ion, a sodium ion or a potassium ion as a preparation reagent, when the value of the index calculated by equation (5) is higher than the predetermined threshold value or is equal to the predetermined threshold value, the blood specimen of a subject may be determined to be a specimen containing LA. When the value of the ratio calculated by equation (5) is lower than the predetermined threshold value, the blood specimen of a subject may be determined to be a specimen containing DAC.

In the case where normal plasma, a zinc ion, an aluminum ion or an iron ion is used as a preparation reagent, when the value of the index calculated by equation (5) is lower than the predetermined threshold value, the blood specimen of a subject may be determined to be a specimen containing LA.

When the value of the index calculated by equation (5) is higher than the predetermined threshold value or is equal to the predetermined threshold value, the blood specimen of a subject may be determined to be a specimen containing DAC.

Equation (4) above can be transformed into equation (4A) or (4B) below. Equation (5) above can be transformed into equation (5A) or (5B) below. In this embodiment, the value of the index calculated by equation (4A) or (4B) below is regarded as the value of the index calculated by equation (4) above. The value of the index calculated by equation (5A) or (5B) below is regarded as the value of the index calculated by equation (5) above.

(Index)=[(Second coagulation time)×(Fourth coagulation time)]/[(First coagulation time)×(Third coagulation time)]    Equation (4A) or (Index)=[(Second coagulation time)/(Third coagulation time)]×[(Fourth coagulation time)/(First coagulation time)]    Equation (4B)

(Index)=[(First coagulation time)×(Third coagulation time)]/[(Second coagulation time)×(Fourth coagulation time)]    Equation (5A) or (Index)=[(Fourth coagulation time)/(First coagulation time)]×[(Second coagulation time)/(Third coagulation time)]    Equation (5B)

In a further embodiment, it is possible to make a determination on the blood specimen of a subject based on the value related to the product of the first coagulation time and the second coagulation time and the value related to the product of the third coagulation time and the fourth coagulation time. In a preferred embodiment, the value of the index calculated by equation (6) below is compared with the threshold value corresponding to the index, and a determination is made based on the comparison result.

(Index)=[(First coagulation time)×(Second coagulation time)]×[(Third coagulation time)×(Fourth coagulation time)]    Equation (6)

The value of the index calculated by equation (6) tends to be higher in the DAC specimen than in the LA specimen regardless of which preparation reagent is used. Therefore, when the value of the index calculated by equation (6) is lower than the predetermined threshold value, the blood specimen of a subject may be determined to be a specimen containing LA. When the value of the index calculated by equation (6) is higher than the predetermined threshold value or is equal to the predetermined threshold value, the blood specimen of a subject may be determined to be a specimen containing DAC.

The value of the index calculated by equation (6) above can also be said as the value of the product of the first coagulation time, the second coagulation time, the third coagulation time, and the fourth coagulation time. In this embodiment, the value of the product of the four coagulation times is regarded as the value of the index calculated by equation (6) above.

In the method of this embodiment using plural kinds of coagulation time measurement reagents with different phospholipid concentrations, it is also possible to examine whether the blood specimen of a subject is a specimen suspected of containing LA. Specifically, first, the value of the ratio of the first coagulation time and the third coagulation time is calculated by equation (7) below, or the value of the ratio of the second coagulation time and the fourth coagulation time is calculated by equation (8) below.

(Value of ratio of first coagulation time and third coagulation time)=(First coagulation time)/(Third coagulation time)    Equation (7) or (Value of ratio of second coagulation time and fourth coagulation time)=(Second coagulation time)/(Fourth coagulation time)    Equation (8)

When the blood specimen is a specimen not containing LA and DAC, such as a blood specimen derived from a healthy subject, the values of the ratios calculated by equations (7) and (8) are approximately 1.0. On the other hand, when the blood specimen contains LA, since prolongation of coagulation time depends on phospholipid, the values of the ratios calculated by equations (7) and (8) are higher than 1.0. Therefore, based on the value of the ratio calculated by equation (7) or (8), it is possible to select a specimen suspected of containing LA among the blood specimens of a subject as a determination target. In this embodiment, the blood specimen may be determined when the value of the ratio of the first coagulation time and the third coagulation time calculated for the blood specimen of a subject is 1.3 or more, or the calculated value of the ratio of the second coagulation time and the fourth coagulation time is 1.5 or more.

[3. Method for Determining Blood Specimen Using Different Phospholipid Concentrations and Two Kinds of Coagulation Time Measurement Reagents Containing Preparation Reagent]

In a further embodiment, the blood specimen of a subject can be discriminated also by using the value based on the second coagulation time and the fourth coagulation time. Hereinafter, a method for determining a blood specimen according to the third aspect will be described.

In this embodiment, a first coagulation time measurement reagent containing a coagulation time measurement reagent containing phospholipid and a preparation reagent containing a metal ion and/or normal plasma is used. A second coagulation time measurement reagent containing a coagulation time measurement reagent containing phospholipid at a concentration higher than that of the first coagulation time measurement reagent and a preparation reagent containing a metal ion and/or normal plasma is used. The first and second coagulation time measurement reagents used in this aspect respectively correspond to the second and fourth coagulation time measurement reagents used in the method of the second aspect described above.

In this embodiment, a first measurement sample is prepared by mixing a blood specimen of a subject with the above first coagulation time measurement reagent, and first coagulation time is measured. A second measurement sample is prepared by mixing the blood specimen with the above second coagulation time measurement reagent, and second coagulation time is measured. The first and second coagulation times measured in this embodiment respectively correspond to the second and fourth coagulation times measured by the method of the second aspect described above. Details of preparation and measurement of each measurement sample are the same as those described for the method of the second aspect.

In this embodiment, a value based on the first coagulation time and the second coagulation time is acquired. This value is used for discriminating the LA specimen and the DAC specimen. As such a value, the value related to the ratio of the first coagulation time and the second coagulation time is preferable. The value related to the ratio of the first coagulation time and the second coagulation time includes not only the value itself of the ratio of the first coagulation time and the second coagulation time but also values calculated from the value of the ratio. Examples of the value calculated from the value of the ratio of the first coagulation time and the second coagulation time include a value obtained by multiplying the value of the ratio by a constant, a value obtained by adding a constant to the value of the ratio, a value obtained by subtracting a constant from the value of the ratio, a reciprocal of the value of the ratio, values obtained by combining these calculations, and the like. In this embodiment, the value related to the ratio of the first coagulation time and the second coagulation time is preferably a value calculated by equation (9) or (10) below.

(Value related to ratio of first coagulation time and second coagulation time)=(First coagulation time)/(Second coagulation time)     Equation (9)

(Value related to ratio of first coagulation time and second coagulation time)=(Second coagulation time)/(First coagulation time)     Equation (10)

The value related to the ratio of the first coagulation time and the second coagulation time differs in the result of comparison with the predetermined threshold value, depending on the kind of the preparation reagent. For example, when a zinc ion, an aluminum ion or an iron ion is used as a preparation reagent, the value of the ratio calculated by equation (9) tends to be higher in the LA specimen than in the DAC specimen. Therefore, in the case of using these preparation reagents, when the value of the ratio calculated by equation (9) is higher than the predetermined threshold value or is equal to the predetermined threshold value, the blood specimen of a subject may be determined to be a specimen containing LA. When the value of the ratio calculated by equation (9) is lower than the predetermined threshold value, the blood specimen of a subject may be determined to be a specimen containing DAC.

On the other hand, when a nickel ion, a cobalt ion or a sodium ion is used as a preparation reagent, the value of the ratio calculated by equation (9) tends to be higher in the DAC specimen than in the LA specimen. Therefore, in the case of using these preparation reagents, when the value of the ratio calculated by equation (9) is lower than the predetermined threshold value, the blood specimen of a subject may be determined to be a specimen containing LA. When the value of the ratio calculated by equation (9) is higher than the predetermined threshold value or is equal to the predetermined threshold value, the blood specimen of a subject may be determined to be a specimen containing DAC.

The ratio calculated by equation (10) is the reciprocal of the ratio calculated by equation (9). Therefore, the determination result using the value of the ratio calculated by equation (10) is opposite to the determination result using the value of the ratio calculated by equation (9). Specifically, in the case where a zinc ion, an aluminum ion or an iron ion is used as a preparation reagent, when the value of the ratio calculated by equation (10) is lower than the predetermined threshold value, the blood specimen of a subject may be determined to be a specimen containing LA. When the value of the ratio calculated by equation (10) is higher than the predetermined threshold value or is equal to the predetermined threshold value, the blood specimen of a subject may be determined to be a specimen containing DAC.

In the case where a nickel ion, a cobalt ion or a sodium ion is used as a preparation reagent, when the value of the ratio calculated by equation (10) is higher than the predetermined threshold value or is equal to the predetermined threshold value, the blood specimen of a subject may be determined to be a specimen containing LA. When the value of the ratio calculated by equation (10) is lower than the predetermined threshold value, the blood specimen of a subject may be determined to be a specimen containing DAC.

[4. Device and Computer Program for Analysis of Blood Coagulation]

An example of the blood specimen analyzer according to this embodiment will be described hereinbelow, with reference to the drawings. However, this embodiment is not limited only to this example. As shown in FIG. 1, a blood specimen analyzer 10 includes a measurement device 50 for preparing and optically measuring a measurement sample, a control device 40 for analyzing measurement data acquired by the measurement device 50 and giving an instruction to the measurement device 50. The measurement device 50 includes a measurement unit 20 for acquiring optical information on the light amount from the measurement sample, and a specimen transporting unit 30 arranged in front of the measurement unit 20.

The measurement unit 20 is provided with lids 20a and 20b, a cover 20c, and a power button 20d. A user can open the lid 20a and replace a reagent container 103 placed in reagent tables 11 and 12 (see FIG. 2) with a new reagent container 103, or a user can newly add another reagent container 103. To the reagent container 103 is attached a barcode label 103a printed with a barcode including the kind of the reagent to be accommodated and a reagent ID made up of serial number provided to the reagent.

Figure 2:
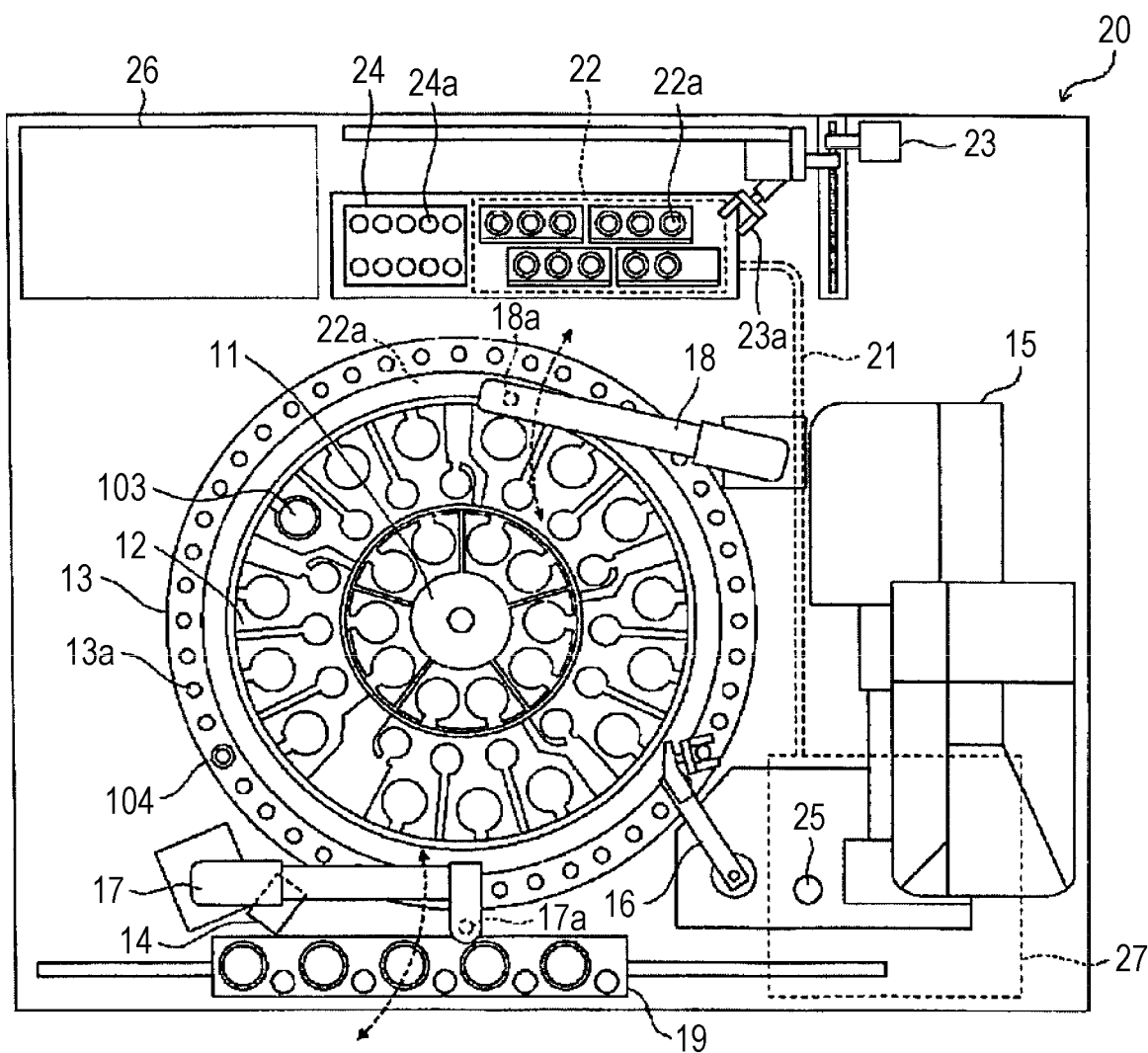
FIG. 2 is a plan view of the inside of a measurement unit of the blood specimen analyzer when viewed from above.

The user can open the lid 20b and replace a lamp unit 27 (see FIG. 2). The user can also open the cover 20c and replace a piercer 17a (see FIG. 2). The specimen transporting unit 30 transports a specimen container 101 supported by a specimen rack 102 to an aspiration position by the piercer 17a. The specimen container 101 is hermetically sealed by a rubber lid 101a.

In the case of using the blood specimen analyzer 10, the user first presses the power button 20d of the measurement unit 20 to activate the measurement unit 20, and the user presses a power button 439 of the control device 40 to activate the control device 40. When the control device 40 is activated, a log-on screen is displayed on a display unit 41. The user inputs the user name and the password on the log-on screen to log on to the control device 40, and starts using the blood specimen analyzer 10.

The configuration of the measurement device will be described below. As shown in FIG. 2, the measurement unit 20 includes reagent tables 11 and 12, a cuvette table 13, a barcode reader 14, a cuvette supply section 15, a catcher 16, a specimen dispensing arm 17, a reagent dispensing arm 18, an urgent specimen setting section 19, an optical fiber 21, a detecting section 22, a cuvette transfer section 23, a warming section 24, a disposal port 25, a fluid section 26, and a lamp unit 27.

(Measurement Sample Preparing Section)

Each of the reagent tables 11 and 12 and the cuvette table 13 has an annular shape. Each of the reagent tables 11 and 12 and the cuvette table 13 is configured rotatably. Each of the reagent tables 11 and 12 corresponds to a reagent storing section, onto which a reagent container 103 is placed. The barcode of the reagent container 103 placed on the reagent tables 11 and 12 is read by the barcode reader 14. Information (kind of reagent, reagent ID) read from the barcode is inputted to the control device 40 and stored in a hard disk 434 (see FIG. 7).

In the device of this embodiment, a reagent container 103, in which a first partial reagent and a second partial reagent (aqueous calcium chloride solution) of a first coagulation time measurement reagent, a first partial reagent, a second partial reagent (preparation reagent) and a third partial reagent (calcium chloride aqueous solution) of a second coagulation time measurement reagent and the like are each accommodated, is placed on the reagent tables 11 and/or 12. A reagent container 103 in which partial reagents of third and fourth coagulation time measurement reagents are each accommodated may be further placed. In this example, the coagulation time measurement reagents are a two-liquid type or three-liquid type reagent, but these may be one-liquid type reagents.

The cuvette table 13 is formed with a support portion 13a composed of a plurality of holes capable of supporting a cuvette 104. A new cuvette 104 introduced into the cuvette supply section 15 by the user is sequentially transferred by the cuvette supply section 15, and the cuvette 104 is placed on the support portion 13a of the cuvette table 13 by the catcher 16.

A stepping motor is connected to each of the specimen dispensing arm 17 and the reagent dispensing arm 18 so as to be able to move up and down and rotatably. A piercer 17a of which a tip is sharply formed is provided at the tip of the specimen dispensing arm 17, so that the lid 101a of the specimen container 101 can be punctured. A pipette 18a is provided at the tip of the reagent dispensing arm 18. The tip of the pipette 18a is formed flat unlike the piercer 17a. An electrostatic capacitance type liquid level detection sensor 213 (see FIG. 3) is connected to the pipette 18a.

When the specimen container 101 is transported to a predetermined position by the specimen transporting section 30 (see FIG. 1), the piercer 17a is positioned just above the specimen container 101 by the rotational movement of the specimen dispensing arm 17. Then, the specimen dispensing arm 17 is moved downward, the piercer 17a penetrates the lid 101a of the specimen container 101, and the blood specimen accommodated in the specimen container 101 is aspirated by the piercer 17a. In the case where an urgent blood specimen is set in the urgent specimen setting section 19, the piercer 17a intervenes in the specimen supplied from the specimen transporting unit 3 and aspirates the urgent blood specimen. The blood specimen aspirated by the piercer 17a is discharged into an empty cuvette 104 on the cuvette table 13.

The cuvette 104 into which the blood specimen has been discharged is transferred from the support portion 13a of the cuvette table 13 to a support portion 24a of the warming section 24 by a catcher 23a of the cuvette transfer section 23. The warming section 24 warms the blood specimen accommodated in the cuvette 104 placed in the support portion 24a at a predetermined temperature (for example, 37° C.) for a certain period of time. When the warming of the blood specimen by the warming section 24 is finished, the cuvette 104 is again gripped by the catcher 23a. Then, the cuvette 104 is positioned at a predetermined position while being gripped by the catcher 23a, and in this state, the reagent aspirated by the pipette 18a is discharged into the cuvette 104.

In the dispensing of the reagent by the pipette 18a, first, the reagent tables 11 and 12 are rotated, and the reagent container 103 that accommodates the reagent corresponding to the measurement item is transported to an aspiration position by the pipette 18a. Then, after the position of the pipette 18a in the vertical direction is positioned at the origin position, the pipette 18a is lowered until the lower end of the pipette 18a comes into contact with the liquid level of the reagent by the liquid level detection sensor 213. When the lower end of the pipette 18a comes into contact with the liquid level of the reagent, the pipette 18a is further lowered to an extent that a necessary amount of the reagent can be aspirated. Then, the lowering of the pipette 18a is stopped, and the reagent is aspirated by the pipette 18a. The reagent aspirated by the pipette 18a is discharged into the cuvette 104 gripped by the catcher 23a. Then, the blood specimen and the reagent in the cuvette 104 are agitated by the vibrating function of the catcher 23a. Thus, the measurement sample is prepared. Thereafter, the cuvette 104 that accommodates the measurement sample is transferred to a support portion 22a of the detecting section 22 by the catcher 23a.

(Optical Information Acquiring Section)

Figure 4:
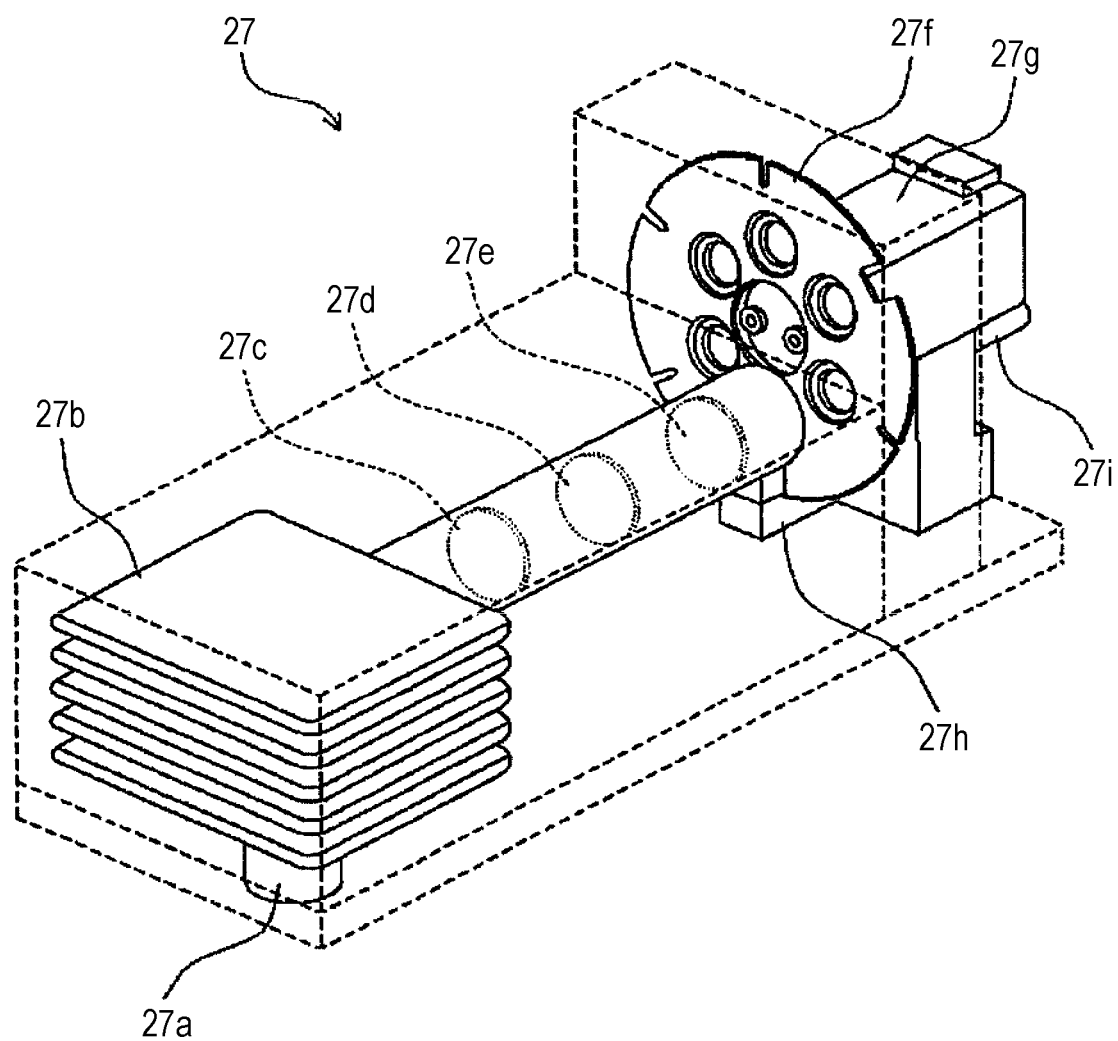
FIG. 4 is a diagram showing the configuration of a lamp unit provided in the measurement device.

The lamp unit 27 supplies light having plural kinds of wavelengths used for detection of an optical signal by the detecting section 22. An example of the configuration of the lamp unit 27 will be described with reference to FIG. 4. The lamp unit 27 corresponds to a light source, and includes a halogen lamp 27a, a lamp case 27b, condenser lenses 27c to 27e, a disk-shaped filter section 27f, a motor 27g, a light transmission type sensor 27h, and an optical fiber coupler 27i.

With reference to FIG. 2, light from the lamp unit 27 is supplied to the detecting section 22 via the optical fiber 21. A plurality of hole-shaped support portions 22a are provided in the detecting section 22, and a cuvette 104 can be inserted into each of the support portions 22a. The end part of the optical fiber 21 is attached to each of the support portions 22a, and the cuvette 104 supported by the support portion 22a can be irradiated with light from the optical fiber 21. The detecting section 22 irradiates the cuvette 104 with light supplied from the lamp unit 27 via the optical fiber 21 and detects the light amount of light to be transmitted through the cuvette 104 (or scattered light from the cuvette 104).

Figure 5A:
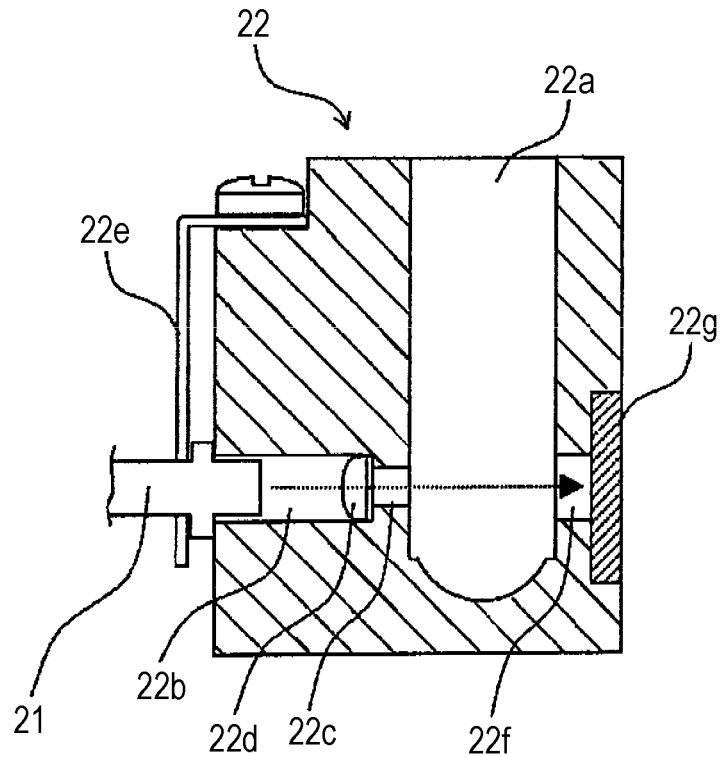
FIG. 5A is a diagram showing the configuration of a detecting section provided in the measurement device.

FIGS. 5A to 5D show an example of one configuration of the plurality of support portions 22a arranged in the detecting section 22, and the other support portions 22a have the same configuration. With reference to FIG. 5A, the detecting section 22 is formed with a circular hole 22b into which the tip of the optical fiber 21 is inserted. The detecting section 22 is further formed with a circular communication hole 22c for communicating the hole 22b with the support portion 22a. The diameter of the hole 22b is larger than the diameter of the communication hole 22c. A lens 22d for condensing light from the optical fiber 21 is arranged at the end of the hole 22b. On the inner wall surface of the support portion 22a, a hole 22f is formed at a position facing the communication hole 22c. A photodetector 22g is arranged at the back of the hole 22f. The photodetector 22g corresponds to a light receiving portion, and outputs an electric signal corresponding to the amount of received light. The light transmitted through the lens 22d is condensed on the light receiving surface of the photodetector 22g, through the communication hole 22c, the support portion 22a, and the hole 22f. The optical fiber 21 is prevented from falling off by a plate spring 22e in a state in which the end part of the optical fiber 21 is inserted into the hole 22b.

Figure 5B:
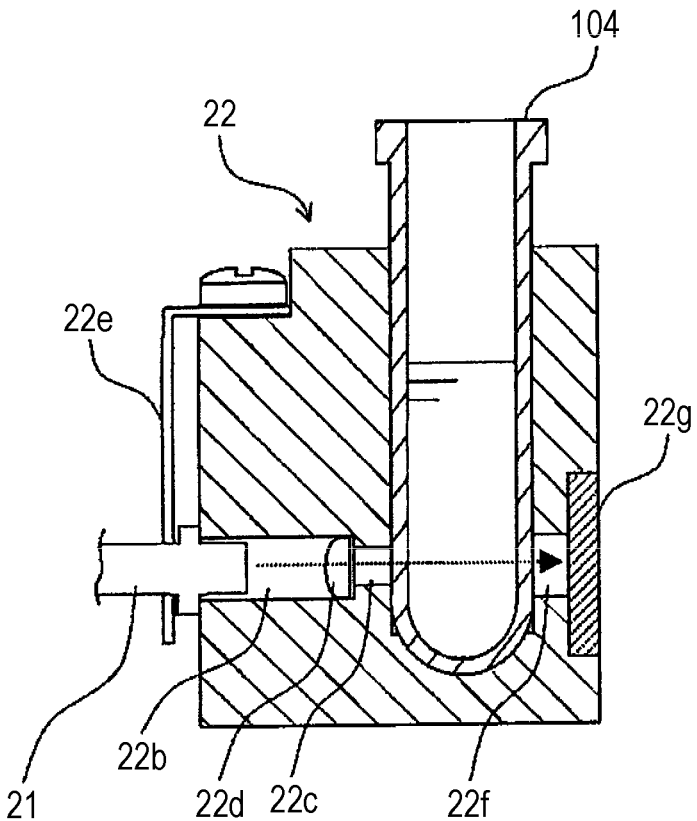
FIG. 5B is a diagram showing the configuration of the detecting section provided in the measurement device.

With reference to FIG. 5B, when the cuvette 104 is supported by the support portion 22a, the light condensed by the lens 22d is transmitted through the cuvette 104 and the sample accommodated in the cuvette 104, and the transmitted light enters the photodetector 22g. As the blood coagulation reaction progresses in the sample, the turbidity of the sample increases. Along with this, the amount of light to be transmitted through the sample (the amount of transmitted light) decreases, and the level of the detection signal of the photodetector 22g decreases.

Figure 5C:
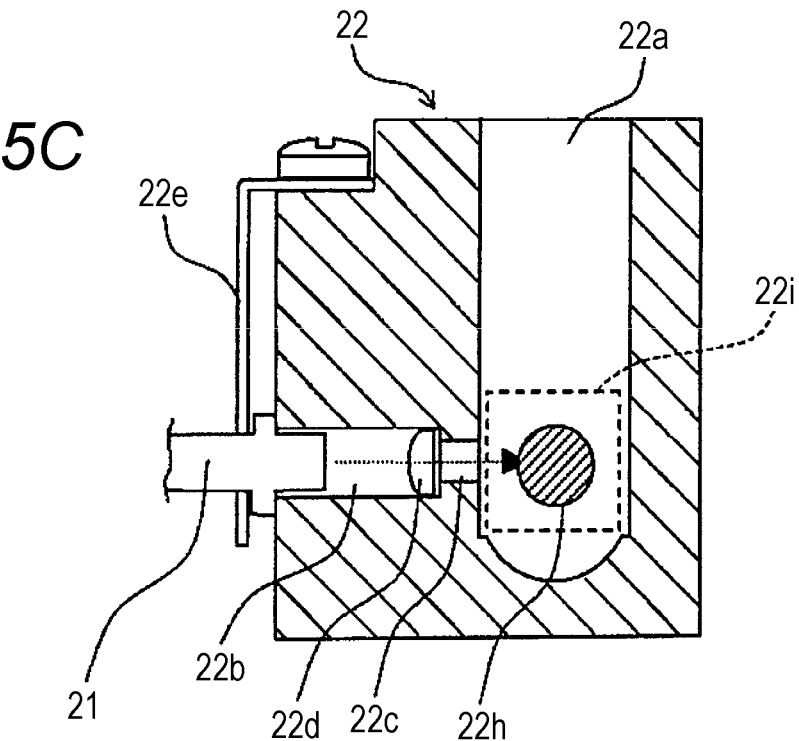
FIG. 5C is a diagram showing the configuration of the detecting section provided in the measurement device.
Figure 5D:
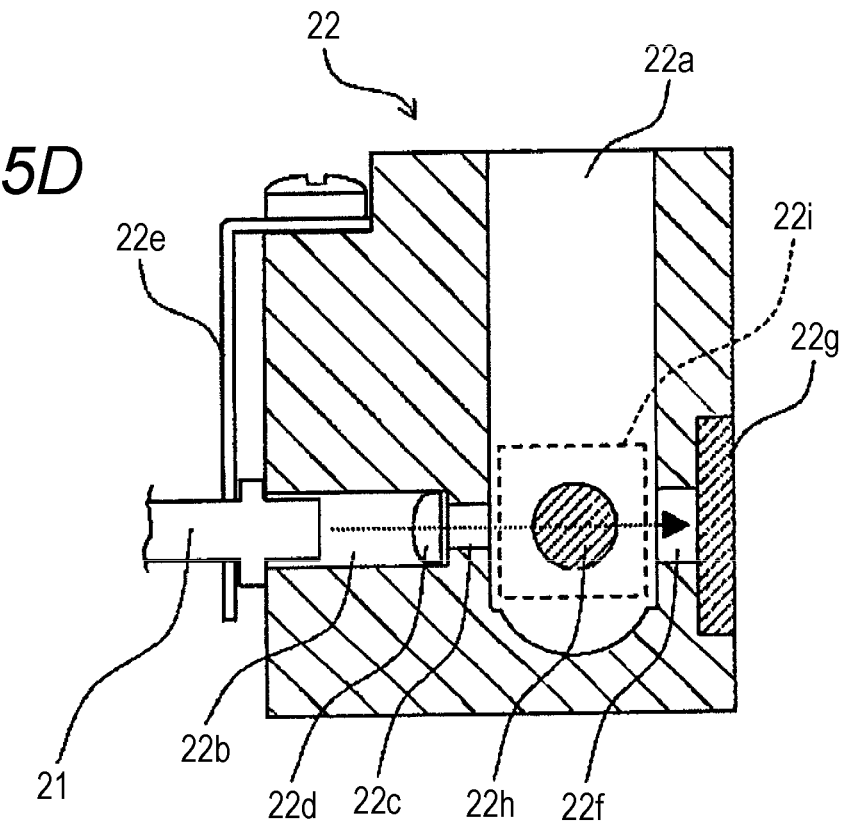
FIG. 5D is a diagram showing the configuration of the detecting section provided in the measurement device.

With reference to FIG. 5C, the configuration of the detecting section 22 in the case of using scattered light will be described. On the inner side surface of the support portion 22a, a hole 22h is provided at a position which is the same height as the communication hole 22c. A photodetector 22i is arranged at the back of the hole 22h. When the cuvette 104 is inserted into the support portion 22a and light is emitted from the optical fiber 21, the light scattered by the measurement sample in the cuvette 104 is irradiated to the photodetector 22i via the hole 22h. In this example, the detection signal from the photodetector 22i indicates the intensity of scattered light by the measurement sample. As shown in FIG. 5D, both the light to be transmitted through the measurement sample and the light to be scattered by the measurement sample may be detected.

As described above, the detecting section 22 irradiates the cuvette 104 with light supplied from the lamp unit 27. The detecting section 22 acquires optical information from the measurement sample. The acquired optical information is transmitted to the control device 40. The control device 40 performs analysis based on the optical information and displays the analysis result on a display unit 41.

After completion of the measurement, the cuvette 104 that has become unnecessary is transported by the cuvette table 13. The transported cuvette 104 is discarded to the disposal port 25 by the catcher 16. During the measurement operation, the piercer 17a and the pipette 18a are appropriately washed with a liquid such as a cleaning liquid supplied from the fluid section 26.

Figure 3:
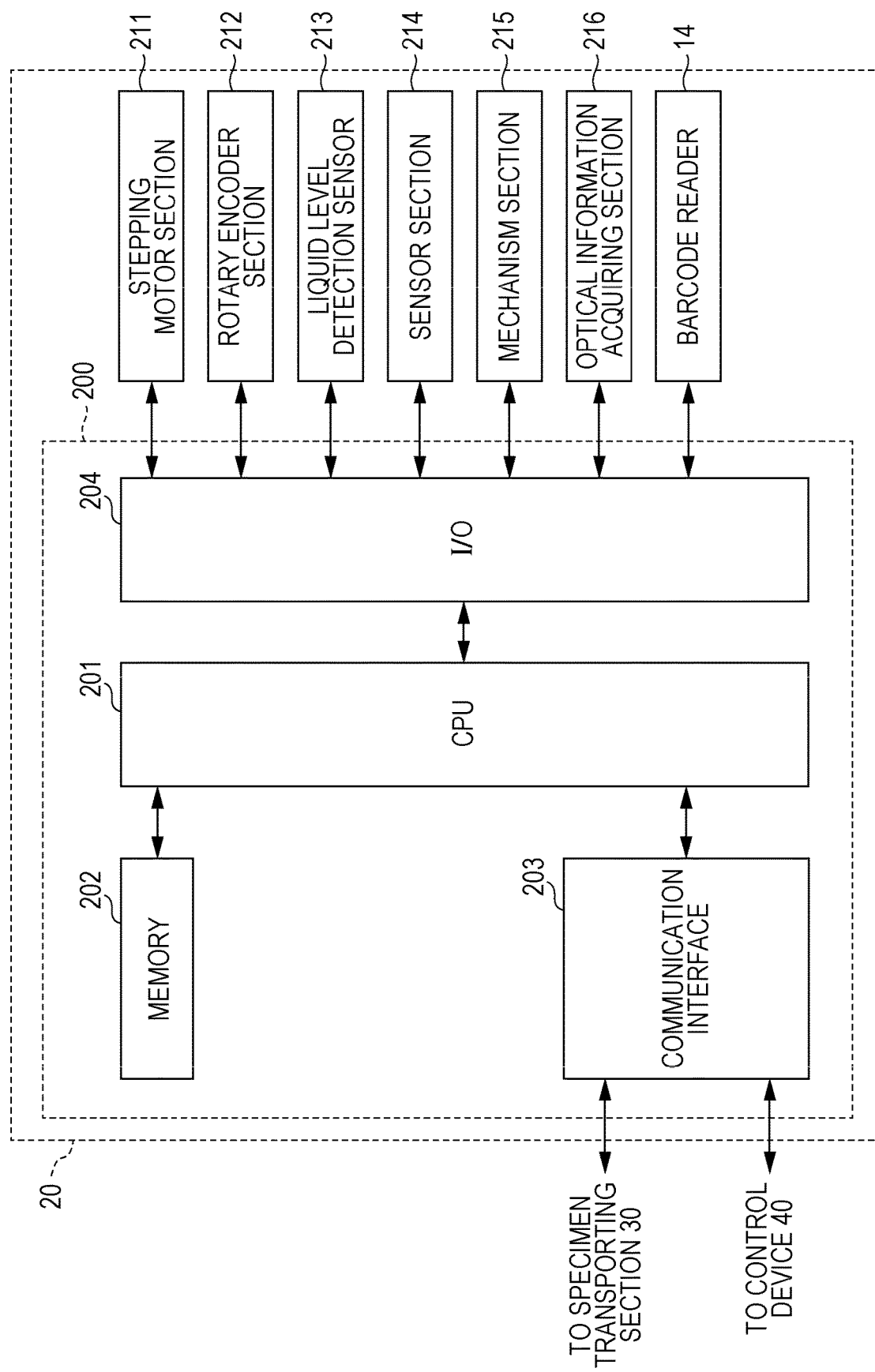
FIG. 3 is a diagram showing the configuration of the measurement unit of the blood specimen analyzer.

The hardware configuration of the measurement device will be described below. As shown in FIG. 3, the measurement unit 20 includes a control section 200, a stepping motor section 211, a rotary encoder section 212, a liquid level detection sensor 213, a sensor section 214, a mechanism section 215, an optical information acquiring section 216, and a barcode reader 14.

With reference to FIG. 3, the control section 200 includes a CPU 201, a memory 202, a communication interface 203, and an I/O interface 204. The CPU 201 executes a computer program stored in the memory 202. The memory 202 is composed of a ROM, a RAM, a hard disk, and the like. The CPU 201 drives the specimen transporting unit 30 via the communication interface 203, and also transmits and receives instruction signals and data with the control device 40. The CPU 201 controls each section in the measurement unit 20 via the I/O interface 204, and also receives signals outputted from each section.

The stepping motor section 211 includes stepping motors for driving the reagent tables 11 and 12, the cuvette table 13, the catcher 16, the specimen dispensing arm 17, the reagent dispensing arm 18, and the cuvette transfer section 23, respectively. The rotary encoder section 212 includes a rotary encoder that outputs a pulse signal corresponding to the amount of rotational displacement of each stepping motor included in the stepping motor unit 211.

The liquid level detection sensor 213 is connected to the pipette 18a provided at the tip of the reagent dispensing arm 18. The liquid level detection sensor 213 detects that the lower end of the pipette 18a has come into contact with the liquid level of the reagent. The sensor section 214 includes a sensor for detecting that the vertical position of the pipette 18a is positioned at the origin position and a sensor for detecting that the power button 20d is pressed. The mechanism section 215 includes a mechanism for driving the cuvette supply section 15, the urgent specimen setting section 19, the warming section 24 and the fluid section 26, and an air pressure source which supplies pressure to the piercer 17a and the pipette 18a so that dispensing operation by the piercer 17a and the pipette 18a can be performed. With reference to FIG. 2, the optical information acquiring section 216 includes at least the lamp unit 27, the optical fiber 21, and the detecting section 22.

The configuration of the control device 40 will be described below. As shown in FIG. 1, the control device 40 includes the display unit 41, an input unit 42, and a computer body 43. The control device 40 receives optical information from the measurement unit 20. Moreover, the processor of the control device 40 calculates first coagulation time and second coagulation time based on the optical information. The processor of the control device 40 calculates a value related to the product of the first coagulation time and the second coagulation time and a value related to the ratio of the first coagulation time and the second coagulation time as values based on the calculated first and second coagulation times. Also, the processor of the control device 40 executes a computer program for analyzing a blood specimen. The control device 40 also functions as a device for determining a blood specimen.

In the case of performing analysis using plural kinds of coagulation time measurement reagents with different phospholipid concentrations, the processor of the control device 40 further calculates the third coagulation time and the fourth coagulation time based on the optical information. The processor of the control device 40 calculates a value related to the product of the third coagulation time and the fourth coagulation time and the value related to the ratio of the third coagulation time and the fourth coagulation time as a value, based on the calculated third and fourth coagulation times. Further, the processor of the control device 40 calculates the above-described value of the index, based on these calculated values. Alternatively, in the case where the method according to the third aspect is performed by the device of this embodiment, the processor of the control device 40 may calculate the ratio of the second coagulation time and the fourth coagulation time as a value based on the second and fourth coagulation times. The value related to the product, the value related to the ratio and the value related to the index are also hereinafter collectively referred to as parameters.

Figure 6:
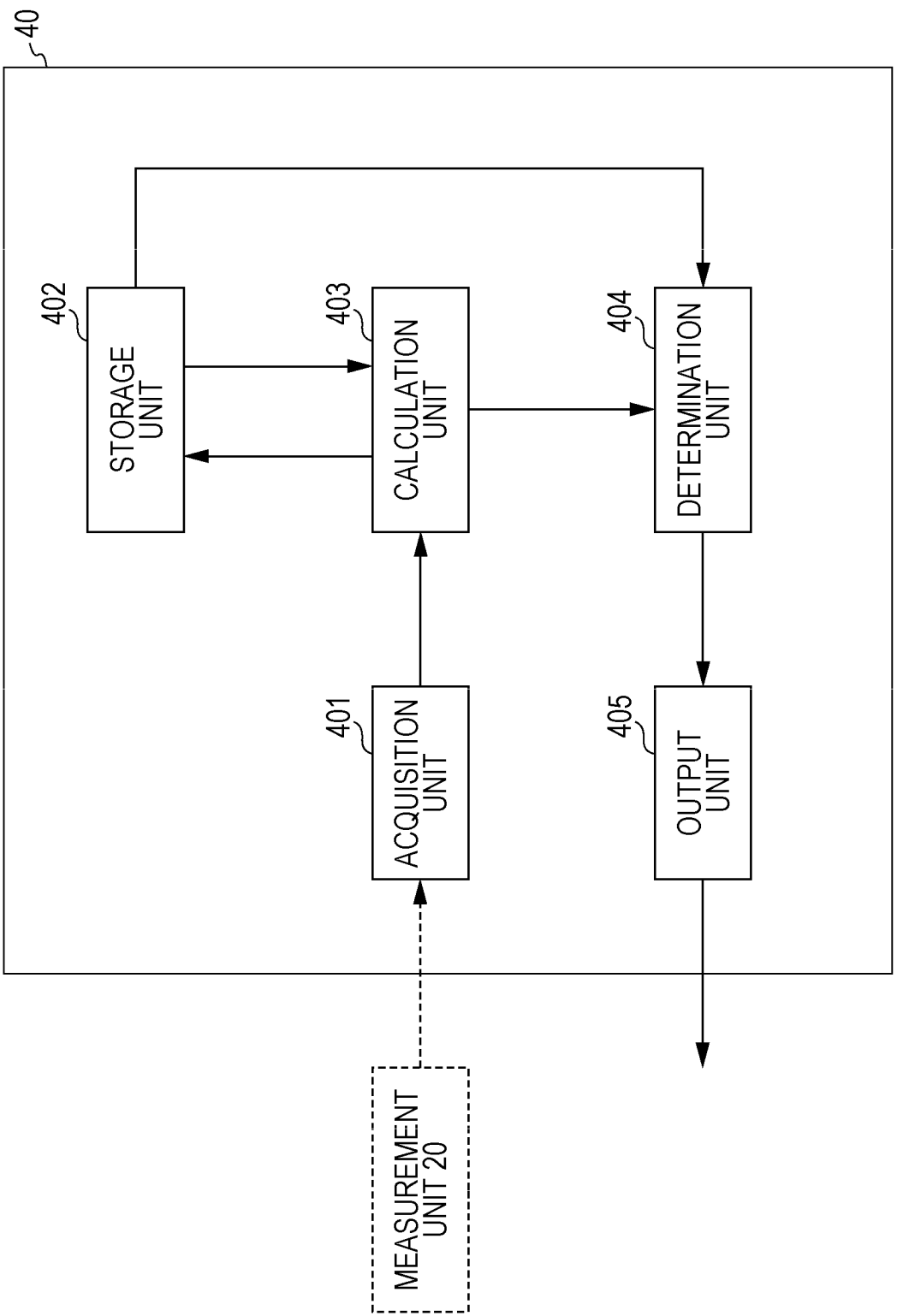
FIG. 6 is a diagram showing the functional configuration of a control device of the blood specimen analyzer.

As to the functional configuration of the control device 40, as shown in FIG. 6, the control device 40 includes an acquisition unit 401, a storage unit 402, a calculation unit 403, a determination unit 404, and an output unit 405. The acquisition unit 401 is communicably connected to the measurement unit 20 via a network. The output unit 405 is communicably connected to the display unit 41.

The acquisition unit 401 acquires the optical information transmitted from the measurement unit 20. The storage unit 402 stores an equation for calculating coagulation time from the optical information, an equation for calculating the above parameters, and the like. The storage unit 402 may store threshold values corresponding to various parameters. Using the information acquired by the acquisition unit 401, the calculation unit 403 calculates the various parameters, according to the equation stored in the storage unit 402. The determination unit 404 determines whether or not the values of the parameters calculated by the calculation unit 403 are smaller than the predetermined threshold values stored in the storage unit 402. The output unit 405 outputs the parameters calculated by the calculation unit 403 as reference information regarding the blood specimen.

Figure 7:
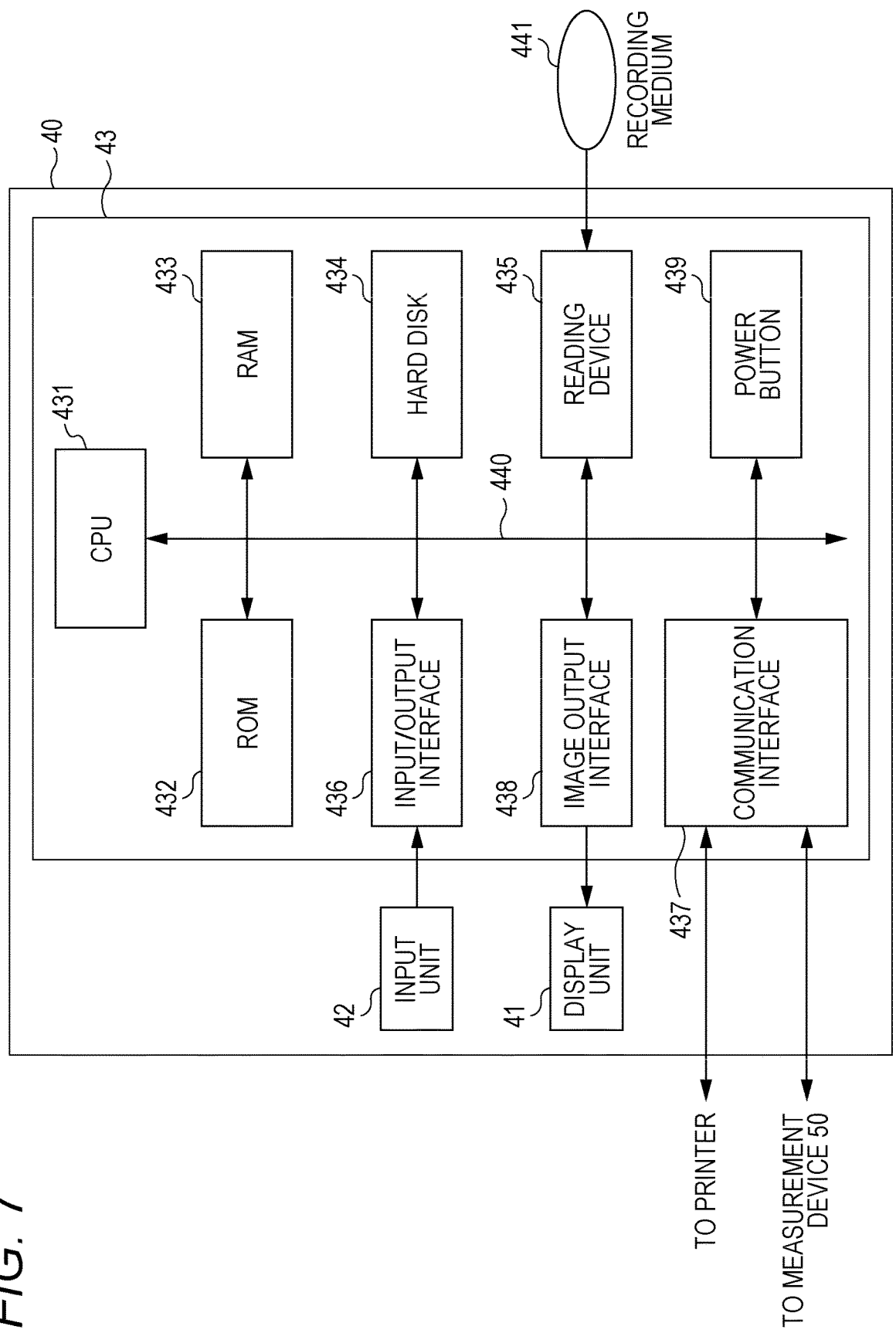
FIG. 7 is a diagram showing the hardware configuration of the control device of the blood specimen analyzer.

As shown in FIG. 7, the computer body 43 of the control device 40 includes a CPU 431, a ROM 432, a RAM 433, a hard disk 434, a readout device 435, an input/output interface 436, a communication interface 437, an image output interface 438, and a power button 439. The CPU 431, the ROM 432, the RAM 433, the hard disk 434, the reading device 435, the input/output interface 436, the communication interface 437, the image output interface 438, and the power button 439 are communicably connected by a bus 440.

The CPU 431 executes a computer program stored in the ROM 432 and a computer program loaded in the RAM 433. Each of the above-described functional blocks is realized by the CPU 431 executing an application program. Thus, the computer system functions as a terminal of the device for determining a blood specimen.

The ROM 432 includes a mask ROM, PROM, EPROM, EEPROM, and the like. In the ROM 432, a computer program executed by the CPU 431 and data used for the computer program are recorded.

The RAM 433 includes SRAM, DRAM, and the like. The RAM 433 is used for reading the computer program recorded in the ROM 432 and the hard disk 434. The RAM 433 is also used as a work area of the CPU 431 when executing these computer programs.

The hard disk 434 has installed therein an operating system, a computer program such as an application program (a computer program for analyzing a blood specimen) to be executed by the CPU 431, data used for executing the computer program, and setting contents of the control device 40.

The reading device 435 includes a flexible disk drive, a CD-ROM drive, a DVD-ROM drive, and the like. The reading device 435 can read a computer program or data recorded on a portable recording medium 441 such as a CD or a DVD.

The input/output interface 436 includes, for example, a serial interface such as USB, IEEE1394 or RS-232C, a parallel interface such as SCSI, IDE or IEEE1284, and an analog interface including a D/A converter, an A/D converter and the like. The input unit 42 such as a keyboard and a mouse is connected to the input/output interface 436. The user inputs an instruction via the input unit 42, and the input/output interface 436 receives a signal inputted via the input unit 42.

The communication interface 437 is, for example, an Ethernet (registered trademark) interface or the like. The control device 40 can transmit print data to a printer through the communication interface 437. The communication interface 437 is connected to the measurement unit 20, and the CPU 431 transmits and receives an instruction signal and data with the measurement unit 20 via the communication interface 437.

The image output interface 438 is connected to the display unit 41 including an LCD, a CRT, and the like. The image output interface 438 outputs a video signal corresponding to image data to the display unit 41, and the display unit 41 displays an image based on the video signal outputted from the image output interface 438.

With reference to FIG. 3, during the measurement operation, the CPU 201 of the measurement unit 20 temporarily stores in the memory 202 the data (optical information) obtained by digitizing the detection signal outputted from the detecting section 22 (see FIG. 2). The storage area of the memory 202 is divided into areas for each support portion 22a. In each area, the data (optical information) which are acquired when the cuvette 104 supported by the corresponding support portion 22a is irradiated with light having a predetermined wavelength are sequentially stored. Thus, the data are sequentially stored in the memory 202 over a predetermined measurement time. When the measurement time elapses, the CPU 201 stops storing the data in the memory 202, and transmits the stored data to the control device 40 via the communication interface 203. The control device 40 processes and analyzes the received data, and displays the analysis result on the display unit 41.

Figure 8A:
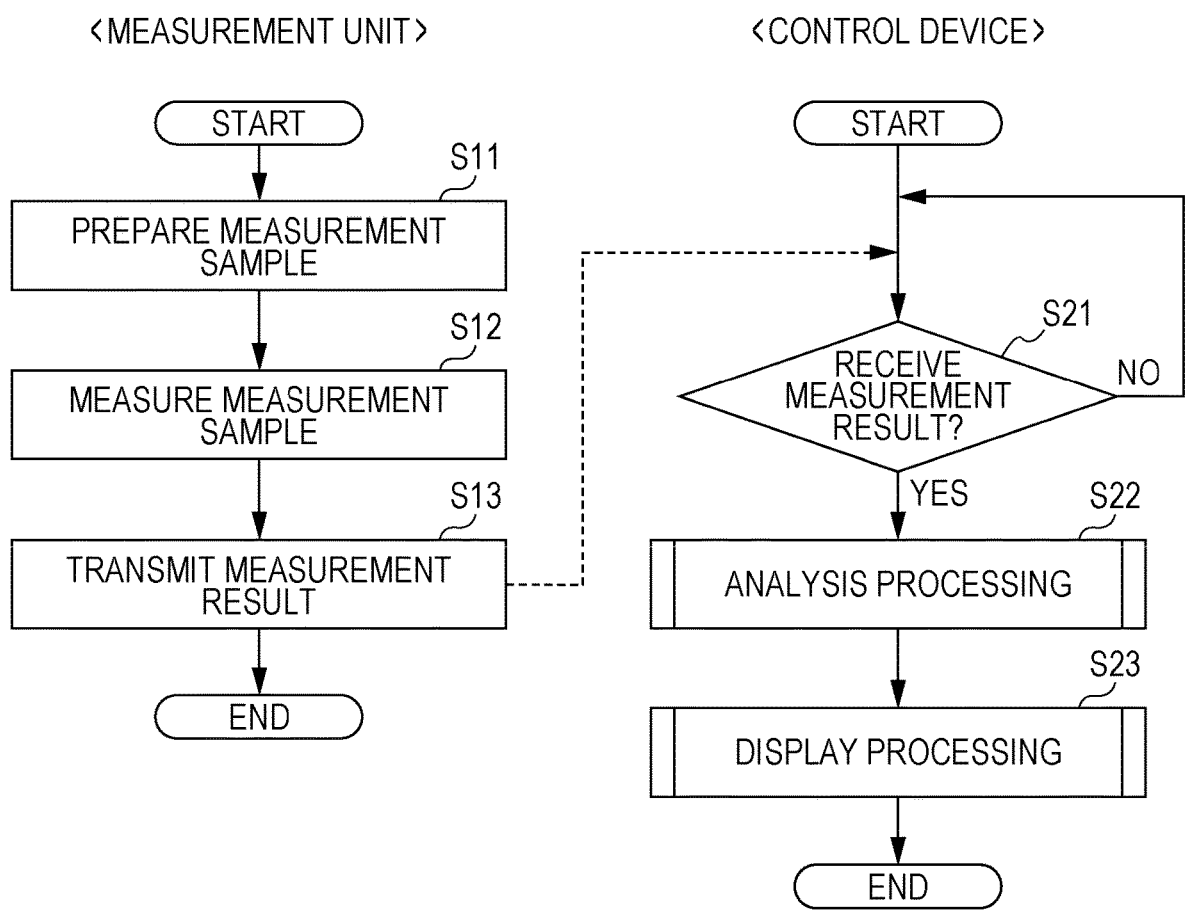
FIG. 8A is a flowchart showing measurement processing of a blood specimen by the blood specimen analyzer.

The processing in the measurement unit 20 is mainly performed under the control of the CPU 201 of the measurement unit 20, and the processing in the control device 40 is mainly performed under the control of the CPU 431 of the control device 40. However, this embodiment is not limited to this example. The processing in the measurement unit 20 may be performed under the control of the CPU 431 of the control device 40. With reference to FIG. 8A, when the measurement processing is started, the measurement unit 20 aspirates a predetermined amount of a blood specimen from the specimen container 101 transported by the specimen transporting section, and the measurement unit 20 dispenses the aspirated blood specimen into an empty cuvette 104 on the cuvette table 13. Also, the measurement unit 20 aspirates a predetermined amount of the blood specimen from the reagent container 103 accommodating the blood specimen. The measurement unit 20 dispenses it into an empty cuvette 104. Moreover, the measurement unit 20 aspirates a predetermined amount of a preparation reagent from the reagent container 103 accommodating the preparation reagent (normal plasma or a metal ion-containing aqueous solution). The measurement unit 20 dispenses it into the cuvette 104 containing the blood specimen. The measurement unit 20 stirs the mixture to prepare a mixed specimen.

Subsequently, the measurement unit 20 transfers the cuvette 104 containing each of the blood specimen and the mixed specimen to the warming unit 24. The measurement unit 20 warms the specimen in the cuvette 104 to a predetermined temperature (for example, 37° C.). Then, the measurement unit 20 adds a first coagulation time measurement reagent (first partial reagent and second partial reagent) to the cuvette 104 containing the blood specimen to prepare a first measurement sample. In addition, the measurement unit 20 adds a second coagulation time measurement reagent (first partial reagent and third partial reagent) to the cuvette 104 containing the mixed specimen to prepare a second measurement sample (step S11). In the case of making a determination using plural kinds of coagulation time measurement reagents with different phospholipid concentrations, the measurement unit 20 adds a third coagulation time measurement reagent (first partial reagent and second partial reagent) to the cuvette 104 containing the blood specimen to prepare a third measurement sample. In addition, the measurement unit 20 adds a fourth coagulation time measurement reagent (first partial reagent and third partial reagent) to the cuvette 104 containing the mixed specimen to prepare a fourth measurement sample. The measurement unit 20 starts measurement of coagulation time from the time when the partial reagent containing the aqueous calcium chloride solution is added to the cuvette 104. In the case where all of the coagulation time measurement reagents are one-liquid type reagents containing calcium ions or snake venom, measurement of coagulation time is started from the time when the reagent is added. Thereafter, the measurement unit 20 transfers the cuvette 104 to which the reagent is added to the detecting section 22, and irradiates the cuvette 104 with light to measure the measurement sample (step S12). In this measurement, data (the amount of scattered light or the amount of transmitted light) based on the light with a wavelength of 660 nm is sequentially stored in the memory 202 during the measurement time. At this time, the data is stored in the memory 202 in a state associated with the elapsed time from the reagent addition time point. Then, when the measurement time elapses, the measurement unit 20 stops the measurement, and the measurement unit 20 transmits the measurement result (data) stored in the memory 202 to the control device 40 (step S13).

When the control device 40 receives the measurement result (data) from the measurement unit 20 (step S21: YES), the control device 40 executes analysis processing on the received measurement result (step S22). That is, the control device 40 calculates various parameters from the coagulation time of each measurement sample. After performing the analysis processing, the control device 40 executes display processing of the analysis result (step S23).

Figure 8B:
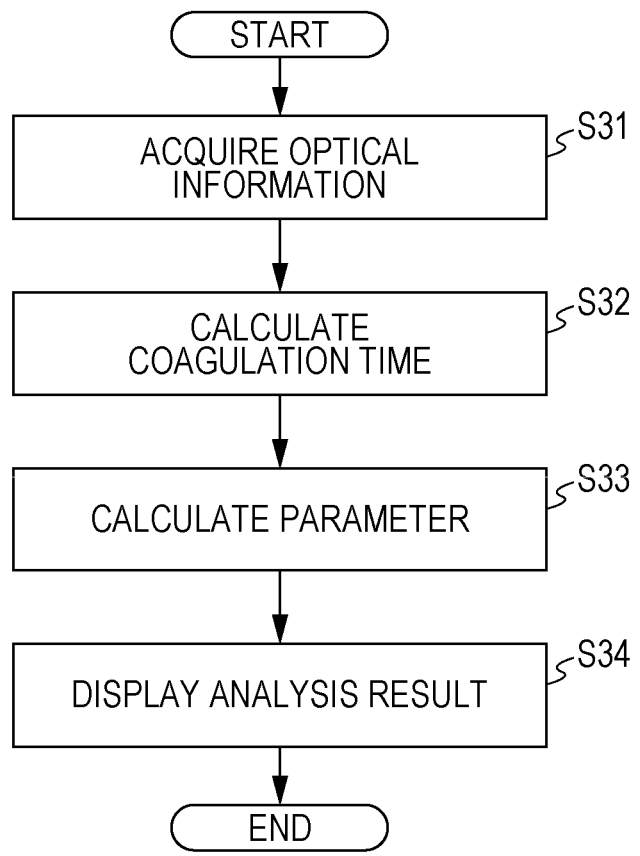
FIG. 8B is a flowchart showing a procedure of analysis processing of measurement data and display processing of analysis result.

The above analysis processing and display processing will be described with reference to FIG. 8B. In step S31, the acquisition unit 401 of the control device 40 acquires optical information (scattered light intensity, or transmittance or absorbance), based on the data (the amount of scattered light or the amount of transmitted light) received from the measurement unit 20. In step S32, the calculation unit 403 calculates first and second coagulation times, from the optical information acquired by the acquisition unit 401, according to the equation for calculating the coagulation time stored in the storage unit 402. The calculation unit 403 stores the calculated values in the storage unit 402. In the case of using the third and fourth coagulation time measurement reagents, the calculation unit 403 further calculates the third and fourth coagulation times, and the calculation unit 403 stores the calculated values in the storage unit 402. In step S33, the calculation unit 403 calculates the parameters, from the values of the coagulation times stored in the storage unit 402, according to the equation for calculating the parameters stored in the storage unit 402. The calculation unit 403 stores the calculated values in the storage unit 402. In step S34, the output unit 405 displays at least the values of the parameters on the display unit 41 as the analysis result. The output unit 405 may further display the coagulation time of each measurement sample on the display unit 41.

Figure 9A:
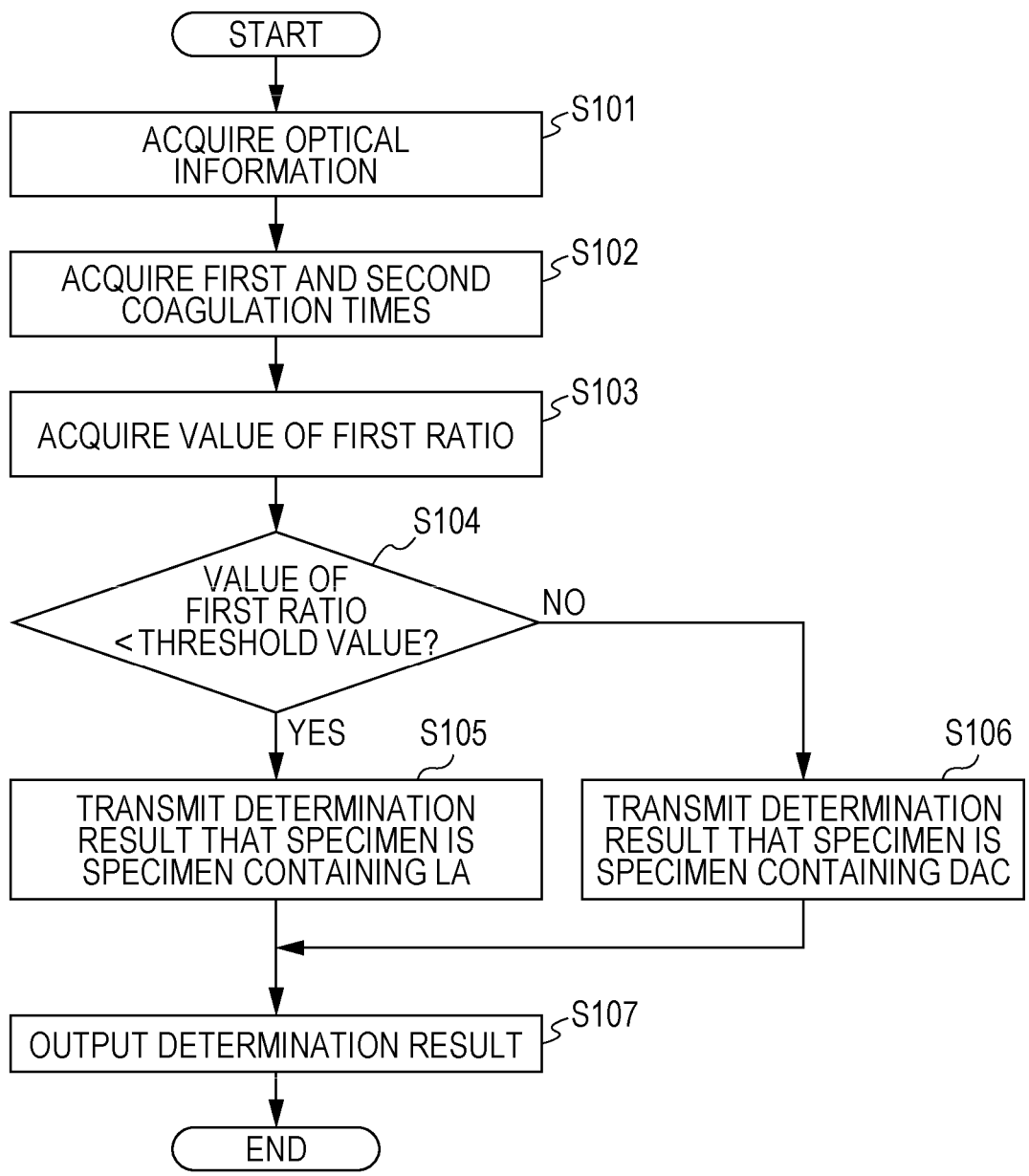
FIG. 9A is a flowchart showing analysis processing of a blood specimen by the blood specimen analyzer.

The device of this embodiment determines whether the blood specimen of a subject is a blood specimen containing LA or a blood specimen containing DAC based on the acquired parameters. The device of this embodiment may output the determination result as reference information. With reference to FIG. 9A, the flow of determination by the control device will be described below. FIG. 9A shows a flow of processing in the case of determining the blood specimen from the results of measurement using the first and second coagulation time measurement reagents, and a zinc ion as a preparation reagent. Here, the case of determining the blood specimen by acquiring the value of the ratio of the first coagulation time and the second coagulation time calculated by equation (2) above, as a parameter, and comparing the acquired value with a corresponding predetermined threshold value, will be described as an example. However, this embodiment is not limited only to this example. With reference to the description of the method of this embodiment, the kinds of preparation reagent and parameters, and the steps related to the determination to be described later can be appropriately changed.

In step S101, the acquisition unit 401 of the control device 40 acquires optical information (scattered light intensity, transmittance or absorbance) based on the data (the amount of scattered light or the amount of transmitted light) received from the measurement unit 20. In step S102, the calculation unit 403 calculates first and second coagulation times, from the optical information acquired by the acquisition unit 401, according to the equation for calculating the coagulation time stored in the storage unit 402. In step S103, the calculation unit 403 calculates a value of the ratio of the first coagulation time and the second coagulation time, from the calculated first and second coagulation times, according to the equation (2) stored in the storage unit 402. In FIG. 9A, the "FIRST RATIO" refers to the ratio of the first coagulation time and the second coagulation time.

In step S104, using the value of the ratio calculated in the calculation unit 403 and the predetermined threshold value stored in the storage unit 402, the determination unit 404 determines whether the blood specimen of a subject is a specimen containing LA or a specimen containing DAC. Here, when the value of the ratio is lower than the predetermined threshold value, the process proceeds to step S105. In step S105, the determination unit 404 transmits to the output unit 405 a determination result that the blood specimen of a subject is a specimen containing LA. When the value of the ratio is not lower than the predetermined threshold value (that is, the value of the ratio is higher than the predetermined threshold value or is equal to the predetermined threshold value), the process proceeds to step S106. In step S105, the determination unit 404 transmits to the output unit 405 a determination result that the blood specimen of a subject is a specimen containing DAC.

In step S107, the output unit 405 outputs the determination result, and the output unit 405 displays the determination result on the display unit 41, or the output unit 405 makes a printer to print the determination result. Alternatively, the determination result may be outputted by voice. Thus, the determination result can be provided to a user as reference information on the blood specimen of a subject.

Figure 9B:
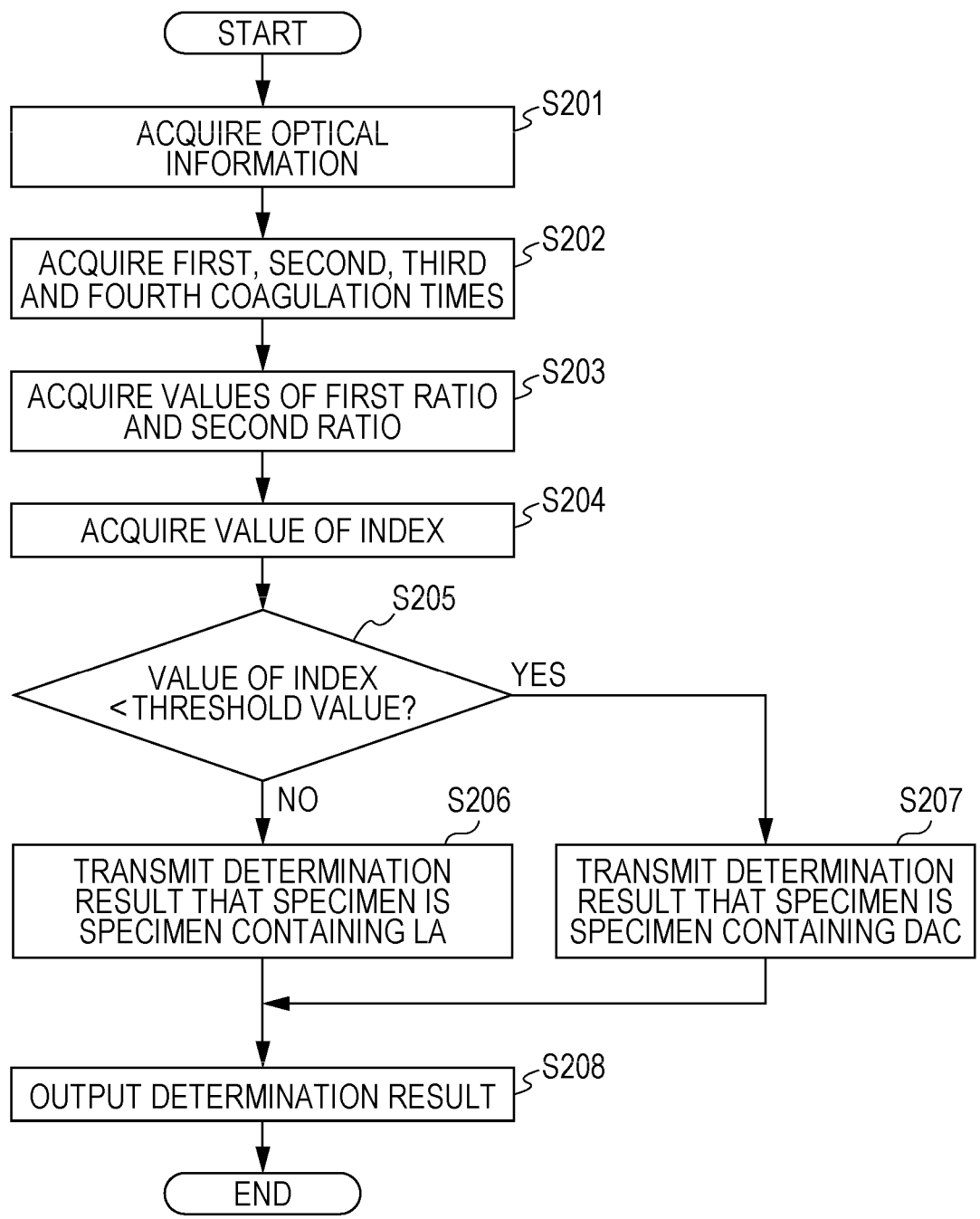
FIG. 9B is a flowchart showing analysis processing of a blood specimen by the blood specimen analyzer.

With reference to FIG. 9B, the flow of processing in the case of determining the blood specimen from the results of measurement using the first, second, third and fourth coagulation time measurement reagents, and a zinc ion as a preparation reagent is shown. Here, the case of determining the blood specimen by acquiring the value of the index calculated by equation (4) above, as a parameter, and comparing the acquired value with a corresponding predetermined threshold value, will be described as an example. However, this embodiment is not limited only to this example. With reference to the description of the method of this embodiment, the kinds of preparation reagent and parameters, and the steps related to the determination to be described later can be appropriately changed.

In step S201, the acquisition unit 401 of the control device 40 acquires optical information based on the data received from the measurement unit 20. In step S202, the calculation unit 403 calculates first, second, third, and fourth coagulation times, from the optical information acquired by the acquisition unit 401, according to the equation for calculating the coagulation time stored in the storage unit 402. In step S203, the calculation unit 403 calculates a value of the ratio of the first coagulation time and the second coagulation time and a value of the ratio of the third coagulation time and the fourth coagulation time, from the calculated coagulation times, according to equations (3) and (3') stored in the storage unit 402. In FIG. 9B, the "FIRST RATIO" refers to the ratio of the first coagulation time and the second coagulation time, and the "SECOND RATIO" refers to the ratio of the third coagulation time and the fourth coagulation time.

In step S204, the calculation unit 403 calculates the value of the index from these ratios, according to equation (4) stored in the storage unit 402.

In step S205, using the value of the index calculated in the calculation unit 403 and the predetermined threshold value stored in the storage unit 402, the determination unit 404 determines whether the blood specimen of a subject is a specimen containing LA or a specimen containing DAC. Here, when the value of the index is not lower than the predetermined threshold value (that is, the value of the ratio is higher than the predetermined threshold value or is equal to the predetermined threshold value), the process proceeds to step S206. In step S206, the determination unit 404 transmits to the output unit 405 a determination result that the blood specimen of a subject is a specimen containing LA. When the value of the ratio is lower than the predetermined threshold value, the process proceeds to step S207. In step S207, the determination unit 404 transmits to the output unit 405 a determination result that the blood specimen of a subject is a specimen containing DAC. Details of step S208 are the same as those described for step S107.

Figure 9C:
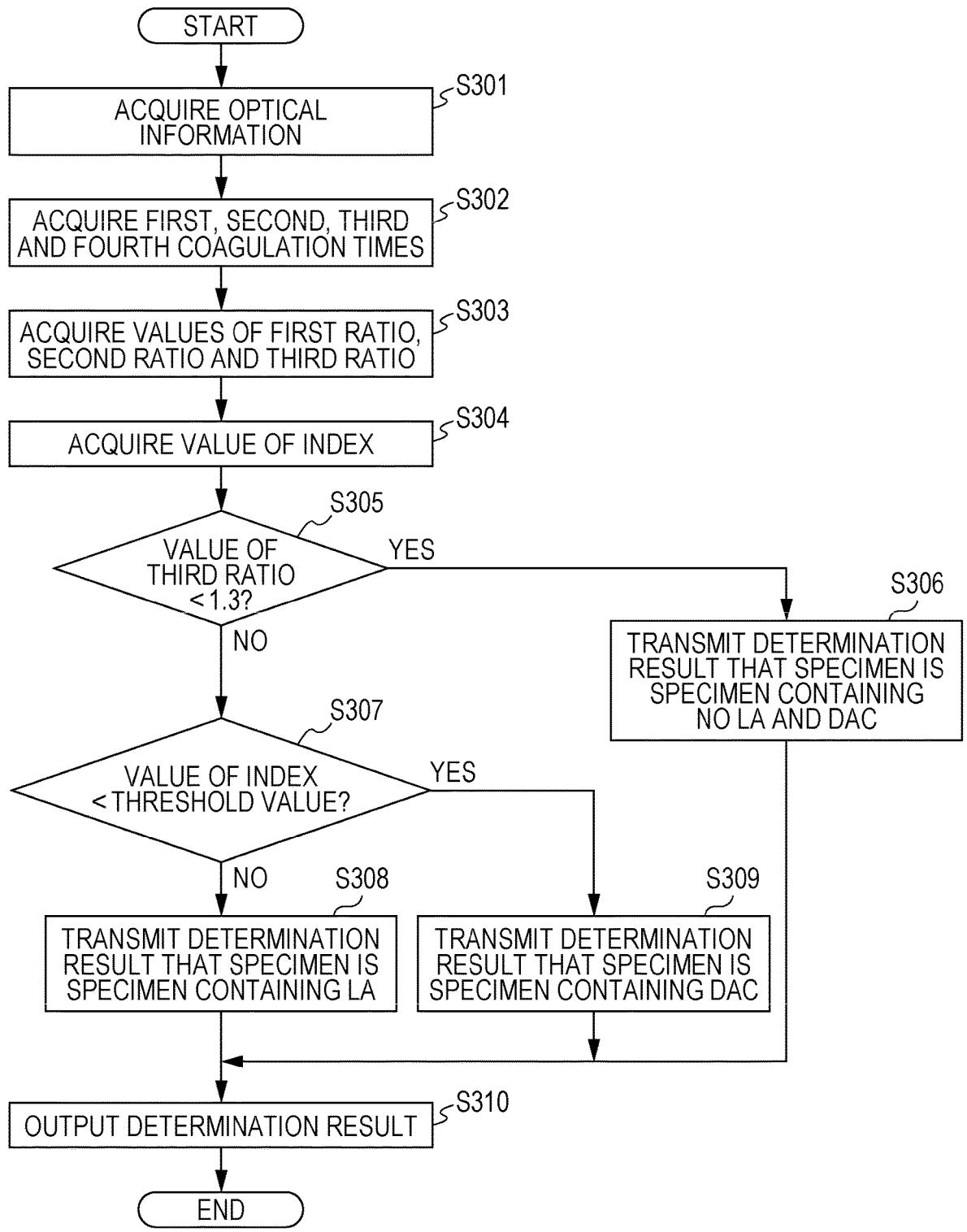
FIG. 9C is a flowchart showing analysis processing of a blood specimen by the blood specimen analyzer.

With reference to FIG. 9C, a flow further including a step of determining a specimen not containing LA and DAC based on the value of the ratio of the first coagulation time and the third coagulation time in the flow shown in FIG. 9B will be described. Here, the case of using the value of the ratio calculated by equation (7) above will be described as an example. However, this embodiment is not limited only to this example. With reference to the description of the method of this embodiment, the kinds of preparation reagent and parameters, and the steps related to the determination to be described later can be appropriately changed.

In step S301, the acquisition unit 401 of the control device 40 acquires optical information based on the data received from the measurement unit 20. In step S302, the calculation unit 403 calculates first, second, third, and fourth coagulation times, from the optical information acquired by the acquisition unit 401, according to the equation for calculating the coagulation time stored in the storage unit 402. In step S303, the calculation unit 403 calculates a value of the ratio of the first coagulation time and the second coagulation time, a value of the ratio of the third coagulation time and the fourth coagulation time, and a value of the ratio of the first coagulation time and the third coagulation time, from the calculated coagulation times, according to equations (3), (3') and (7) stored in the storage unit 402. In FIG. 9C, the "FIRST RATIO" refers to the ratio of the first coagulation time and the second coagulation time, the "SECOND RATIO" refers to the ratio of the third coagulation time and the fourth coagulation time, and the "THIRD RATIO" refers to the ratio of the first coagulation time and the third coagulation time. In step S304, the calculation unit 403 calculates a value of the index from the value of the ratio of the first coagulation time and the second coagulation time and the value of the ratio of the third coagulation time and the fourth coagulation time, according to equation (4) stored in the storage unit 402.

In step S305, the determination unit 404 determines whether the blood specimen of a subject is a specimen containing LA or a specimen containing DAC, using the value of the ratio of the first coagulation time and the third coagulation time calculated by the calculation unit 403 and the predetermined threshold value (1.3) stored in the storage unit 402. Here, when the value of the ratio is lower than 1.3, the process proceeds to step S306. In step S306, the determination unit 404 transmits to the output unit 405 the determination result that the blood specimen of a subject is a specimen not containing LA and DAC. When the value of the ratio is not lower than 1.3 (the value of the ratio is 1.3 or more), the process proceeds to step S307.

In step S307, using the value of the index calculated in the calculation unit 403 and the predetermined threshold value stored in the storage unit 402, the determination unit 404 determines whether the blood specimen of a subject is a specimen containing LA or a specimen containing DAC. Details of steps S307, S308 and S309 are the same as those described for steps S205, S206 and S207, respectively. Then, the determination unit 404 transmits the determination result to the output unit 405. Step S310 is the same as that described for step S107.

As an example of a screen displaying the analysis result, a screen for displaying the result of measuring the first and second coagulation times of each specimen will be described with reference to FIG. 10. On the screen shown in FIG. 10, the rack number and position, the specimen number, the measurement start time and end time, the first coagulation time (LA1 1-1 sec) and the second coagulation time (LA2 1-1 sec) are displayed, but it is not limited to this. In this embodiment, it is preferable to display the parameter calculated from the coagulation time on the screen. A user can use the parameter displayed on the screen to determine whether the blood specimen is an LA specimen or a DAC specimen. In the case of determining the blood specimen with the device of this embodiment, the determination result may be displayed with text such as "suspected of containing LA" or "suspected of containing DAC" on the screen. The determination result may be displayed with a symbol such as a flag or a graphic mark. Alternatively, the determination result may be outputted by voice. It is desirable that determination of a blood specimen is made with consideration of not only the determination result by the device of this embodiment but also information such as other inspection results. Accordingly, it may be displayed as "(Reference)" to indicate that the determination result by the device of this embodiment and the predetermined threshold value are reference information.

Hereinafter, the present invention will be described in detail by examples, but the present invention is not limited to these examples.

EXAMPLES

Example 1

Using normal plasma as a preparation reagent, whether discrimination between blood specimens containing LA and blood specimens containing DAC was possible was studied.
(1) Reagents and Specimens
(1.1) Coagulation Time Measurement Reagent LA1 Screening Reagent (Lot No. 549855AA, Siemens K.K.: hereinafter referred to as "first reagent") and LA2 Confirm Reagent (Lot No. 548732A, Siemens K.K.: hereinafter referred to as "second reagent") were used as coagulation time measurement reagents. The first reagent is a reagent for detecting LA based on dRVVT measurement and includes Russell viper venom and phospholipids. The second reagent contains Russell viper venom and contains phospholipid at a concentration higher than that of the first reagent.
(1.2) Preparation Reagent Control N (Lot No. 503197 A: Siemens K.K.), normal plasma, was used as a preparation reagent.

(1.3) Blood Specimen

LA-containing plasma (13 samples) shown in Table 1 below was used as a blood specimen containing LA. As a blood specimen containing DAC, rivaroxaban-containing plasma (10 specimens: hereinafter also referred to as "DAC-containing plasma") shown in Table 2 below was used.

TABLE 1

| Product name | Supplier | Lot No. |
|---|---|---|
| LA Control 1 Low | Siemens K. K. | 546061B |
| | | 546060B |
| | | 546064A |
| | | 546065A |
| | | 546066A |
| LA Control 2 High | Siemens K. K. | 545932BA |
| | | 545936A |
| | | 545937B |
| LA weak positive | PBI Inc. | WL-022 |
| | | WL-023 |
| | | WL-024 |
| LA positive | PBI Inc. | 6247 |
| | | 6248 |

TABLE 2

| Product name | Supplier | Lot No. |
|---|---|---|
| Rivaroxaban Control Plasma 1 | HBM Inc. | 43202-1 |
| | | 43604-1 |
| Rivaroxaban Control Plasma 2 | HBM Inc. | 43202-2 |
| | | 43604-2 |
| Rivaroxaban Calibrator Plasma 2 | HBM Inc. | 42201-2 |
| Rivaroxaban Calibrator Plasma 3 | HBM Inc. | 42201-3 |
| Rivaroxaban Low Control Plasma 1 | HBM Inc. | 42203-1 |
| Rivaroxaban Low Control Plasma 2 | HBM Inc. | 42203-2 |
| Rivaroxaban Low Calibrator Plasma 2 | HBM Inc. | 44502-2 |
| Rivaroxaban Low Calibrator Plasma 3 | HBM Inc. | 44502-3 |

(2) Measurement of Coagulation Time (2.1) Coagulation Times (First and Third Coagulation Times) of Measurement Samples not Containing Preparation Reagent Each specimen (100 µL) was warmed at 37° C. for 4 minutes, then the first reagent (100 µL) was mixed, and the first coagulation time was measured. The third coagulation time was measured in the same manner as described above except that the second reagent was used in place of the first reagent. The coagulation time was measured with a fully automated coagulation time measurement device CS-5100 (Sysmex Corporation).

(2.2) Coagulation Times (Second and Fourth Coagulation Times) of Measurement Samples Containing Preparation Reagent A sample prepared by mixing a preparation reagent (50 µL) with each specimen (50 µL) was warmed at 37° C. for 4 minutes, then the first reagent (100 µL) was mixed to the mixture, and the second coagulation time was measured. The fourth coagulation time was measured in the same manner as described above except that the second reagent was used in place of the first reagent. The coagulation time was measured with CS-5100 (Sysmex Corporation).

(3) Acquisition of Parameters

From the coagulation times measured for each specimen, values related to the products or ratios of the coagulation times were acquired according to equations (A) to (G) below. For each parameter, a significant difference between a group of LA-containing plasma (hereinafter also referred to as "LA group") and a group of DAC-containing plasma (hereinafter also referred to as "DAC group") was tested by t-test.

(Ratio 1)=(First coagulation time)/(Third coagulation time)     Equation (A)

(Ratio 3)=(First coagulation time)/(Second coagulation time)     Equation (B)

(Ratio 4)=(Third coagulation time)/(Fourth coagulation time)     Equation (C)

(Product 1)=(First coagulation time)×(Second coagulation time)     Equation (D)

(Product 2)=(Third coagulation time)×(Fourth coagulation time)     Equation (E)

(Index 1)=(Ratio 2)/(Ratio 1)     Equation (F)

(Index 2)=[(Second coagulation time)/(First coagulation time)]×[(Fourth coagulation time)/(Third coagulation time)]     Equation (G)

(4) Results

As an example of measurement results, the coagulation time and parameters of some specimens are shown in Table 3. As an example of the distribution of each parameter, Ratio 1, Ratio 3, Ratio 4, Product 1, Product 2 and Index 2 in the LA group and the DAC group are shown in FIGS. 11A, 11B, 11C, 11D, 11E and 11F, respectively.

TABLE 3

| Blood specimen (Lot No.) | LA-Containing plasma (545936A) | DAC-Containing plasma (43202-2) |
|---|---|---|
| First coagulation time (sec.) | 78.4 | 166.2 |
| Second coagulation time (sec.) | 57.8 | 88.6 |
| Third coagulation time (sec.) | 38.4 | 84.0 |
| Fourth coagulation time (sec.) | 34.7 | 57.2 |
| Ratio 1 | 2.0 | 2.0 |
| Ratio 3 | 1.4 | 1.9 |
| Ratio 4 | 1.1 | 1.5 |
| Product 1 | 4531 | 14725 |
| Product 2 | 1332 | 4804 |
| Index 1 | 0.818 | 0.783 |
| Index 2 | 0.666 | 0.363 |

Figure 11A:
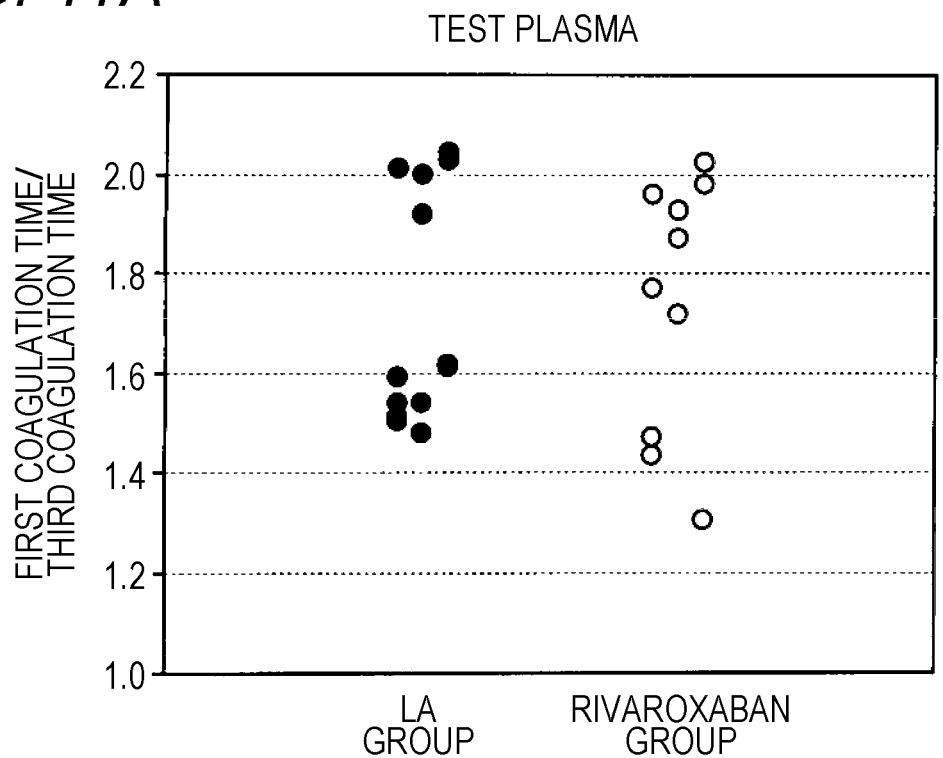
FIG. 11A is a diagram showing distributions of values of Ratio 1 (first coagulation time/third coagulation time) in LA specimens and DAC specimens.

In Example 1, Ratio 1 is the ratio of the coagulation times of the test plasma which are measured using two kinds of coagulation time measurement reagents with different phospholipid concentrations. As shown in FIG. 11A, it can be seen that the LA group and the DAC group cannot be discriminated by Ratio 1. Although not shown, Index 1 could not discriminate the LA group and the DAC group as Ratio 1.

Ratio 1 cannot be used for discrimination between the LA group and the DAC group, but Ratio 1 can be used as a parameter for selecting a specimen with prolonged coagulation time. As shown in FIG. 11A, Ratio 1 is 1.3 or more in both the LA group and the DAC group. In a blood specimen derived from a healthy subject, Ratio 1 is approximately 1.0, so that a specimen whose Ratio 1 is 1.3 or more can be selected as a determination target.

Figure 11B:
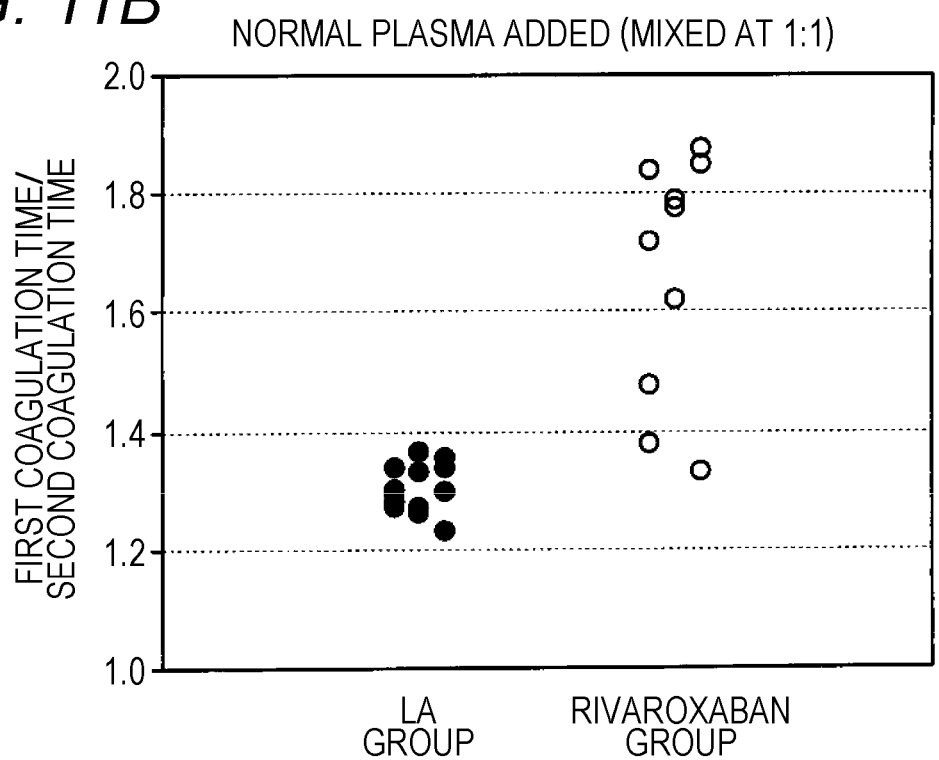
FIG. 11B is a diagram showing distributions of values of Ratio 3 (first coagulation time/second coagulation time) in LA specimens and DAC specimens when normal plasma is used as a preparation reagent.
Figure 11C:
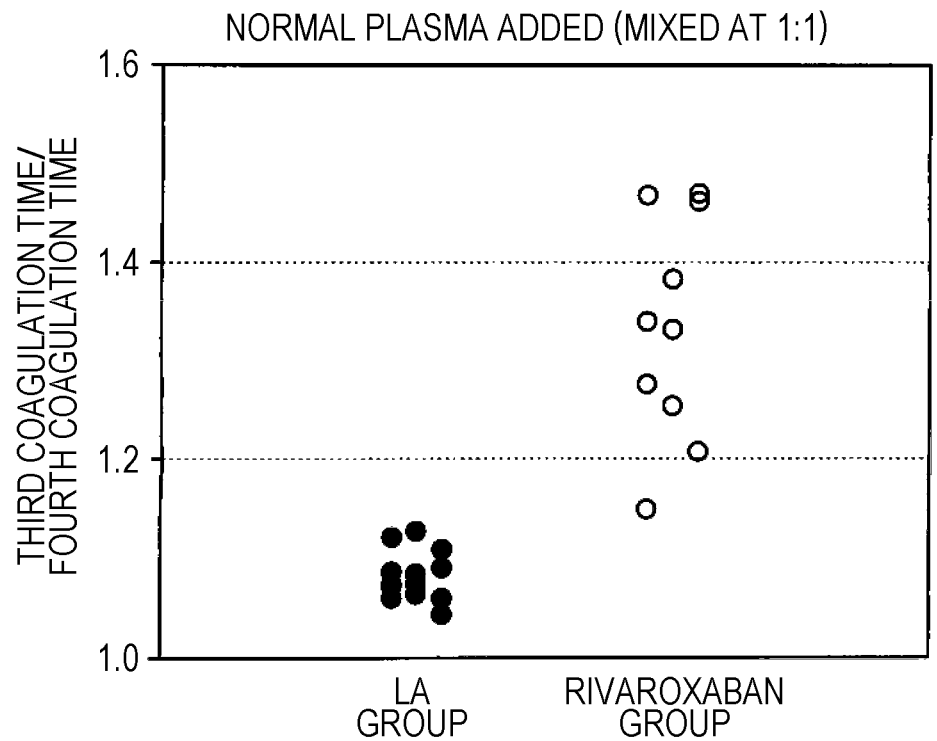
FIG. 11C is a diagram showing distributions of values of Ratio 4 (third coagulation time/fourth coagulation time) in LA specimens and DAC specimens when normal plasma is used as a preparation reagent.
Figure 11D:
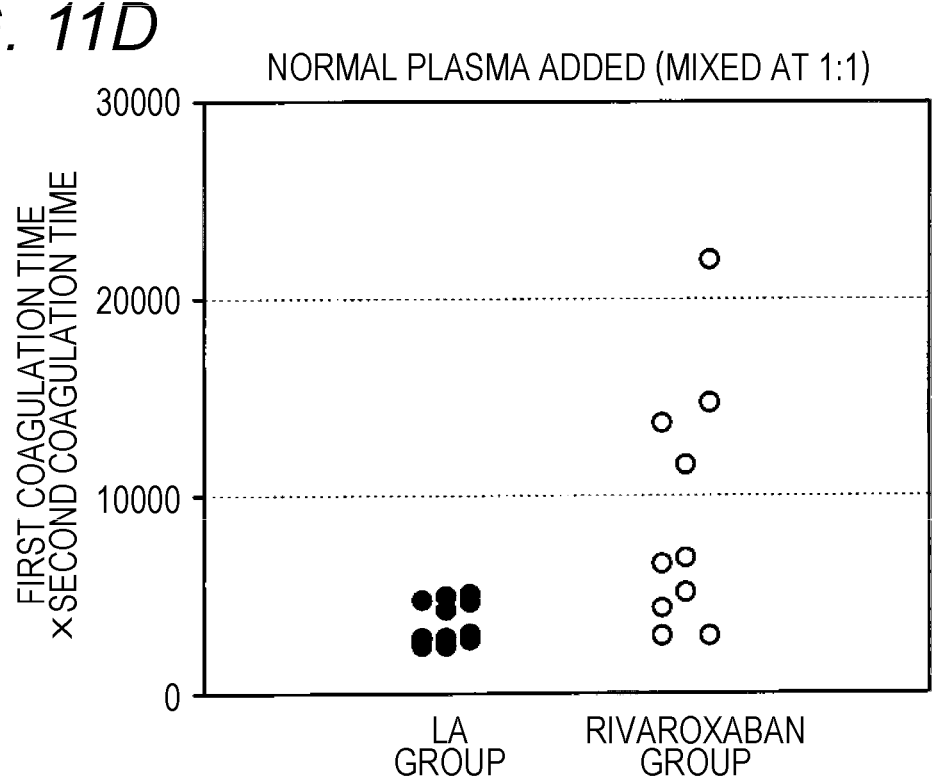
FIG. 11D is a diagram showing distributions of values of Product 1 (first coagulation time×second coagulation time) in LA specimens and DAC specimens when normal plasma is used as a preparation reagent.
Figure 11E:
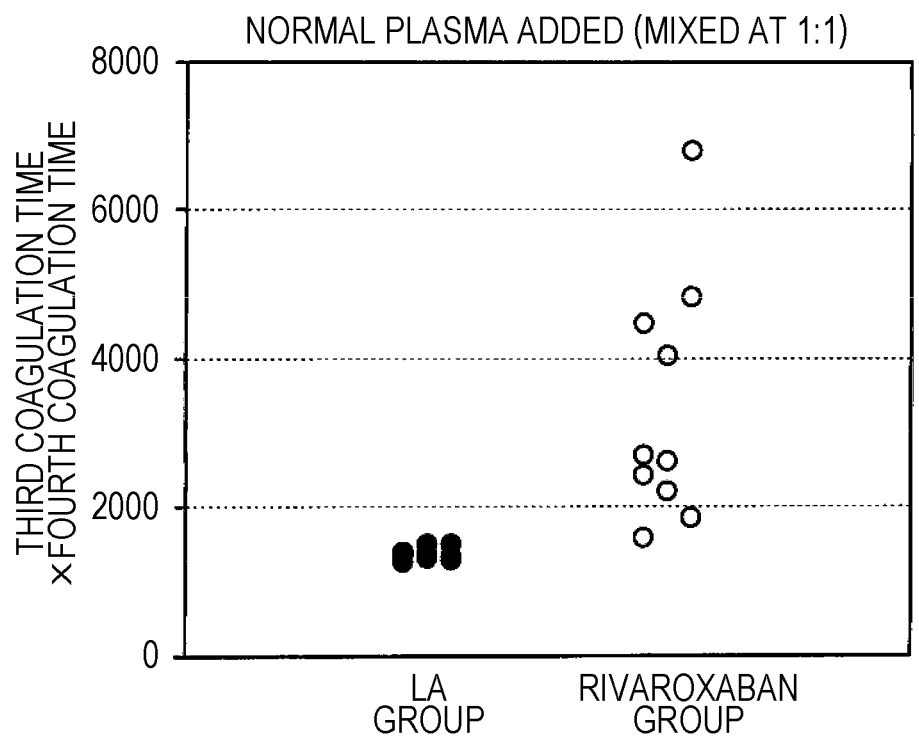
FIG. 11E is a diagram showing distributions of values of Product 2 (third coagulation time×fourth coagulation time) in LA specimens and DAC specimens when normal plasma is used as a preparation reagent.

In Example 1, Ratio 3, Ratio 4, Product 1 and Product 2 are parameters calculated from the coagulation time of the test plasma and the coagulation time of the mixed plasma measured using one kind of coagulation time measurement reagent. As shown in FIGS. 11B and 11C, in Ratio 3 and Product 1, the variation in the values of the LA group was smaller than in Ratio 1. Therefore, it is likely that the LA group and the DAC group can be distinguished by Ratio 3 and Product 1. In Example 1, Ratio 4 and Product 2 were parameters calculated from the coagulation time of the test plasma and the coagulation time of the mixed plasma measured using a coagulation time measurement reagent in which the phospholipid concentration was higher than that of the first coagulation time measurement reagent. As shown in FIGS. 11D and 11E, it can be seen that the LA group and the DAC group can be discriminated by Ratio 4 and Product 2. There was a significant difference between the LA group and the DAC group (p<0.1) for all Ratio 3, Ratio 4, Product 1 and Product 2. These parameters were shown to be useful indexes for discrimination between blood specimens containing LA and blood specimens containing DAC. From these results, it is suggested that the product of Ratio 3 and Ratio 4 and the product of Product 1 and Product 2 can also be used for discrimination between the LA group and the DAC group.

Figure 11F:
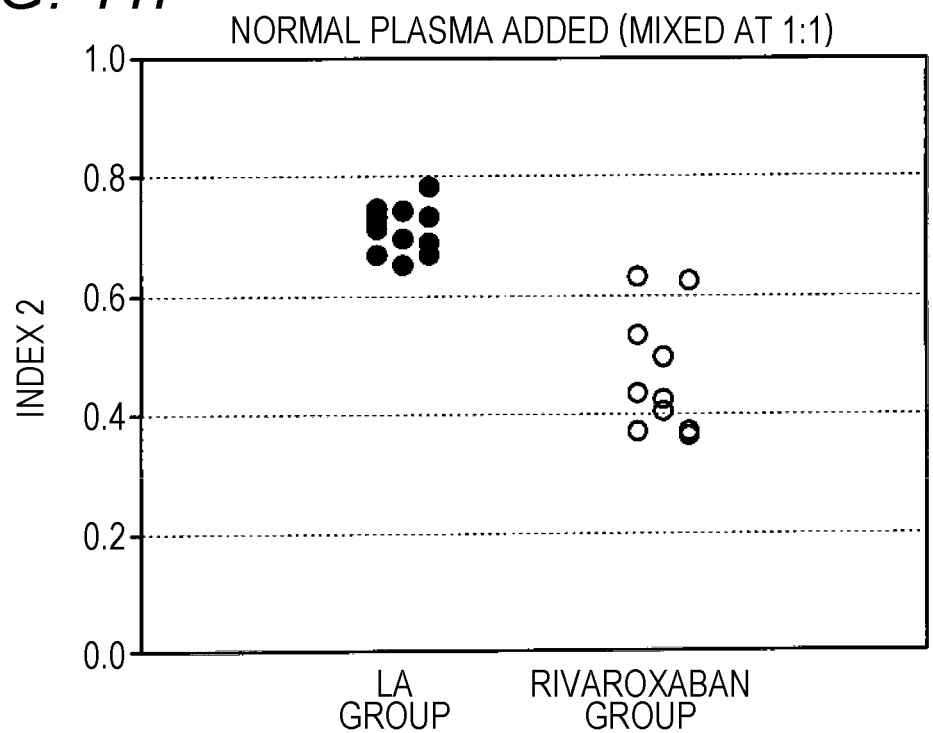
FIG. 11F is a diagram showing distributions of values of Index 2 ((second coagulation time/first coagulation time)×(fourth coagulation time/third coagulation time)) in LA specimens and DAC specimens when normal plasma is used as a preparation reagent.
Figure 12A:
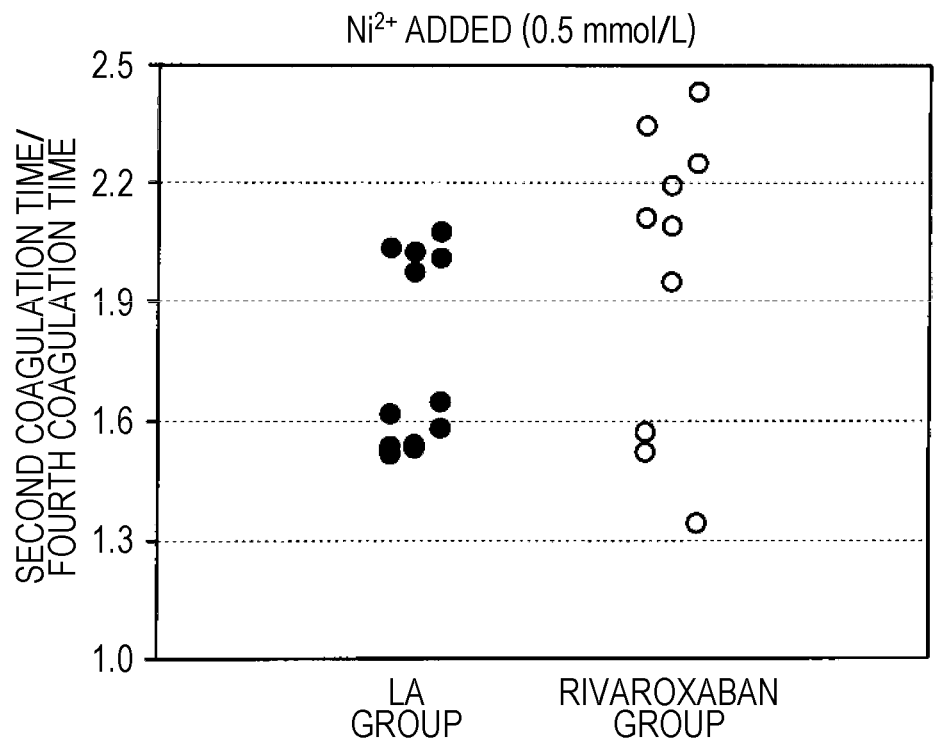
FIG. 12A is a diagram showing distributions of values of Ratio 2 in LA specimens and DAC specimens when a nickel ion is used as a preparation reagent.
Figure 12B:
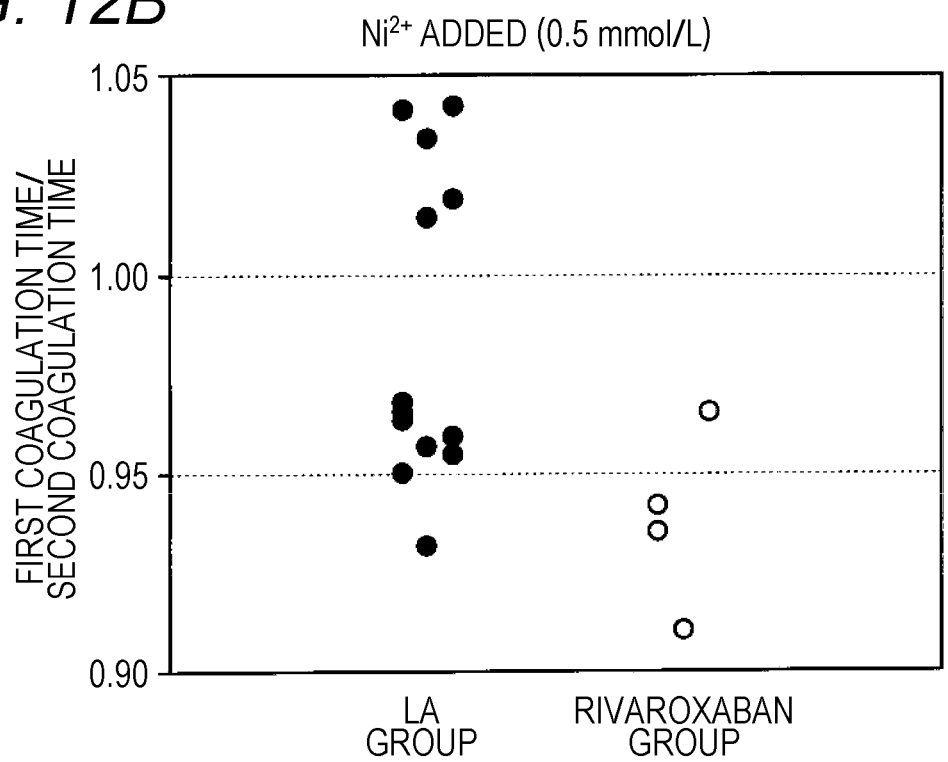
FIG. 12B is a diagram showing distributions of values of Ratio 3 in LA specimens and DAC specimens when a nickel ion is used as a preparation reagent.
Figure 12C:
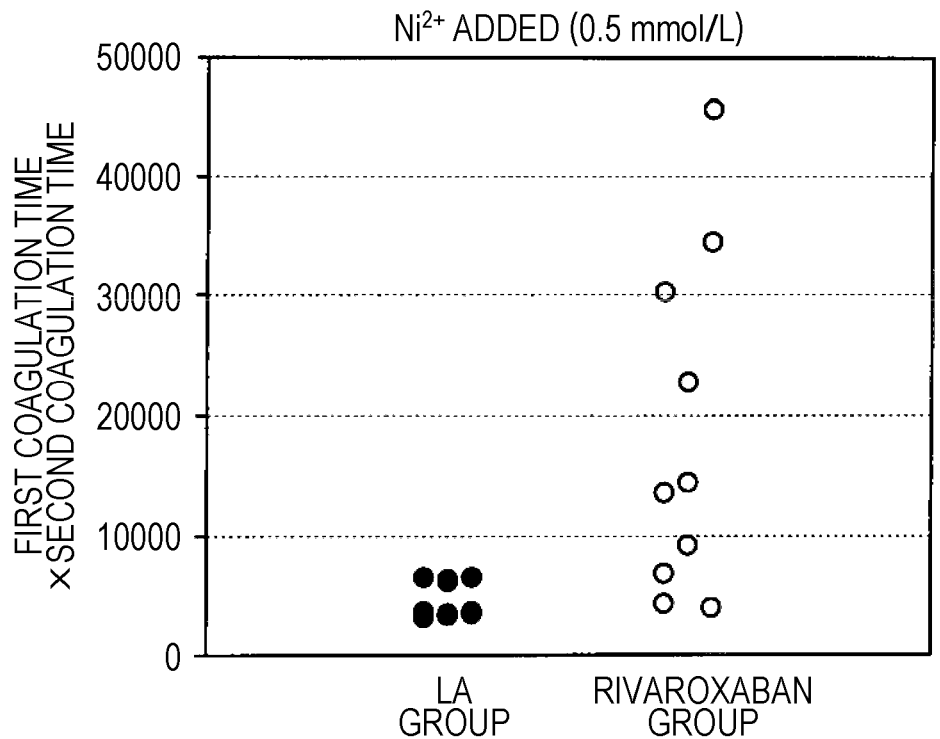
FIG. 12C is a diagram showing distributions of Product 1 value in LA specimens and DAC specimens when a nickel ion is used as a preparation reagent.
Figure 12D:
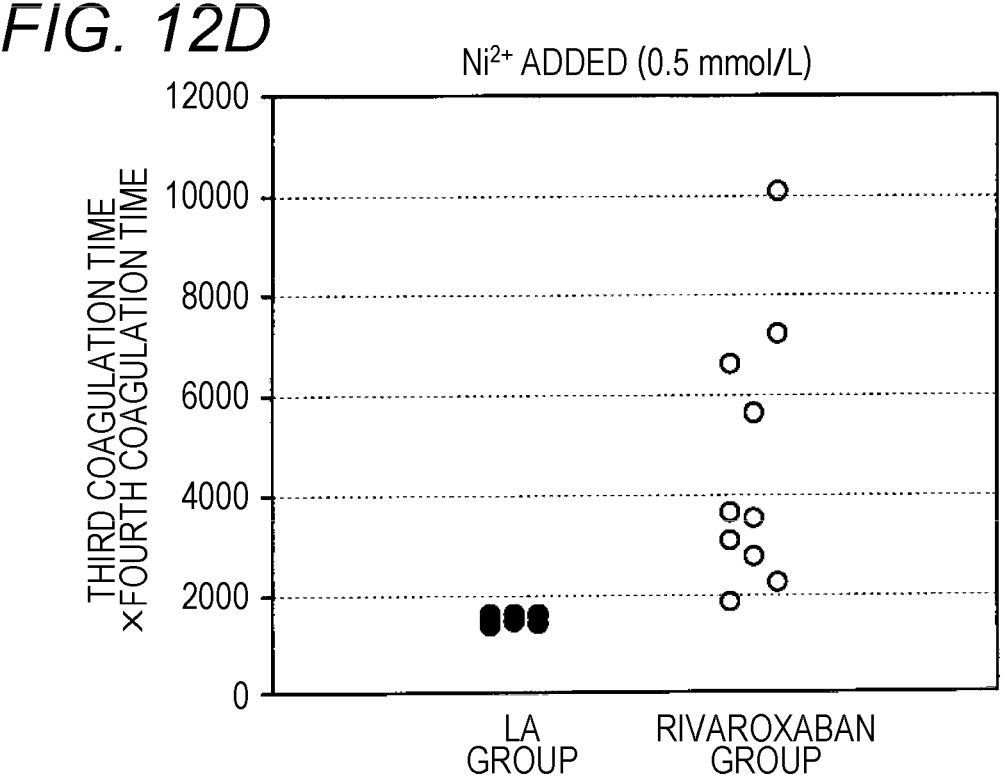
FIG. 12D is a diagram showing distributions of Product 2 value in LA specimens and DAC specimens when a nickel ion is used as a preparation reagent.
Figure 12E:
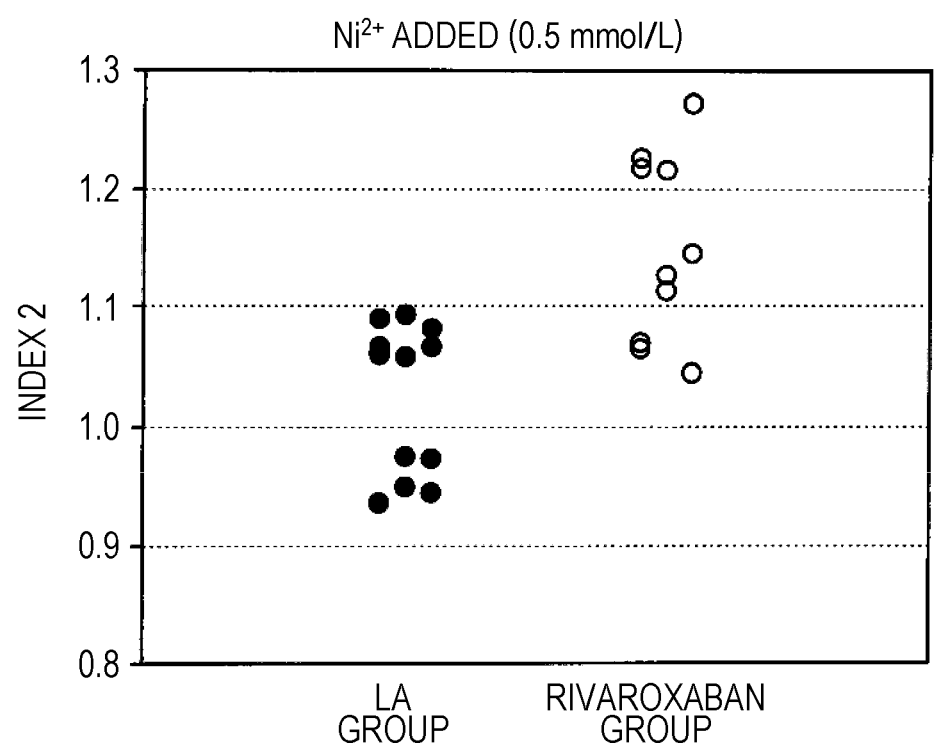
FIG. 12E is a diagram showing distributions of Index 2 value in LA specimens and DAC specimens when a nickel ion is used as a preparation reagent.
Figure 13A:
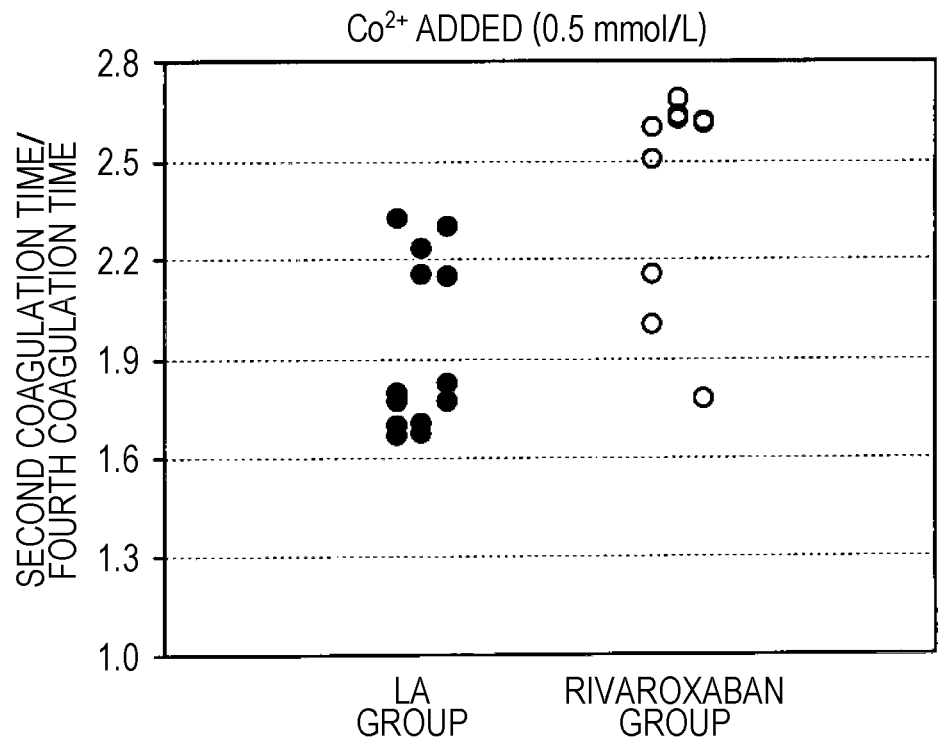
FIG. 13A is a diagram showing distributions of values of Ratio 2 in LA specimens and DAC specimens when a cobalt ion is used as a preparation reagent.
Figure 13B:
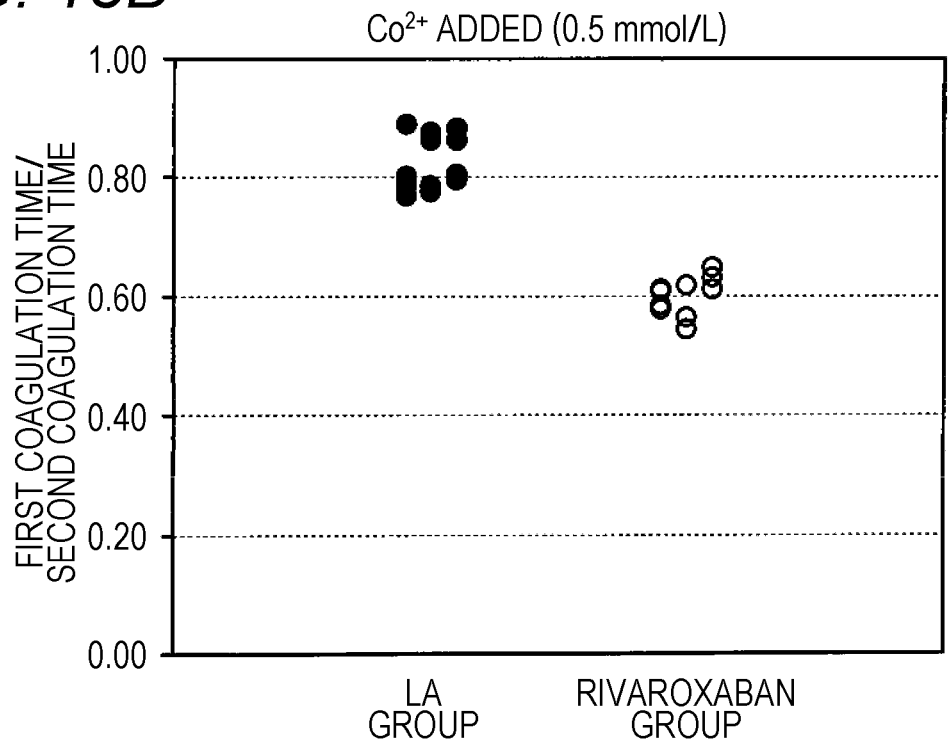
FIG. 13B is a diagram showing distributions of values of Ratio 3 in LA specimens and DAC specimens when a cobalt ion is used as a preparation reagent.
Figure 13C:
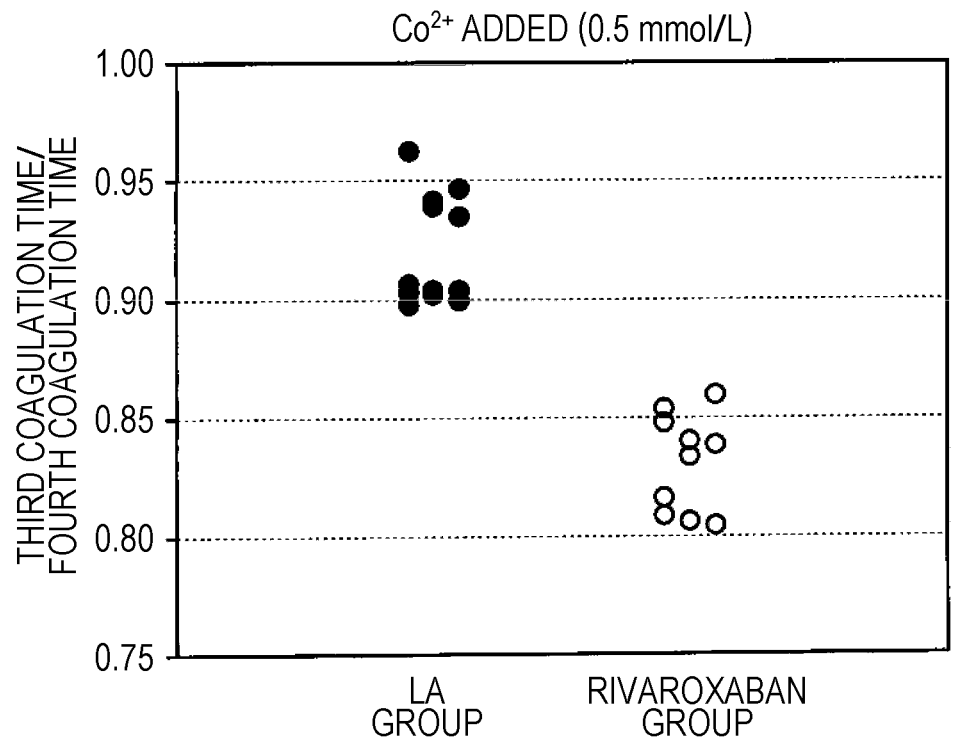
FIG. 13C is a diagram showing distributions of values of Ratio 4 in LA specimens and DAC specimens when a cobalt ion is used as a preparation reagent.
Figure 13D:
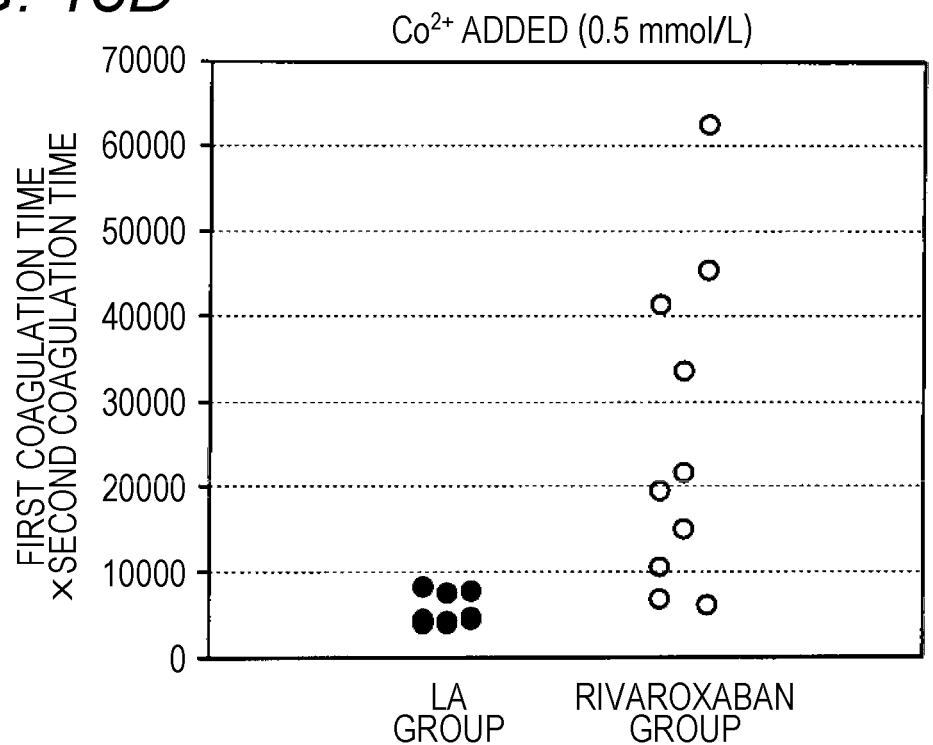
FIG. 13D is a diagram showing distributions of values of Product 1 in LA specimens and DAC specimens when a cobalt ion is used as a preparation reagent.
Figure 13E:
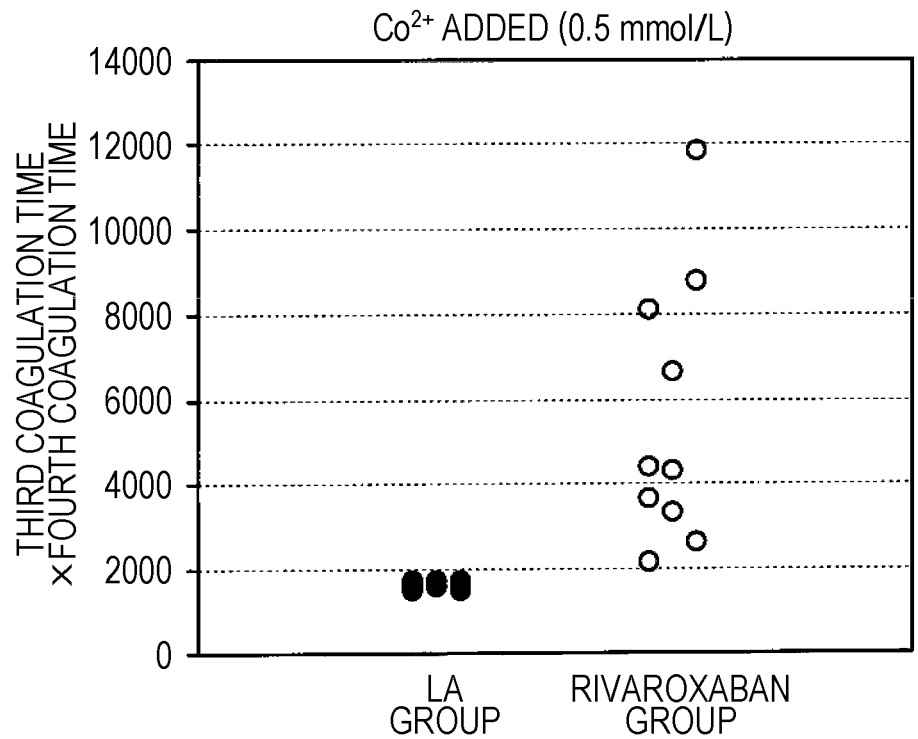
FIG. 13E is a diagram showing distributions of values of Product 2 in LA specimens and DAC specimens when a cobalt ion is used as a preparation reagent.
Figure 13F:
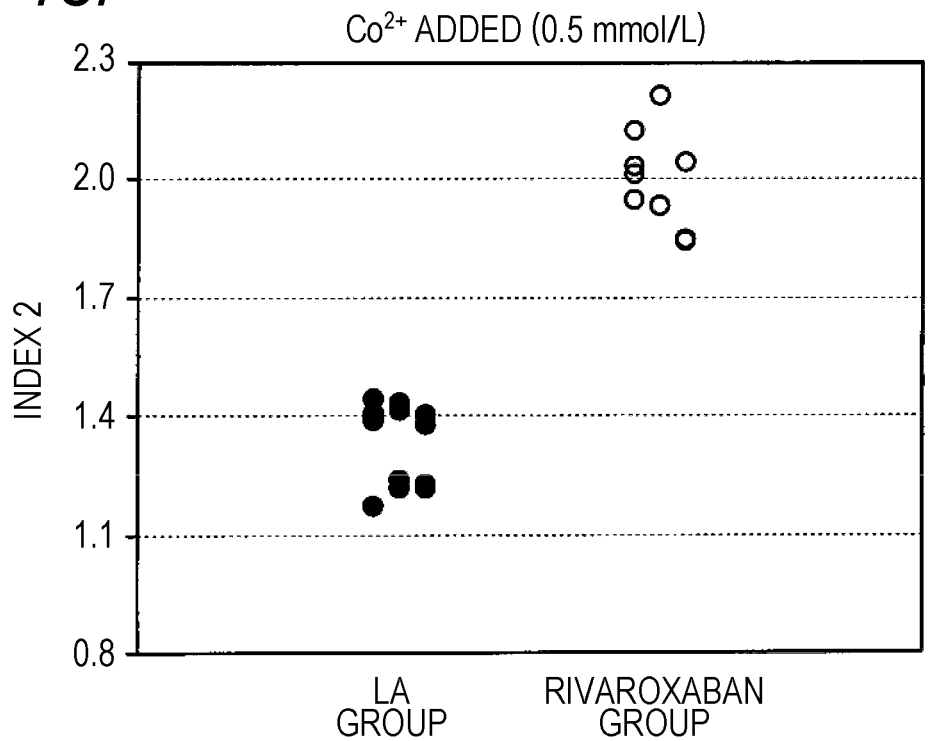
FIG. 13F is a diagram showing distributions of values of Index 2 in LA specimens and DAC specimens when a cobalt ion is used as a preparation reagent.
Figure 14A:
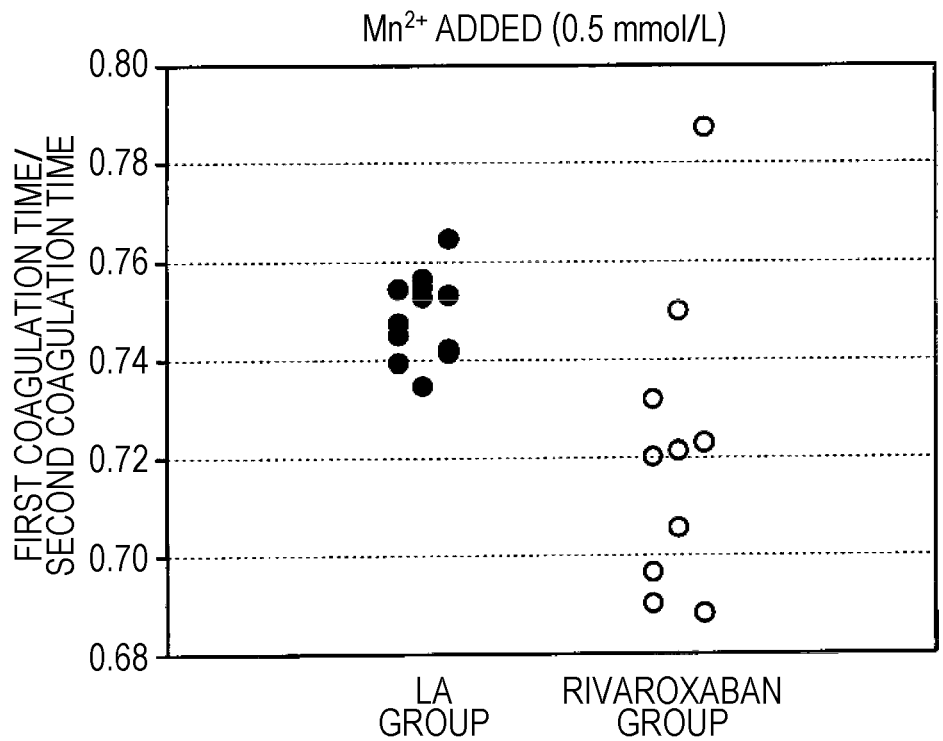
FIG. 14A is a diagram showing distributions of values of Ratio 3 in LA specimens and DAC specimens when a manganese ion is used as a preparation reagent.
Figure 14B:
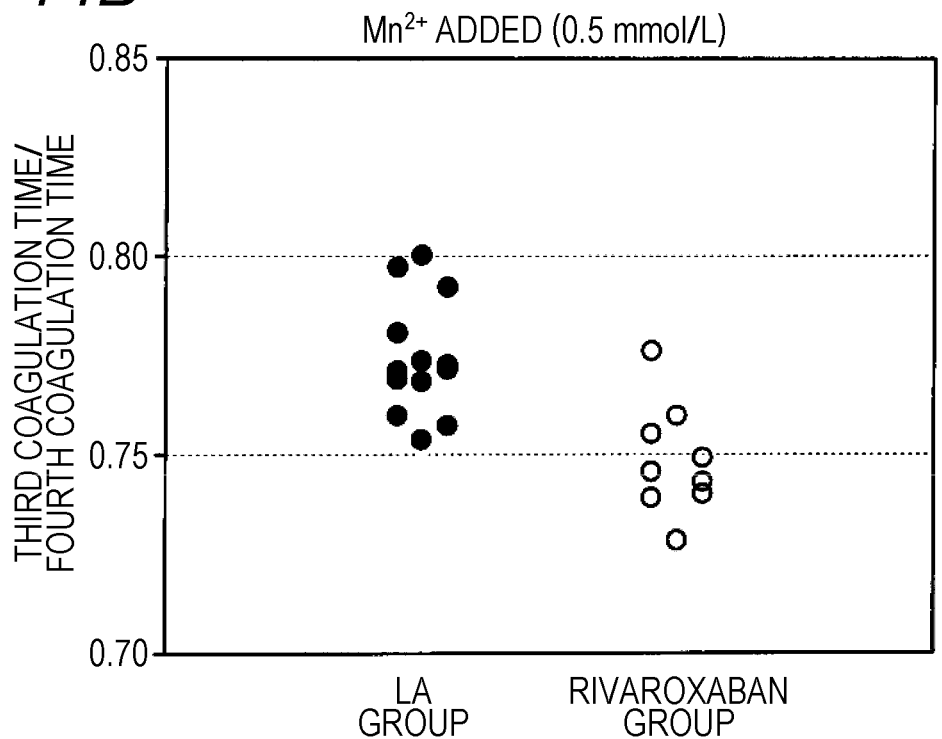
FIG. 14B is a diagram showing distributions of values of Ratio 4 in LA specimens and DAC specimens when a manganese ion is used as a preparation reagent.
Figure 14C:
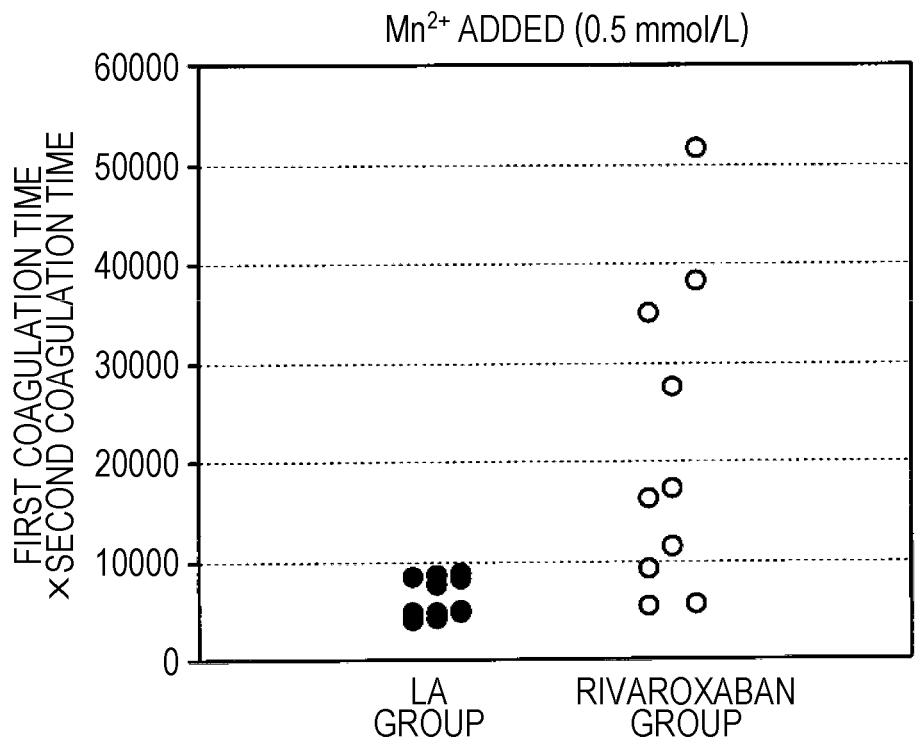
FIG. 14C is a diagram showing distributions of values of Product 1 in LA specimens and DAC specimens when a manganese ion is used as a preparation reagent.
Figure 14D:
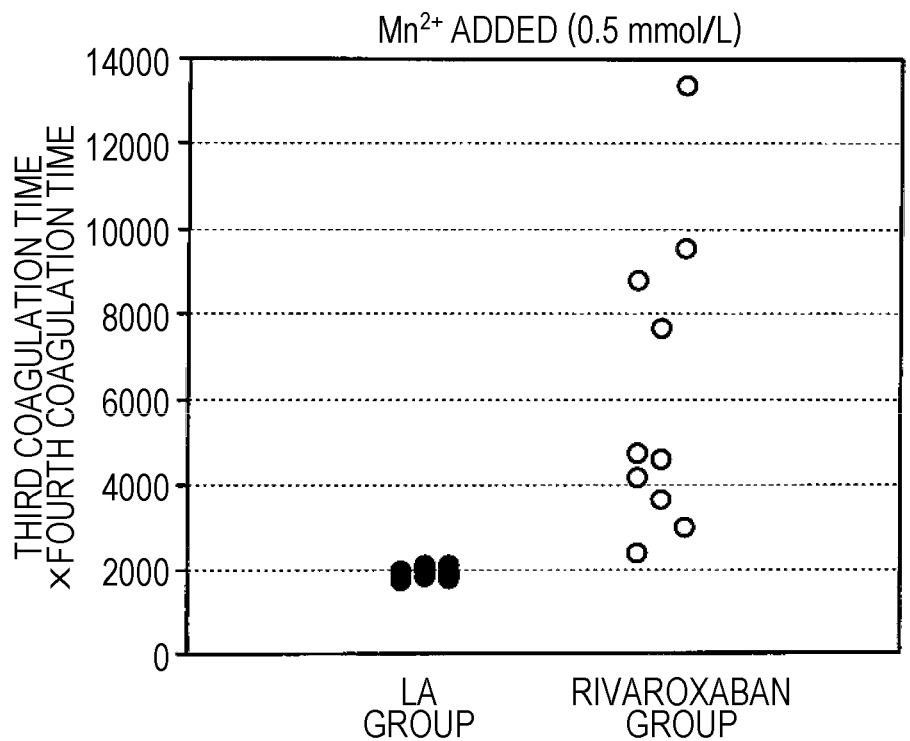
FIG. 14D is a diagram showing distributions of values of Product 2 in LA specimens and DAC specimens when a manganese ion is used as a preparation reagent.
Figure 14E:
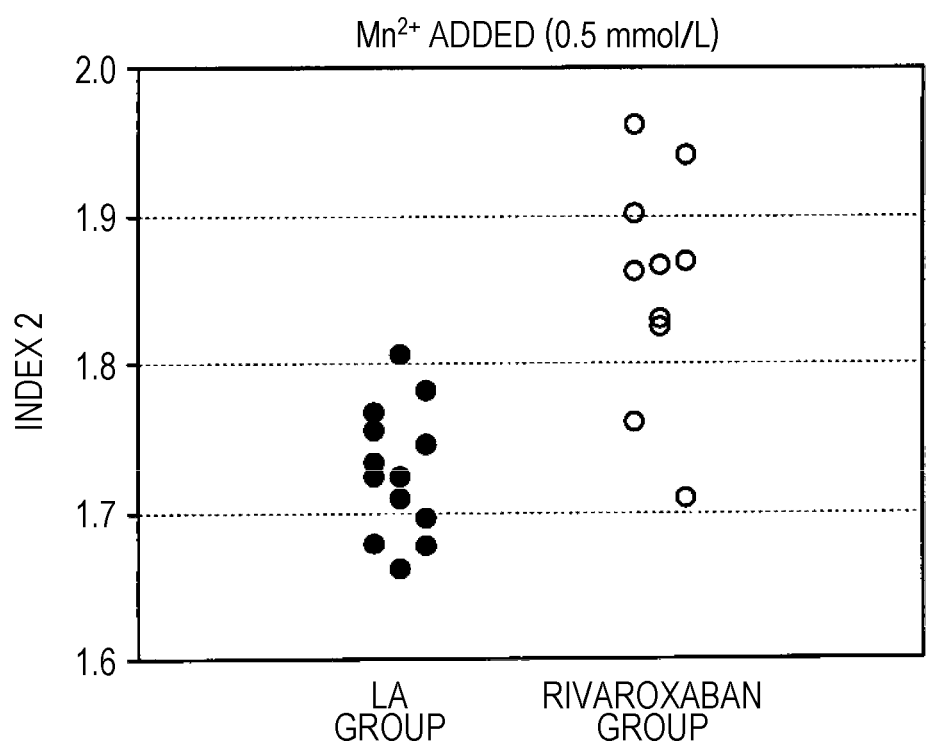
FIG. 14E is a diagram showing distributions of values of Index 2 in LA specimens and DAC specimens when a manganese ion is used as a preparation reagent.
Figure 15A:
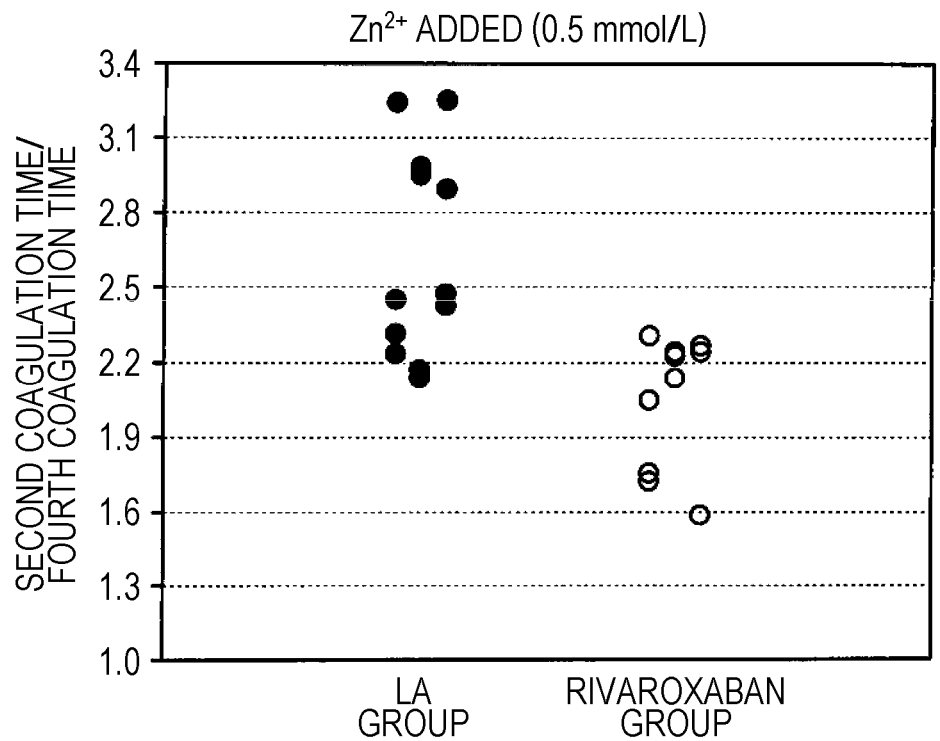
FIG. 15A is a diagram showing distributions of values of Ratio 2 in LA specimens and DAC specimens when a zinc ion is used as a preparation reagent.
Figure 15B:
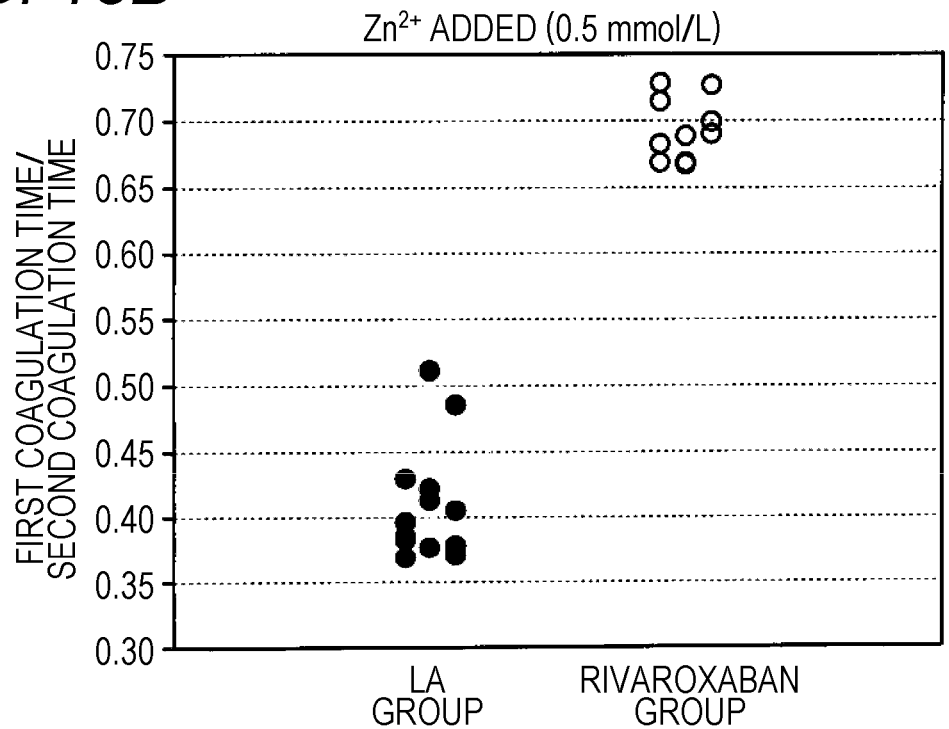
FIG. 15B is a diagram showing distributions of values of Ratio 3 in LA specimens and DAC specimens when a zinc ion is used as a preparation reagent.
Figure 15C:
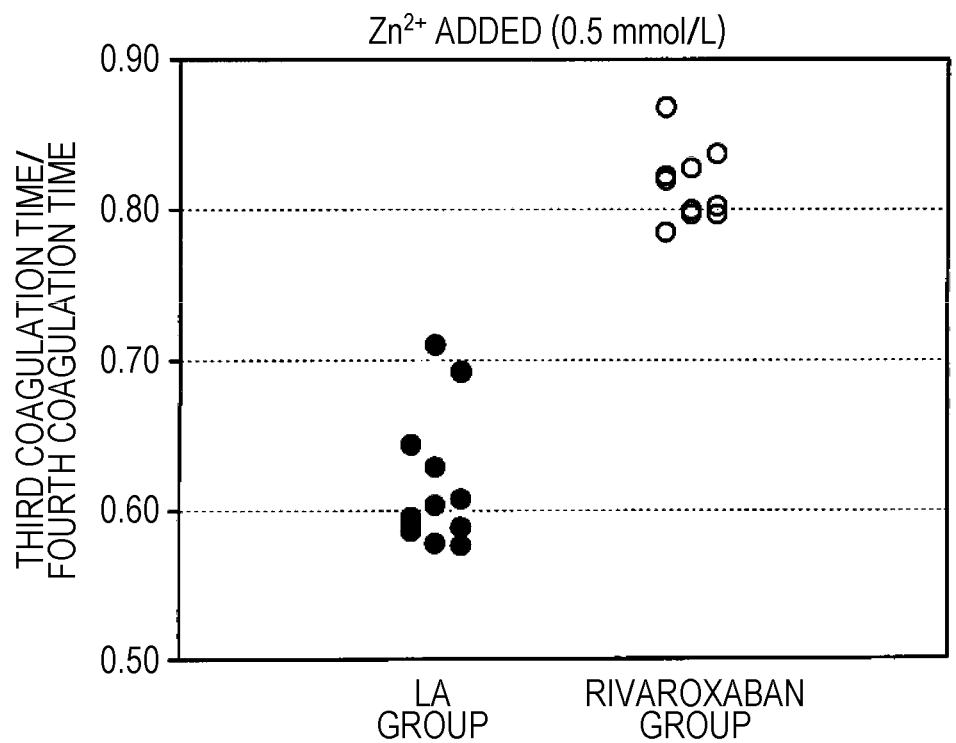
FIG. 15C is a diagram showing distributions of values of Ratio 4 in LA specimens and DAC specimens when a zinc ion is used as a preparation reagent.
Figure 15D:
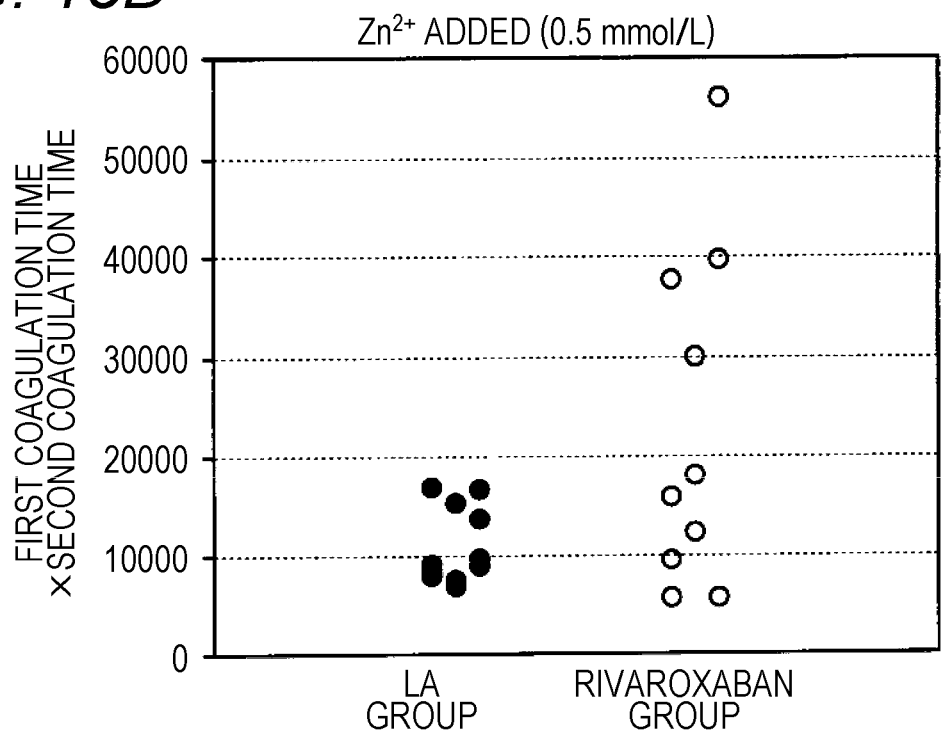
FIG. 15D is a diagram showing distributions of values of Product 1 in LA specimens and DAC specimens when a zinc ion is used as a preparation reagent.
Figure 15E:
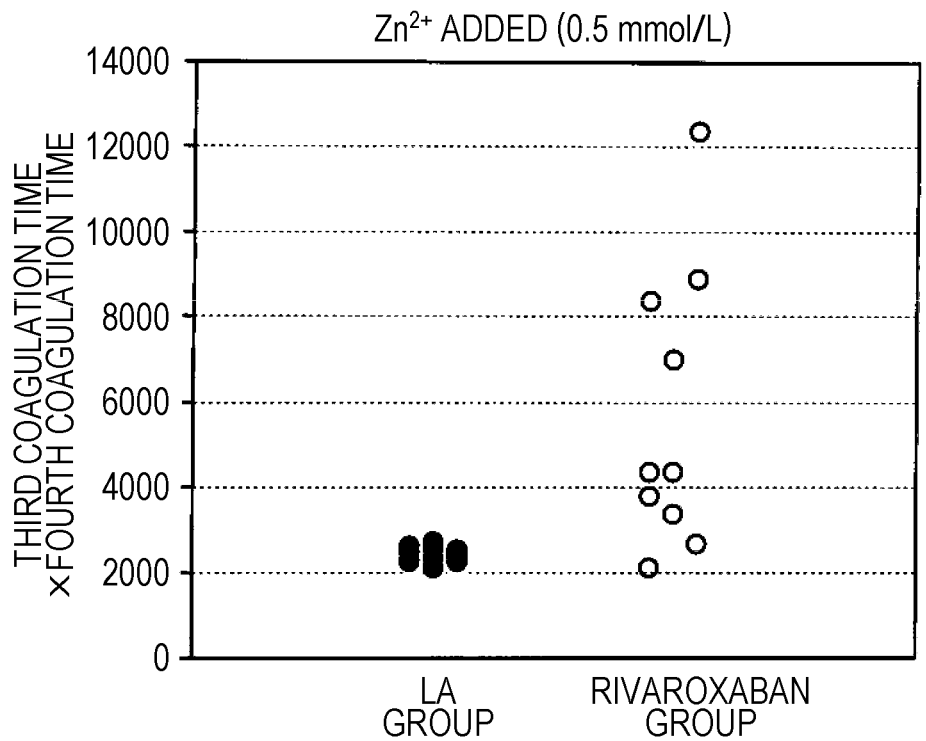
FIG. 15E is a diagram showing distributions of values of Product 2 in LA specimens and DAC specimens when a zinc ion is used as a preparation reagent.
Figure 15F:
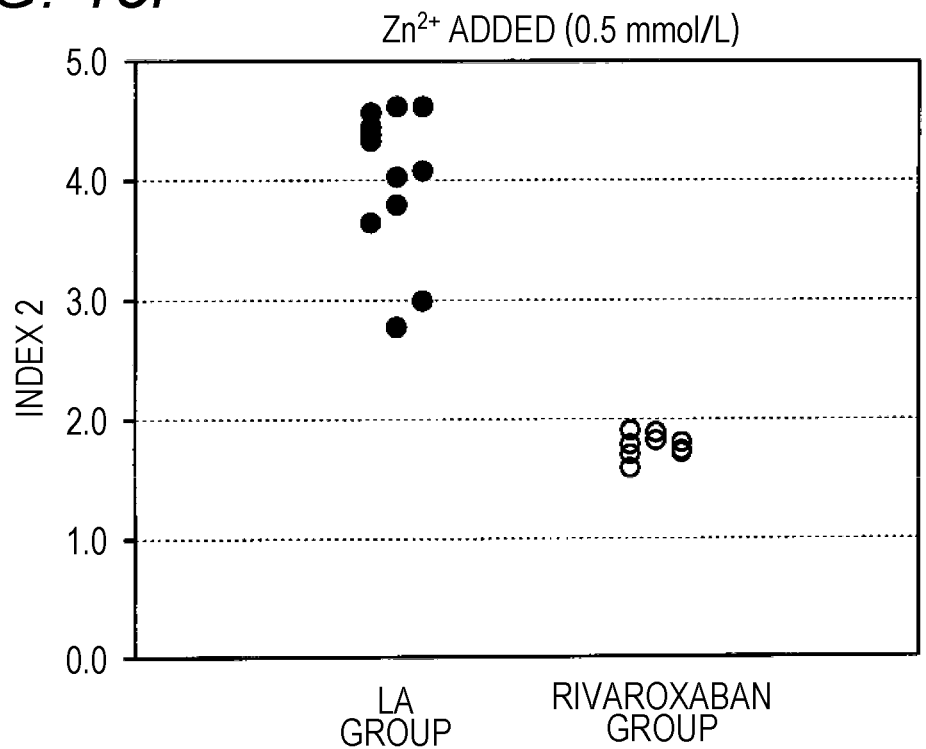
FIG. 15F is a diagram showing the distribution of values of Index 2 in LA specimens and DAC specimens when a zinc ion is as a preparation reagent.
Figure 16A:
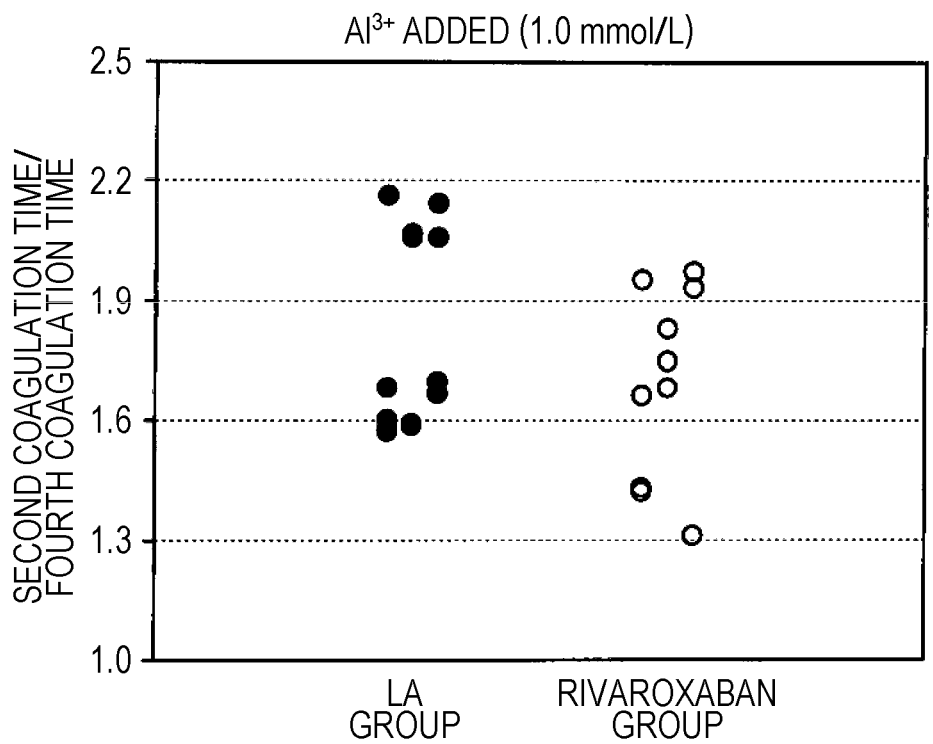
FIG. 16A is a diagram showing distributions of values of Ratio 2 in LA specimens and DAC specimens when an aluminum ion is used as a preparation reagent.
Figure 16B:
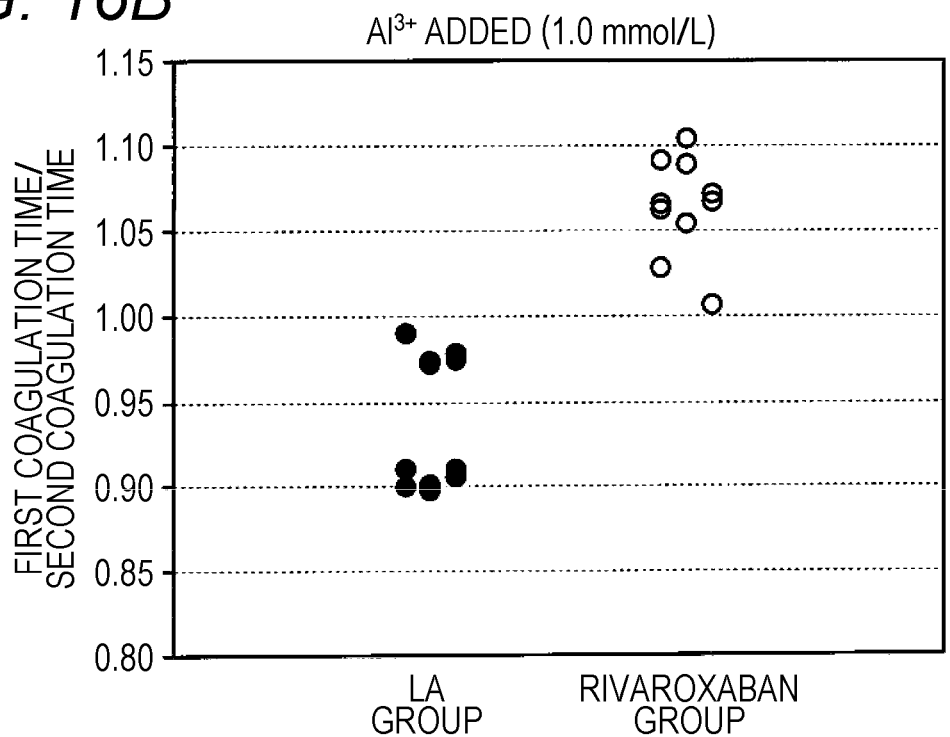
FIG. 16B is a diagram showing distributions of values of Ratio 3 in LA specimens and DAC specimens when an aluminum ion is used as a preparation reagent.
Figure 16C:
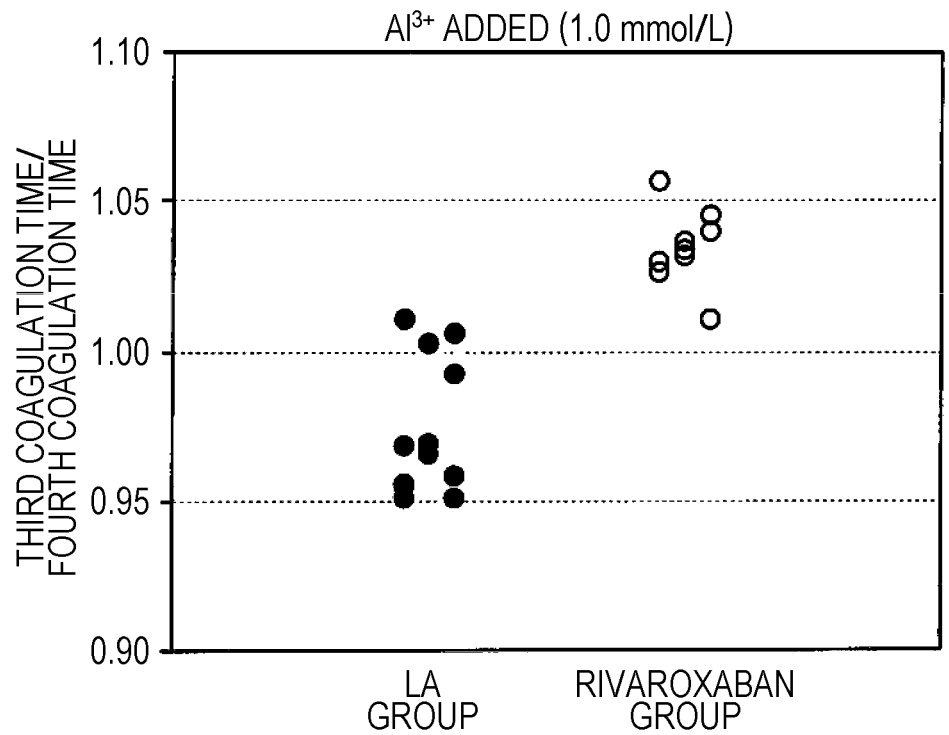
FIG. 16C is a diagram showing distributions of values of Ratio 4 in LA specimens and DAC specimens when an aluminum ion is used as a preparation reagent.
Figure 16D:
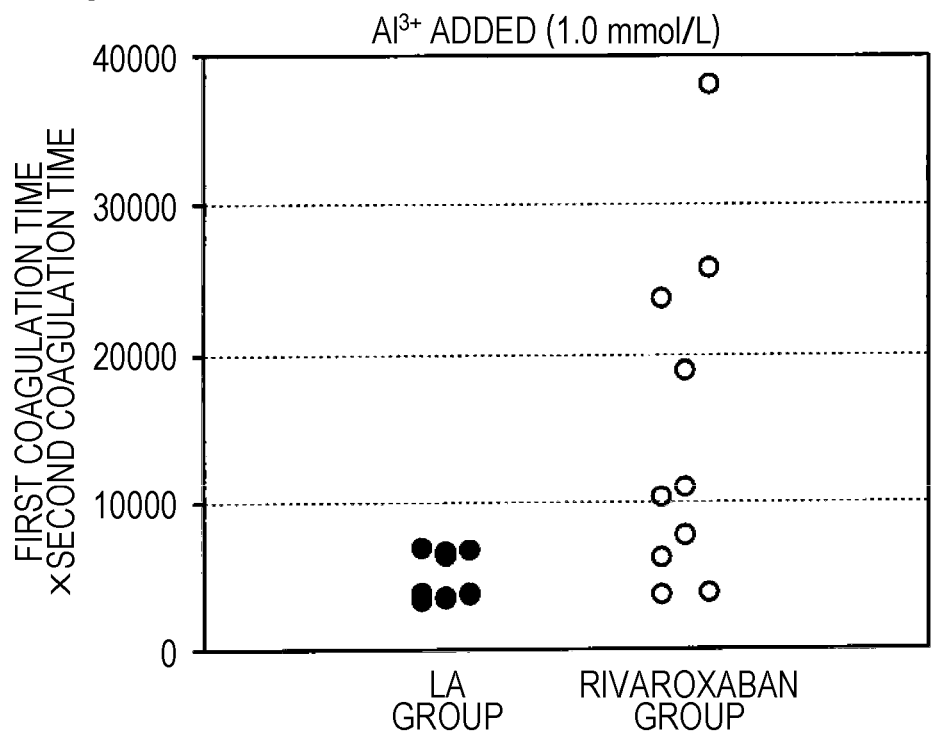
FIG. 16D is a diagram showing distributions of values of Product 1 in LA specimens and DAC specimens when an aluminum ion is used as a preparation reagent.
Figure 16E:
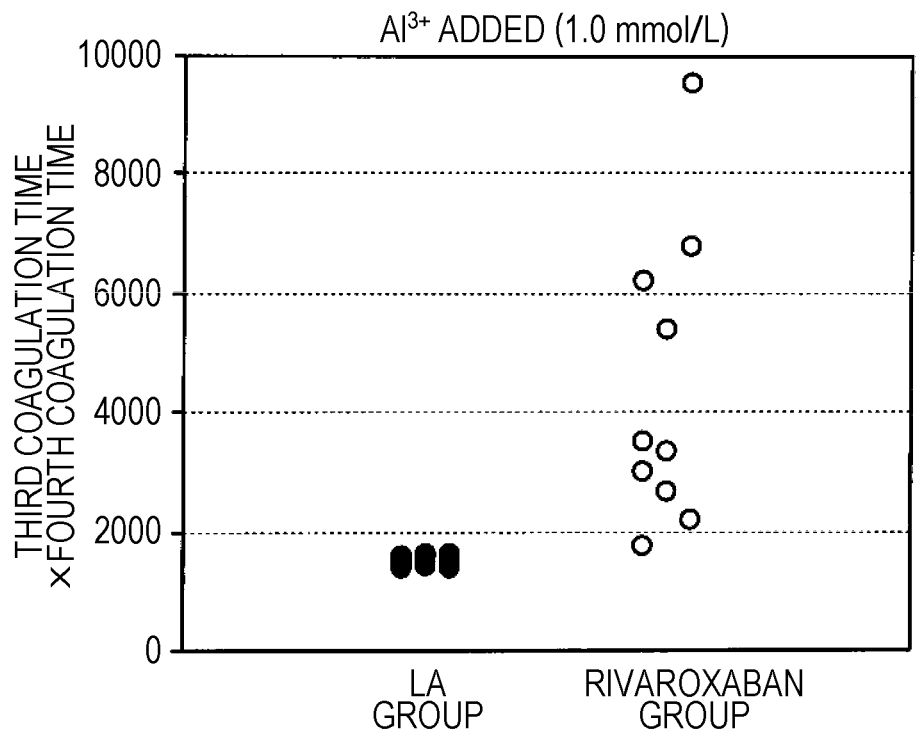
FIG. 16E is a diagram showing distributions of values of Product 2 in LA specimens and DAC specimens when an aluminum ion is used as a preparation reagent.
Figure 16F:
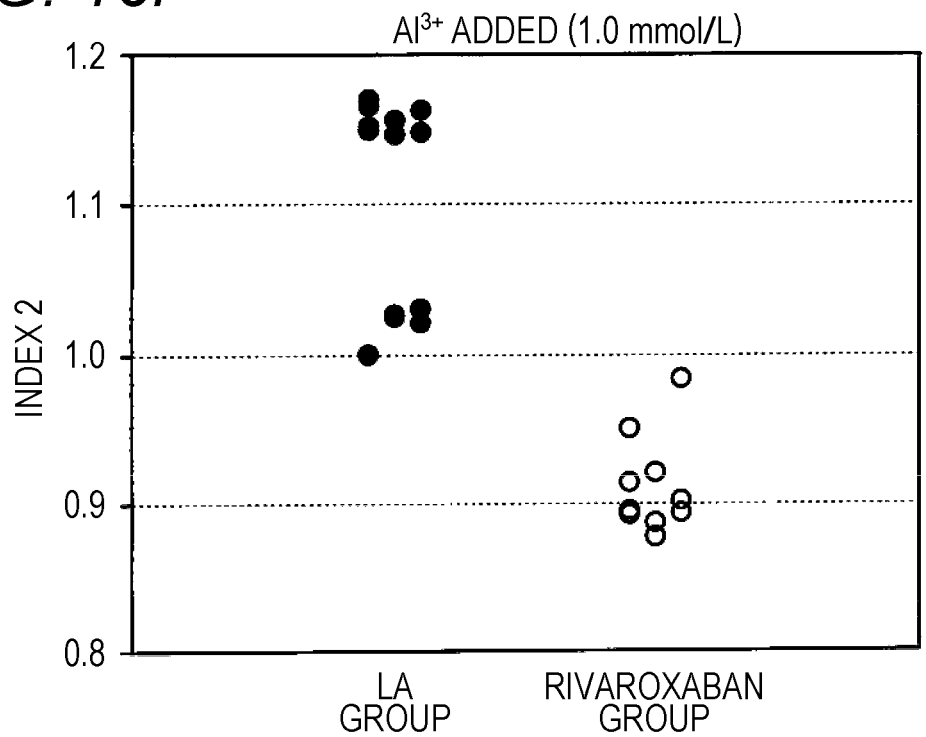
FIG. 16F is a diagram showing distributions of values of Index 2 in LA specimens and DAC specimens when an aluminum ion is used as a preparation reagent.
Figure 17A:
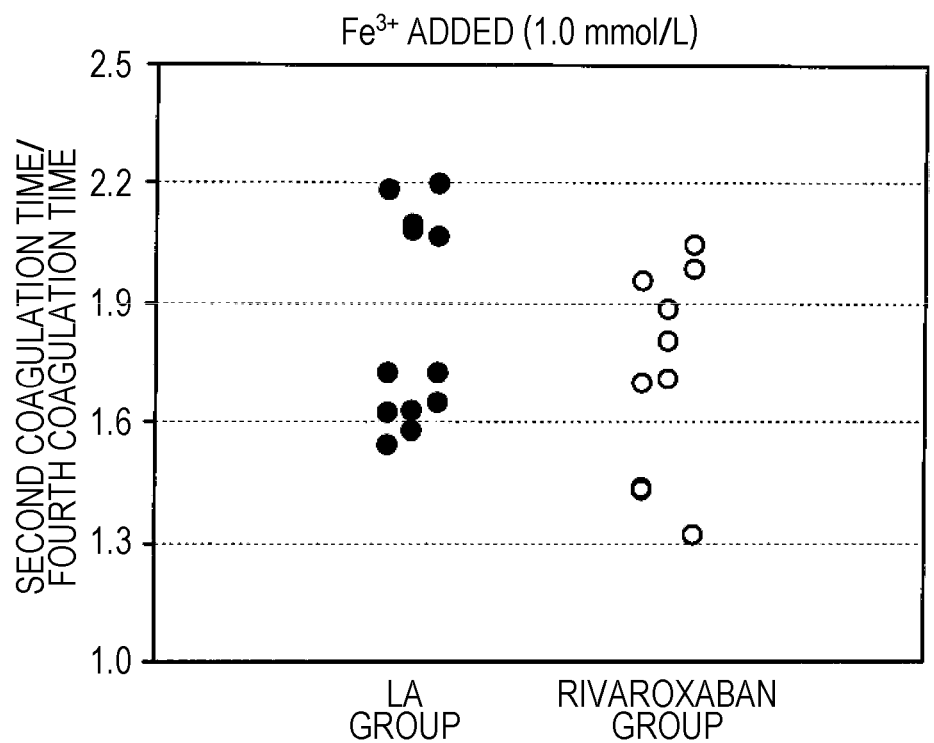
FIG. 17A is a diagram showing distributions of values of Ratio 2 in LA specimens and DAC specimens when an iron ion is used as a preparation reagent.
Figure 17B:
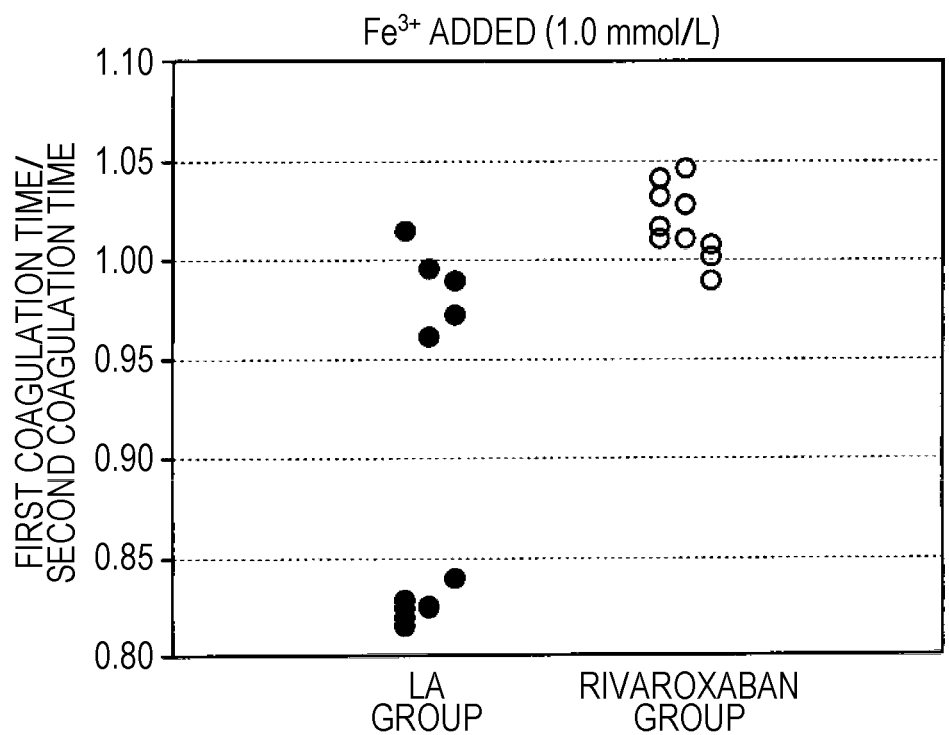
FIG. 17B is a diagram showing distributions of values of Ratio 3 in LA specimens and DAC specimens when an iron ion is used as a preparation reagent.
Figure 17C:
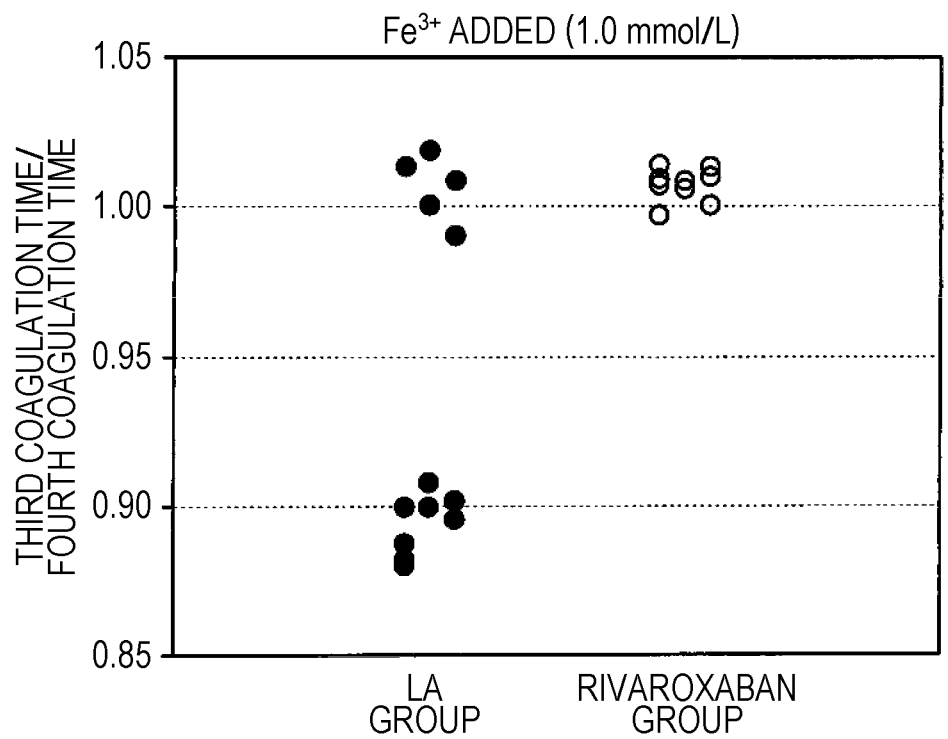
FIG. 17C is a diagram showing distributions of values of Ratio 4 in LA specimens and DAC specimens when an iron ion is used as a preparation reagent.
Figure 17D:
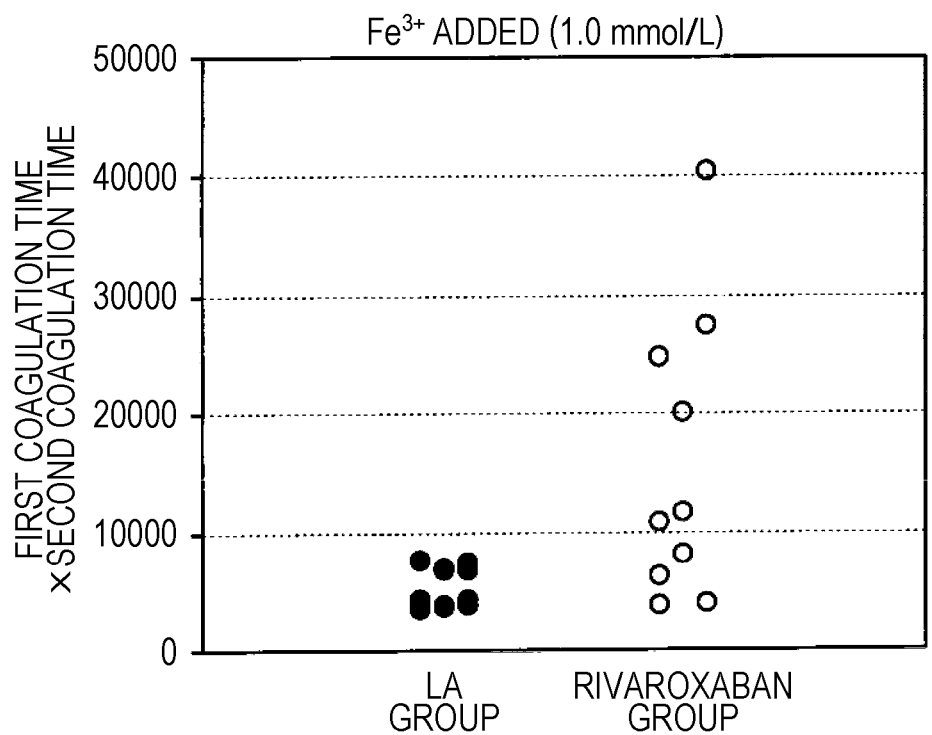
FIG. 17D is a diagram showing distributions of values of Product 1 in LA specimens and DAC specimens when an iron ion is used as a preparation reagent.
Figure 17E:
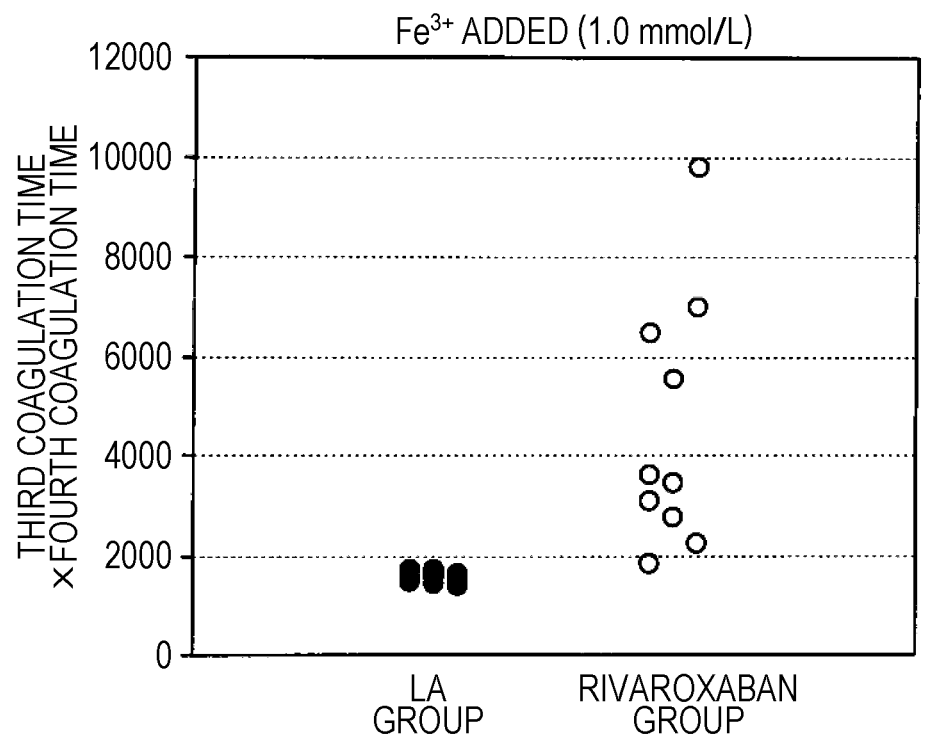
FIG. 17E is a diagram showing distributions of values of Product 2 in LA specimens and DAC specimens when an iron ion is used as a preparation reagent.
Figure 17F:
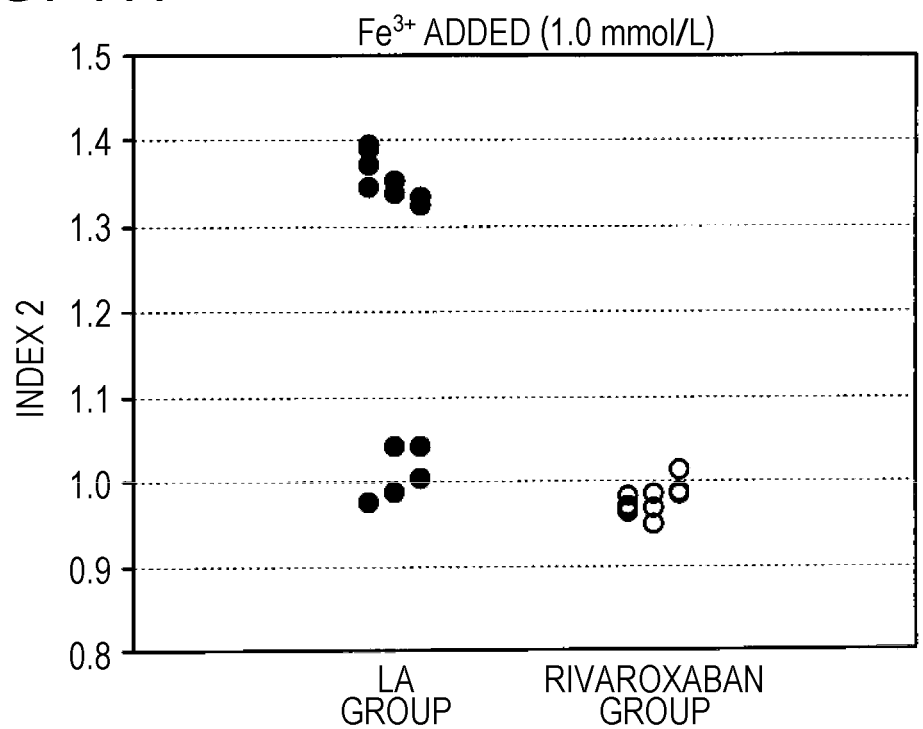
FIG. 17F is a diagram showing distributions of values of Index 2 in LA specimens and DAC specimens when an iron ion is used as a preparation reagent.
Figure 18A:
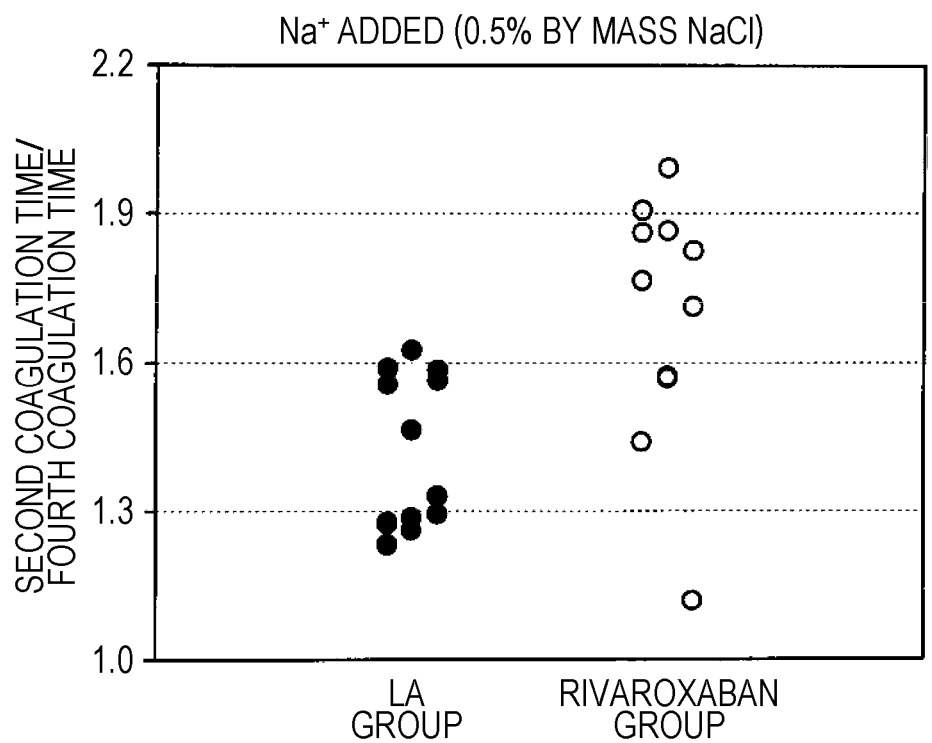
FIG. 18A is a diagram showing distributions of values of Ratio 2 in LA specimens and DAC specimens when a sodium ion (NaCl) is used as a preparation reagent.
Figure 18B:
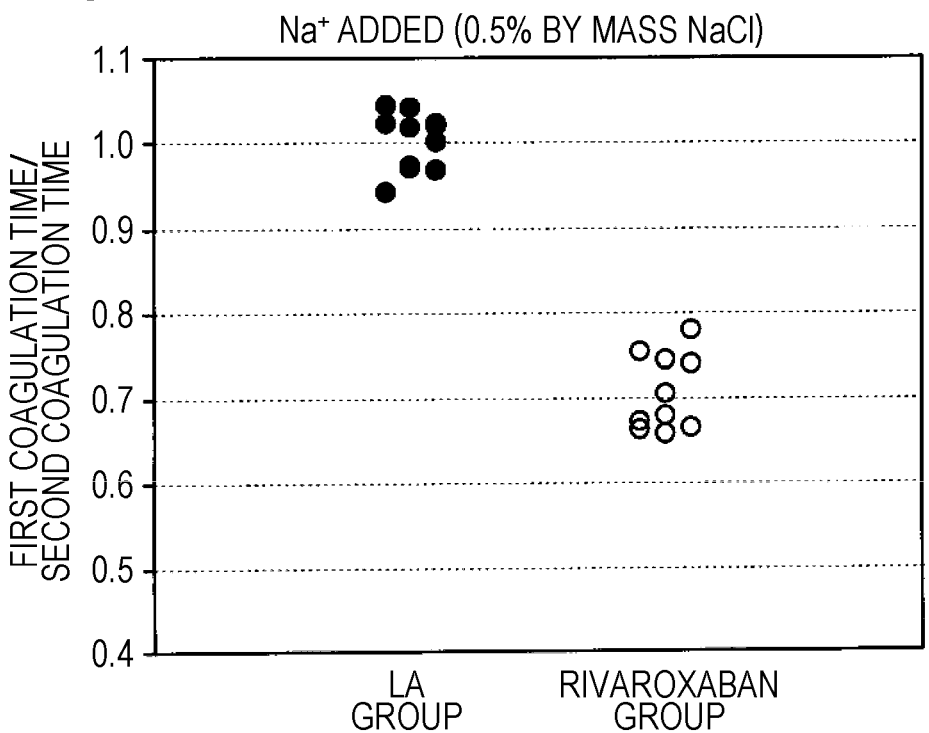
FIG. 18B is a diagram showing distributions of values of Ratio 3 in LA specimens and DAC specimens when a sodium ion (NaCl) is used as a preparation reagent.
Figure 18C:
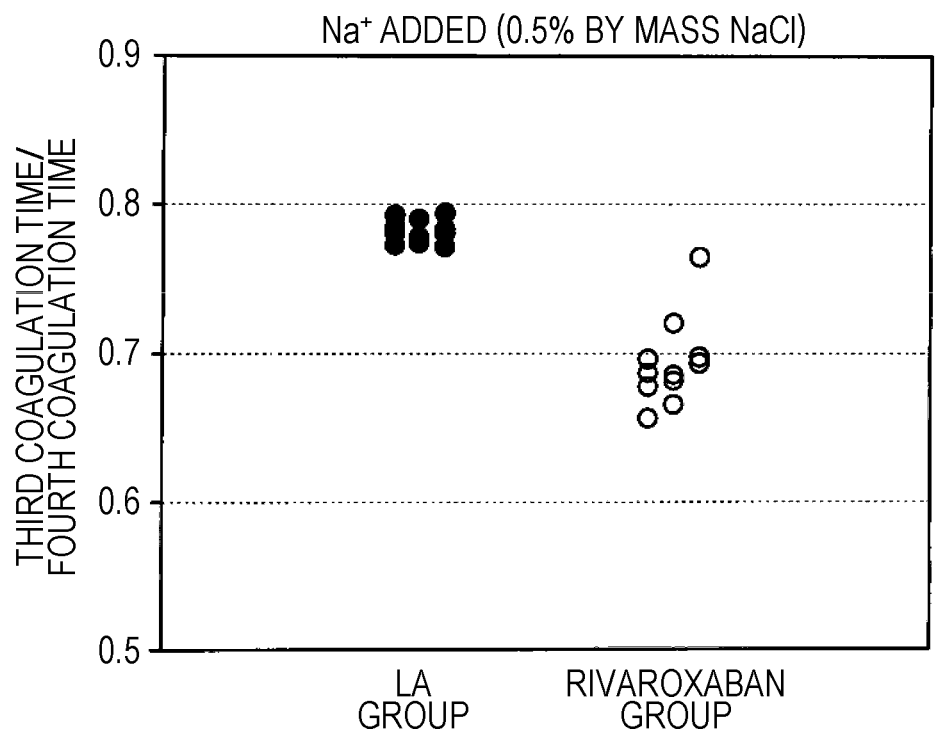
FIG. 18C is a diagram showing distributions of values of Ratio 4 in LA specimens and DAC specimens when a sodium ion (NaCl) is used as a preparation reagent.
Figure 18D:
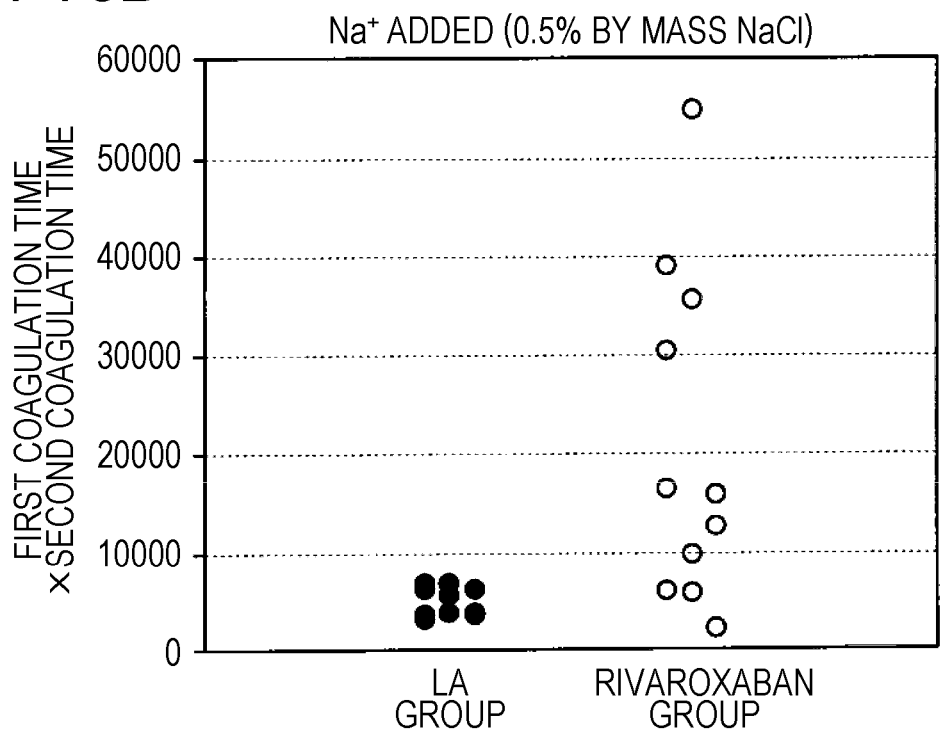
FIG. 18D is a diagram showing distributions of values of Product 1 in LA specimens and DAC specimens when a sodium ion (NaCl) is used as a preparation reagent.
Figure 18E:
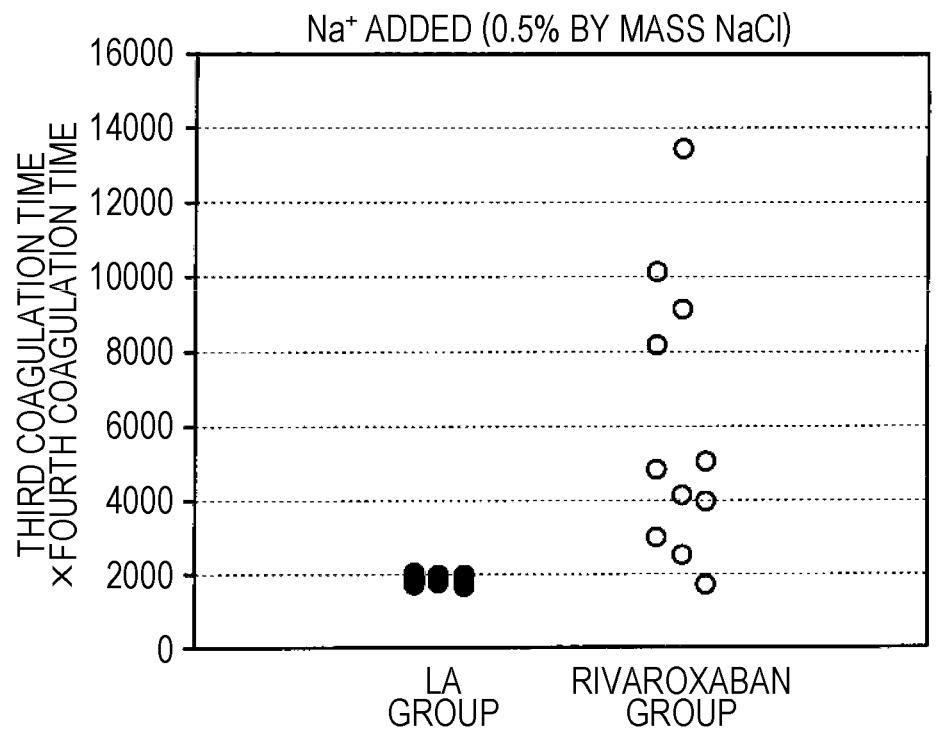
FIG. 18E is a diagram showing distributions of values of Product 2 in LA specimens and DAC specimens when a sodium ion (NaCl) is used as a preparation reagent.
Figure 18F:
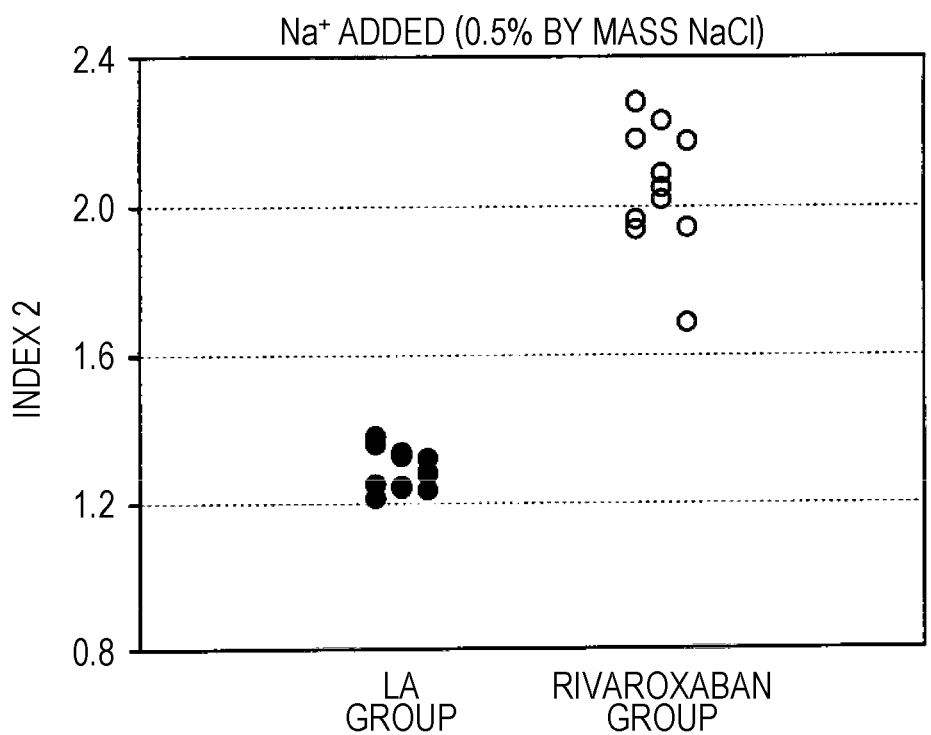
FIG. 18F is a diagram showing distributions of values of Index 2 in LA specimens and DAC specimens when a sodium ion (NaCl) is used as a preparation reagent.
Figure 19A:
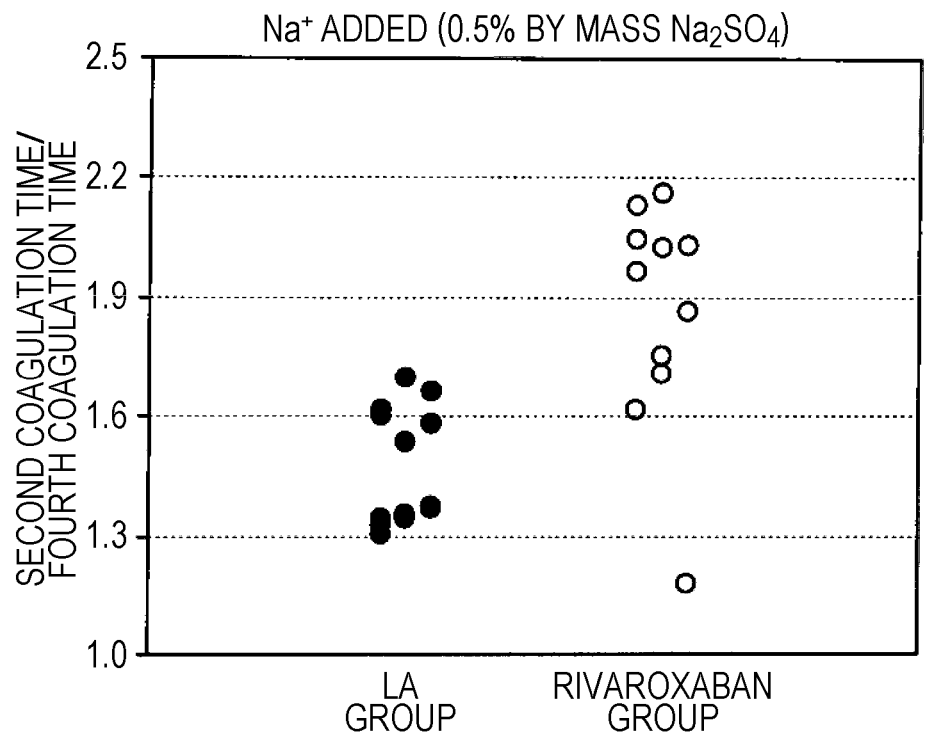
FIG. 19A is a diagram showing distributions of values of Ratio 2 in LA specimens and DAC specimens when a sodium ion ($Na_2SO_4$) is used as a preparation reagent.
Figure 19B:
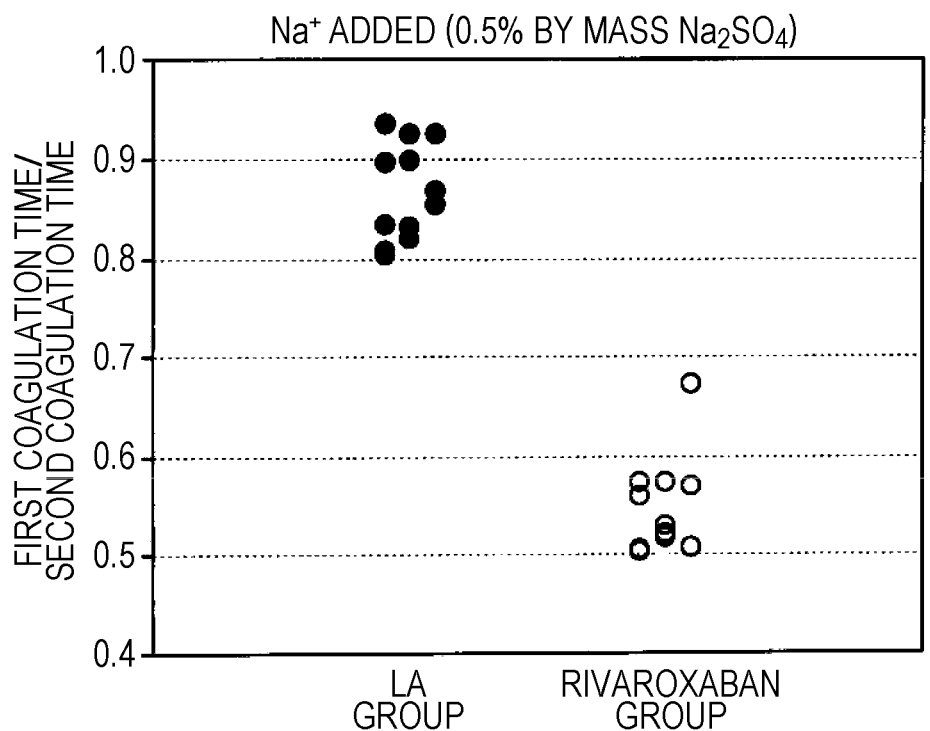
FIG. 19B is a diagram showing distributions of values of Ratio 3 in LA specimens and DAC specimens when a sodium ion ($Na_2SO_4$) is used as a preparation reagent.
Figure 19C:
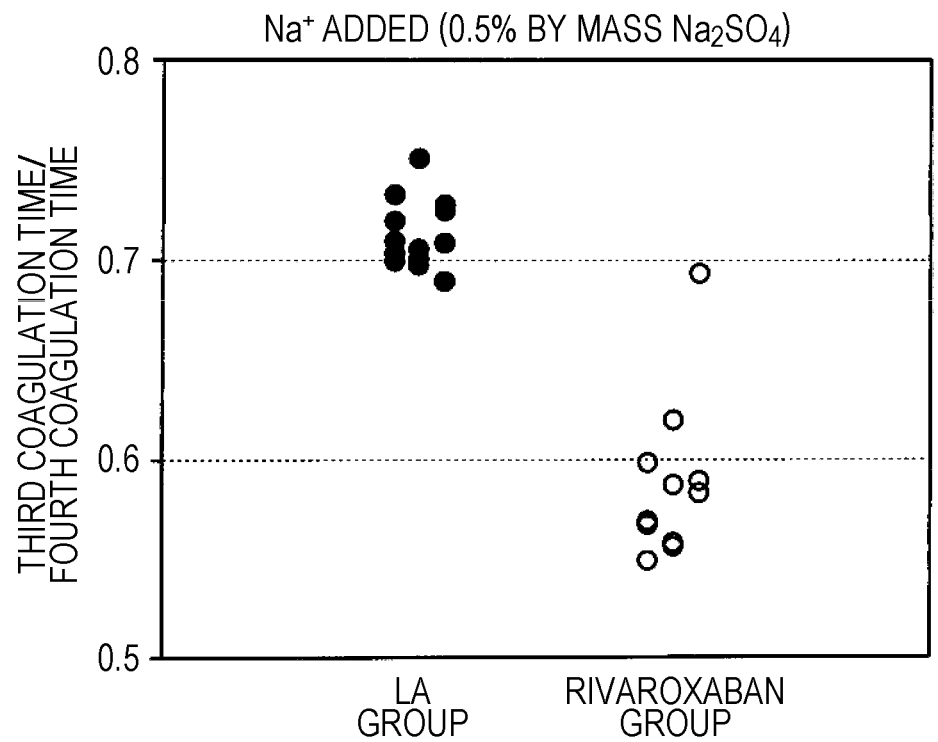
FIG. 19C is a diagram showing distributions of values of Ratio 4 in LA specimens and DAC specimens when a sodium ion ($Na_2SO_4$) is used as a preparation reagent.
Figure 19D:
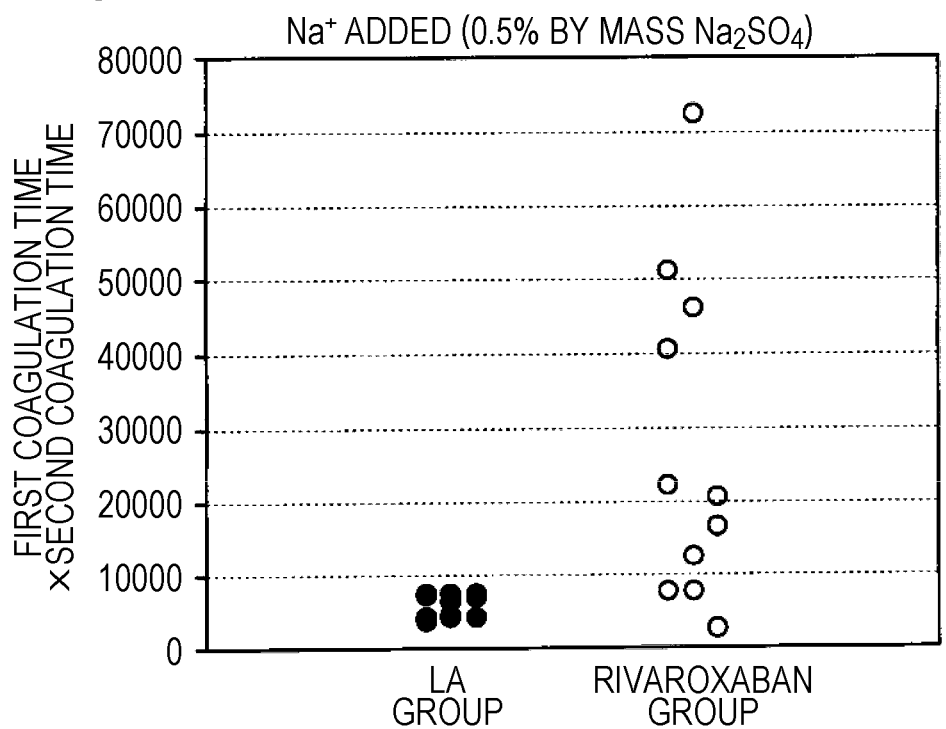
FIG. 19D is a diagram showing distributions of values of Product 1 in LA specimens and DAC specimens when a sodium ion ($Na_2SO_4$) is used as a preparation reagent.
Figure 19E:
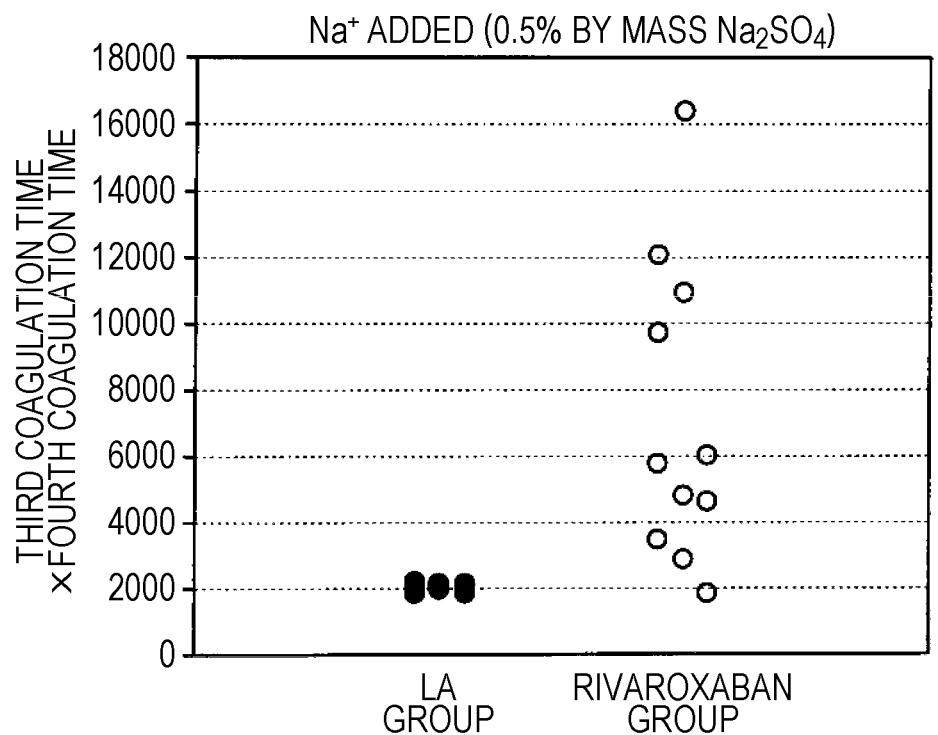
FIG. 19E is a diagram showing distributions of values of Product 2 in LA specimens and DAC specimens when a sodium ion ($Na_2SO_4$) is used as a preparation reagent.
Figure 19F:
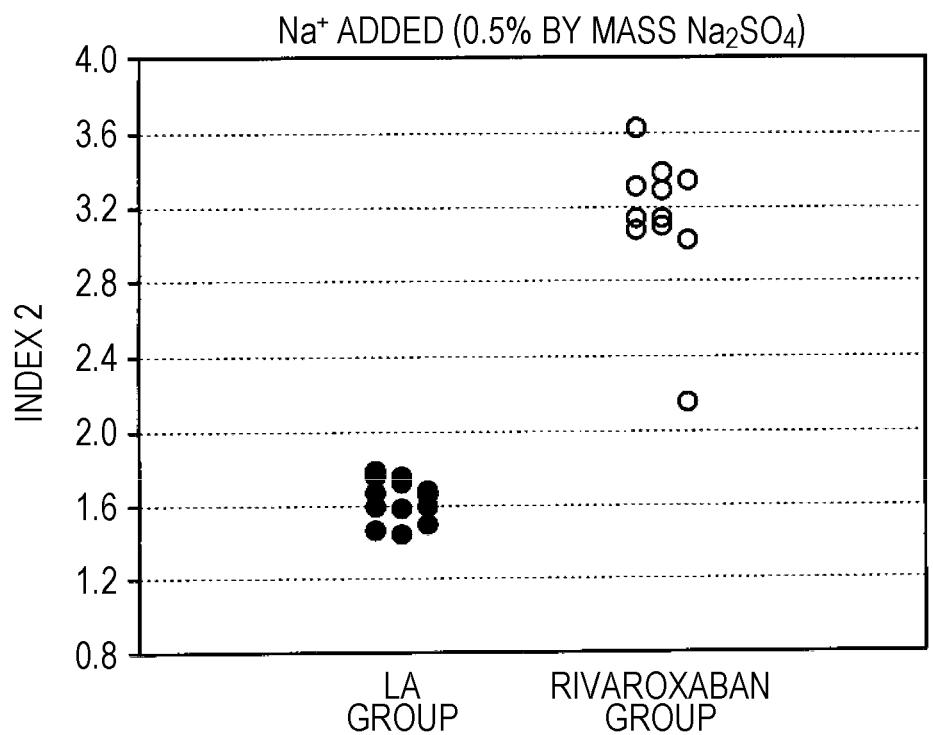
FIG. 19F is a diagram showing distributions of values of Index 2 in LA specimens and DAC specimens when a sodium ion ($Na_2SO_4$) is used as a preparation reagent.
Figure 20A:
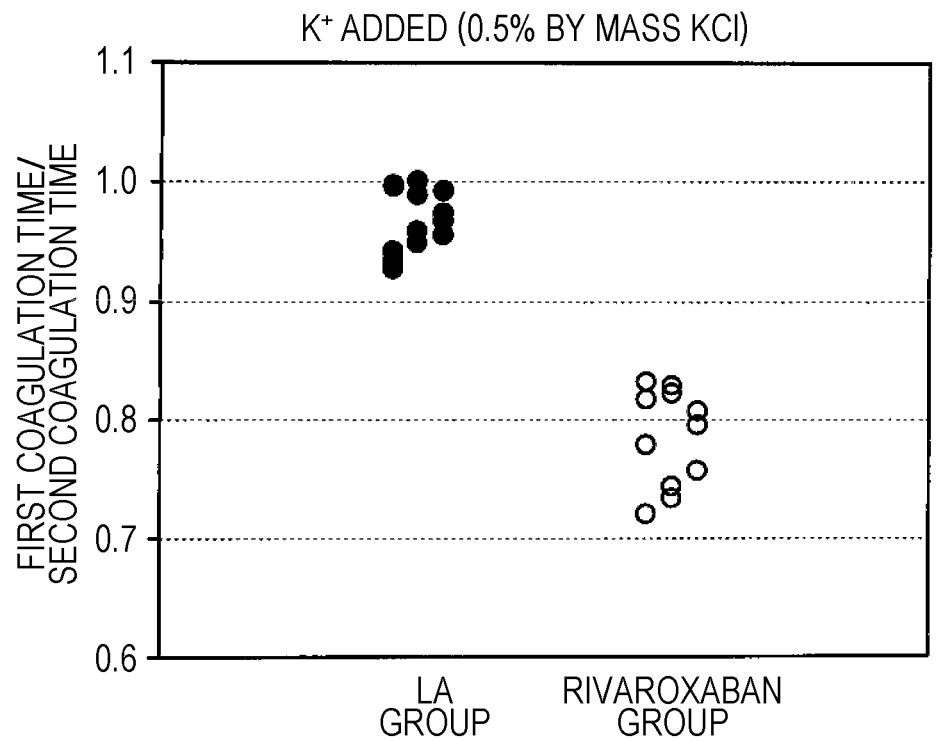
FIG. 20A is a diagram showing distributions of values of Ratio 3 in LA specimens and DAC specimens when a potassium ion is used as a preparation reagent.
Figure 20B:
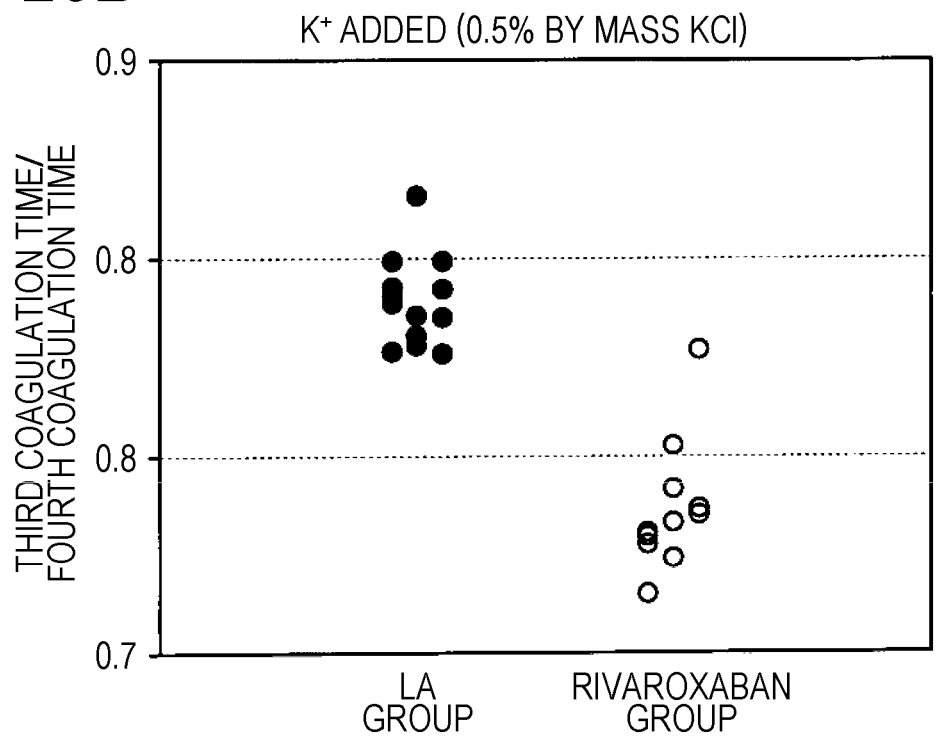
FIG. 20B is a diagram showing distributions of values of Ratio 4 in LA specimens and DAC specimens when a potassium ion is used as a preparation reagent.
Figure 20C:
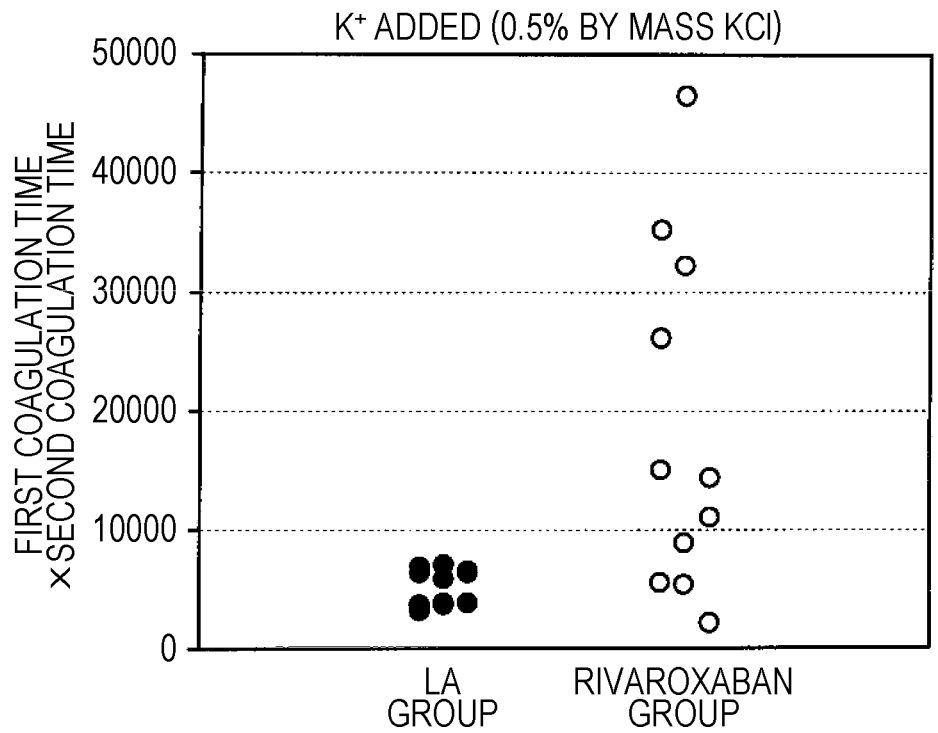
FIG. 20C is a diagram showing distributions of values of Product 1 in LA specimens and DAC specimens when a potassium ion is used as a preparation reagent.
Figure 20D:
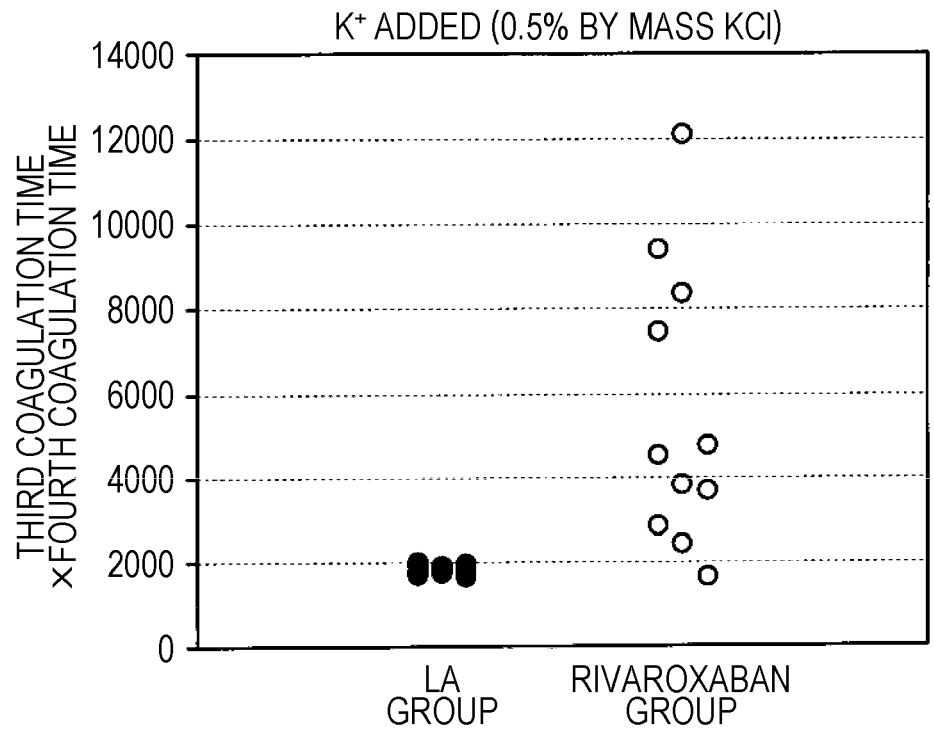
FIG. 20D is a diagram showing distributions of values of Product 2 in LA specimens and DAC specimens when a potassium ion is used as a preparation reagent.
Figure 20E:
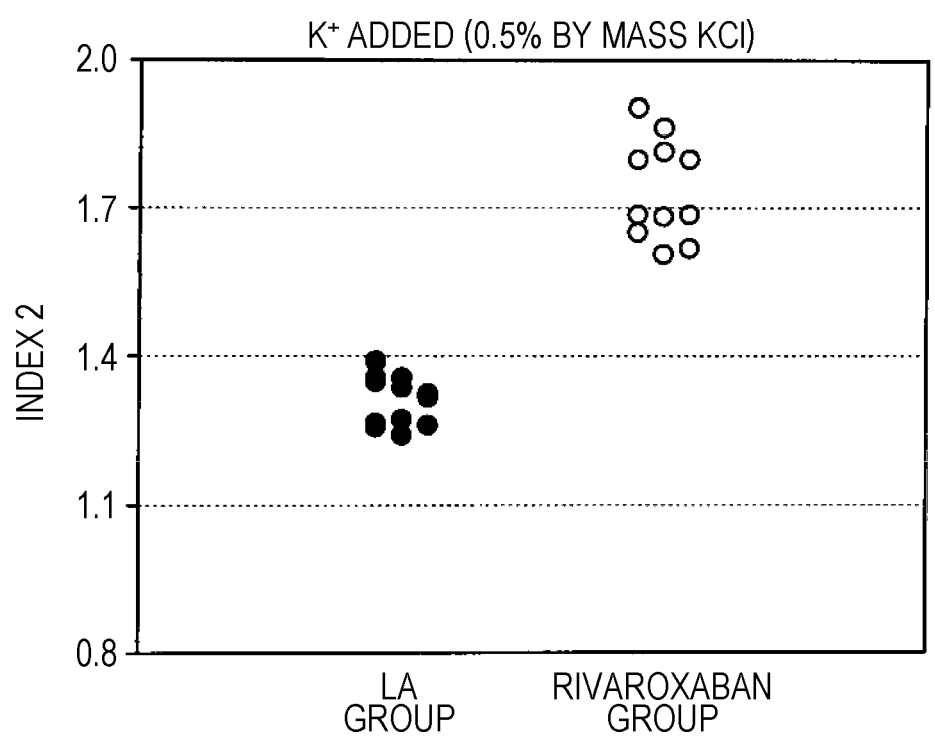
FIG. 20E is a diagram showing distributions of values of Index 2 in LA specimens and DAC specimens when a potassium ion is used as a preparation reagent.

Index 2 is the reciprocal of the product of Ratio 3 and Ratio 4. As shown in FIG. 11F, it can be seen that the LA group and the DAC group can be discriminated by Index 2. For Index 2, there was a significant difference between the LA group and the DAC group (p<0.1). Index 2 was shown to be a useful index for discrimination between blood specimens containing LA and blood specimens containing DAC.

Example 2

Using various metal ions as preparation reagents, whether discrimination between blood specimens containing LA and blood specimens containing DAC was possible was studied.

(1) Reagents and Specimens

In Example 2, the same coagulation time measurement reagent and blood specimen as in Example 1 were used. As a preparation reagent, an aqueous solution containing a metal ion was used. Each of nickel(II) chloride, cobalt(II) chloride, manganese chloride, zinc chloride, aluminum chloride and iron(III) chloride was dissolved in distilled water so that the metal ion concentration was 50 mmol/L.

(2) Measurement of Coagulation Time (2.1) Coagulation Times (First and Third Coagulation Times) of Measurement Samples not Containing Preparation Reagent The first and third coagulation times of each specimen were measured by CS-5100 (Sysmex Corporation) in the same manner as in Example 1.

(2.2) Coagulation Times (Second and Fourth Coagulation Times) of Measurement Samples Containing Preparation Reagent A preparation reagent containing a metal ion other than aluminum ion was mixed with each specimen (100 µL) so that the concentration of the added metal ion was 0.1, 0.25 and 0.5 mmol/L. A preparation reagent containing an aluminum ion was mixed with each specimen (100 µL) so that the concentration of the added aluminum ion was 0.1, 0.25, 0.5 and 1.0 mmol/L. The resulting mixture was warmed at 37° C. for about 4 minutes, then the first reagent (100 µL) was mixed, and the second coagulation time was measured. The fourth coagulation time was measured in the same manner as described above except that the second reagent was used in place of the first reagent. The coagulation time was measured with CS-5100 (Sysmex Corporation).

(3) Calculation of Parameters

From the coagulation times measured for each specimen, various parameters were acquired according to equations (A) to (G) of Example 1 and equation (H) below. For each parameter, a significant difference between the LA group and the DAC group was tested by t-test.

(Ratio 2)=(Second coagulation time)/(Fourth coagulation time)     Equation (H)

(4) Results

As an example of measurement results, the coagulation time and parameters when a zinc ion is used for some specimens are shown in Table 4. As an example of the distribution of each parameter, Ratio 2, Ratio 3, Ratio 4, Product 1, Product 2 and Index 2 in the LA group and the DAC group are shown in FIGS. 12A to 17F, respectively.

TABLE 4

| $Zn^{2+}$ (mM) | Parameter | LA-Containing plasma | | DAC-Containing plasma | |
|---|---|---|---|---|---|
| | | Control 1 Low | Control 2 High | Control Plasma 1 | Control Plasma 2 |
| 0 | First | 56.6 | 73.1 | 101.1 | 160.1 |
| 0.1 | Second | 62.5 | 85.1 | 106.5 | 163.1 |
| 0.25 | coagulation | 91.5 | 131.9 | 115.6 | 181.5 |
| 0.5 | time (sec.) | 139.0 | 169.3 | 153.9 | 226.1 |
| 0 | Third | 37.7 | 39.2 | 59.1 | 82.9 |
| 0.1 | Fourth | 39.6 | 41.6 | 60.9 | 84.0 |
| 0.25 | coagulation | 48.0 | 51.3 | 64.5 | 90.5 |
| 0.5 | time (sec.) | 64.4 | 67.5 | 73.5 | 105.6 |
| 0 | Ratio 1 | 1.50 | 1.86 | 1.73 | 1.93 |
| 0.1 | Ratio 2 | 1.58 | 2.05 | 1.75 | 1.94 |
| 0.25 | | 1.91 | 2.57 | 1.79 | 2.01 |
| 0.5 | | 2.16 | 2.51 | 2.09 | 2.14 |
| 0.1 | Ratio 3 | 0.91 | 0.86 | 0.95 | 0.98 |
| 0.25 | | 0.62 | 0.55 | 0.87 | 0.88 |
| 0.5 | | 0.41 | 0.43 | 0.66 | 0.71 |
| 0.1 | Ratio 4 | 0.95 | 0.94 | 0.97 | 0.99 |
| 0.25 | | 0.79 | 0.76 | 0.92 | 0.92 |
| 0.5 | | 0.59 | 0.58 | 0.80 | 0.79 |
| 0.1 | Product 1 | 3538 | 6221 | 10767 | 26112 |
| 0.25 | | 5179 | 9642 | 11687 | 29058 |
| 0.5 | | 7867 | 12376 | 15559 | 36199 |
| 0.1 | Product 2 | 1493 | 1631 | 3599 | 6964 |
| 0.25 | | 1810 | 2011 | 3812 | 7502 |
| 0.5 | | 2428 | 2646 | 4344 | 8754 |
| 0.1 | Index 1 | 1.05 | 1.10 | 1.01 | 1.01 |
| 0.25 | | 1.27 | 1.38 | 1.04 | 1.04 |
| 0.5 | | 1.44 | 1.35 | 1.21 | 1.11 |

TABLE 4-continued

| $Zn^{2+}$ | | LA-Containing plasma | | DAC-Containing plasma | |
|---|---|---|---|---|---|
| (mM) | Parameter | Control 1 Low | Control 2 High | Control Plasma 1 | Control Plasma 2 |
| 0.1 | Index 2 | 1.16 | 1.24 | 1.09 | 1.03 |
| 0.25 | | 2.06 | 2.36 | 1.25 | 1.24 |
| 0.5 | | 4.20 | 3.99 | 1.89 | 1.80 |

Although not shown, Ratio 1 and Index 1 could not discriminate between the LA group and the DAC group. In both the LA group and the DAC group, Ratio 1 was 1.3 or more, and Ratio 2 was 1.5 or more. In a blood specimen derived from a healthy subject, Ratio 1 and Ratio 2 are approximately 1.0, so that a specimen whose Ratio 1 is 1.3 or more or Ratio 2 is 1.5 or more can be selected as a determination target.

In Example 2, Ratio 3, Ratio 4, Product 1 and Product 2 are parameters calculated from the coagulation time of the test plasma and the coagulation time of the test plasma containing a metal ion measured using one kind of coagulation time measurement reagent. Ratio 2 and Index 2 are parameters calculated from the coagulation time of the test plasma and the coagulation time of the test plasma containing the alkali metal ion, which are measured using plural kinds of coagulation time measurement reagents with different phospholipid concentrations. Index 2 is the reciprocal of the product of Ratio 3 and Ratio 4. There was a significant difference between the LA group and the DAC group (p<0.1) for all Ratio 3, Ratio 4, Product 1, Product 2 and Index 2 regardless of which metal ion was used. The results using each metal ion will be described hereinbelow.

In the case of using a nickel ion, as shown in FIGS. 12A to 12E, it is likely that the LA group and the DAC group can be distinguished by Ratio 2, Ratio 3, Product 1, Product 2, and Index 2.

In the case of using a cobalt ion, as shown in FIGS. 13A to 13F, it is likely that the LA group and the DAC group can be distinguished by Ratio 2, Ratio 3, Ratio 4, Product 1, Product 2, and Index 2. In particular, it can be seen that Ratio 3, Ratio 4 and Index 2 can clearly divide the LA group and the DAC group.

In the case of using a manganese ion, as shown in FIGS. 14A to 14E, it is likely that the LA group and the DAC group can be distinguished by Ratio 3, Ratio 4, Product 1, Product 2, and Index 2.

In the case of using a zinc ion, as shown in FIGS. 15A to 15F, it is likely that the LA group and the DAC group can be distinguished by Ratio 2, Ratio 3, Ratio 4, Product 1, Product 2, and Index 2. In particular, it can be seen that Ratio 3, Ratio 4 and Index 2 can clearly divide the LA group and the DAC group.

In the case of using an aluminum ion, as shown in FIGS. 16A to 16F, it is likely that the LA group and the DAC group can be distinguished by Ratio 2, Ratio 3, Ratio 4, Product 1, Product 2, and Index 2. In particular, it can be seen that Ratio 3 and Index 2 can clearly divide the LA group and the DAC group.

In the case of using an iron ion, as shown in FIGS. 17A to 17F, it is likely that the LA group and the DAC group can be distinguished by Ratio 2, Ratio 3, Ratio 4, Product 1, Product 2, and Index 2.

From the above, in the case of using the above metal ion, Ratio 2, Ratio 3, Ratio 4, Product 1, Product 2 and Index 2 were shown to be useful indexes for discrimination between blood specimens containing LA and blood specimens containing DAC. From these results, it is suggested that the product of Ratio 3 and Ratio 4 and the product of Product 1 and Product 2 can also discriminate between the LA group and the DAC group.

Example 3

Using an alkali metal ion as a preparation reagent, whether discrimination between blood specimens containing LA and blood specimens containing DAC was possible was studied.

(1) Reagents and Specimens

In Example 3, the same coagulation time measurement reagent and blood specimen as in Example 1 were used. As a preparation reagent, an aqueous solution containing an alkali metal ion was used. The aqueous solution was prepared by dissolving sodium chloride, sodium sulfate and potassium chloride in distilled water, so that the concentrations were 3.4 mol/L (20% by mass), 1.4 mol/L (20% by mass), and 2.7 mol/L (20% by mass).

(2) Measurement of Coagulation Time (2.1) Coagulation Times (First and Third Coagulation Times) of Measurement Samples not Containing Preparation Reagent The first and third coagulation times of each specimen were measured by CS-5100 (Sysmex Corporation) in the same manner as in Example 1.

(2.2) Coagulation Times (Second and Fourth Coagulation Times) of Measurement Samples Containing Preparation Reagent A preparation reagent was mixed in each specimen (100 μL) so that the concentration was 0.5% by mass, and the mixture was warmed at 37° C. for about 4 minutes. In the mixture of the specimen and the preparation reagent, the concentration of the added metal ion is 85 mmol/L (sodium chloride), 70 mmol/L (sodium sulfate), and 67.5 mmol/L (potassium chloride). The first reagent (100 μL) was mixed to the resulting mixture. The second coagulation time was measured. The fourth coagulation time was measured in the same manner as described above except that the second reagent was used in place of the first reagent. The coagulation time was measured with CS-5100 (Sysmex Corporation).

(3) Calculation of Parameters

From the coagulation times measured for each specimen, various parameters were acquired in the same manner as in Example 2. For each parameter, a significant difference between the LA group and the DAC group was tested by t-test.

(4) Results

As an example of measurement results, the coagulation times when a sodium ion (sodium sulfate) is used for some specimens are shown in Table 5. As an example of the distribution of each parameter, Ratio 2, Ratio 3, Ratio 4, Product 1, Product 2 and Index 2 in the LA group and the DAC group are shown in FIGS. 18A to 20E, respectively.

TABLE 5

| | Sodium ion | |
|---|---|---|
| Blood specimen (Lot No.) | LA-Containing plasma (6246) | DAC-Containing plasma (44502-3) |
| First coagulation time (sec.) | 82.4 | 79.9 |
| Second coagulation time (sec.) | 89.0 | 154.2 |
| Third coagulation time (sec.) | 39.4 | 53.0 |
| Fourth coagulation time (sec.) | 52.5 | 90.3 |
| Ratio 1 | 2.1 | 1.5 |
| Ratio 2 | 1.7 | 1.7 |
| Ratio 3 | 0.9 | 0.5 |
| Ratio 4 | 0.8 | 0.6 |
| Product 1 | 7333 | 12320 |
| Product 2 | 2069 | 4786 |
| Index 1 | 0.809 | 1.133 |
| Index 2 | 1.243 | 2.227 |

Although not shown, Ratio 1 and Index 1 could not discriminate between the LA group and the DAC group. In both the LA group and the DAC group, Ratio 1 was 1.3 or more. In a blood specimen derived from a healthy subject, Ratio 1 is approximately 1.0, so that a specimen whose Ratio 1 is 1.3 or more can be selected as a determination target.

In Example 3, Ratio 3, Ratio 4, Product 1 and Product 2 are parameters calculated from the coagulation time of the test plasma and the coagulation time of the test plasma containing an alkali metal ion measured using one kind of coagulation time measurement reagent. Ratio 2 and Index 2 are parameters calculated from the coagulation time of the test plasma and the coagulation time of the test plasma containing the alkali metal ion, which are measured using plural kinds of coagulation time measurement reagents with different phospholipid concentrations. Index 2 is the reciprocal of the product of Ratio 3 and Ratio 4. There was a significant difference between the LA group and the DAC group (p<0.1) for all Ratio 3, Ratio 4, Product 1, Product 2 and Index 2 regardless of which metal ion was used. The results using each alkali metal ion will be described hereinbelow.

In the case of using a sodium ion derived from sodium chloride, as shown in FIGS. 18A to 18F, it is likely that the LA group and the DAC group can be distinguished by Ratio 2, Ratio 3, Ratio 4, Product 1, Product 2, and Index 2. In particular, it can be seen that Ratio 3 and Index 2 can clearly divide the LA group and the DAC group.

In the case of using a sodium ion derived from sodium sulfate, as shown in FIGS. 19A to 19F, it is likely that the LA group and the DAC group can be distinguished by Ratio 2, Ratio 3, Ratio 4, Product 1, Product 2, and Index 2. In particular, it can be seen that Ratio 3 and Index 2 can clearly divide the LA group and the DAC group.

In the case of using a potassium ion, as shown in FIGS. 20A to 20E, it is likely that the LA group and the DAC group can be distinguished by Ratio 3, Ratio 4, Product 1, Product 2, and Index 2. In particular, it can be seen that Ratio 3 and Index 2 can clearly divide the LA group and the DAC group.

From the above, in the case of using the above alkali metal ion, Ratio 2, Ratio 3, Ratio 4, Product 1, Product 2 and Index 2 were shown to be useful indexes for discrimination between blood specimens containing LA and blood specimens containing DAC. From these results, it is suggested that the product of Ratio 3 and Ratio 4 and the product of Product 1 and Product 2 can also discriminate between the LA group and the DAC group.

What is claimed is:

1. A method for determining whether a blood specimen contains a lupus anticoagulant, or contains a direct anticoagulant, said method comprising:
   preparing a first measurement sample, by mixing a blood specimen of a subject to be subjected to said determining with a first coagulation time measurement reagent, and measuring coagulation time to obtain a first coagulation time,
   preparing a second measurement sample, by mixing the blood specimen with a second coagulation time measurement reagent, and measuring coagulation time to obtain a second coagulation time, and
   acquiring a first value based on the first coagulation time and the second coagulation time, wherein said first value is selected from the group consisting of a product of the first coagulation time and the second coagulation time, and a ratio of the first coagulation time and the second coagulation time, and
   determining that said blood specimen contains a lupus anticoagulant, or contains a direct anticoagulant, based on the first value,
   wherein each of said first and second coagulation time measurement reagents comprises one or more coagulation-enhancing agents selected from the group consisting of activators, snake venom and tissue factors, and wherein each of said first and second coagulation time measurement reagents further comprises phospholipids,
   wherein each of said first and second coagulation time measurement reagents contains a preparation reagent containing a metal ion and/or normal plasma, and
   wherein the second coagulation time measurement reagent contains a higher concentration of phospholipids than the first coagulation time measurement reagent.

2. The method according to claim 1, wherein said determining comprises comparing the acquired first value with a threshold value corresponding to the acquired first value, and determining that said blood specimen contains a lupus anticoagulant, or contains a direct anticoagulant, based on the comparison.

3. The method according to claim 1, wherein each of said first and second coagulation time measurement reagents comprises at least one metal ion selected from the group consisting of a nickel ion, a cobalt ion, a manganese ion, a zinc ion, an aluminum ion, an iron ion, a sodium ion, and a potassium ion.

4. The method according to claim 1, wherein said first measurement sample is prepared by adding the preparation reagent to the blood specimen to prepare a mixture, and mixing the obtained mixture with the first coagulation time measurement reagent, and
   said second measurement sample is prepared by adding the preparation reagent to the blood specimen to prepare a mixture, and mixing the obtained mixture with the second coagulation time measurement reagent.

5. The method according to claim 1, wherein the metal ion is at least one selected from the group consisting of a nickel ion, a cobalt ion, a manganese ion, a zinc ion, an aluminum ion and an iron ion, and the concentration of the added metal ion in the mixture is between 0.001 mmol/L and 100 mmol/L.

6. The method according to claim 1, wherein the metal ion is at least one selected from the group consisting of a sodium ion and a potassium ion, and in the mixture, the concentration of the added metal ion is between 0.1 mmol/L and 5 mol/L.

7. The method according to claim 1, wherein each of said first and second coagulation time measurement reagents contains normal plasma.

8. The method according to claim 7, wherein said preparation reagent comprises normal plasma, and wherein
each of said first and second measurement samples is prepared by mixing the blood specimen and the preparation reagent in a volume ratio of 1:1, and mixing the obtained mixture with each of said first and second coagulation time measurement reagents.

9. The method according to claim 1, wherein the acquired first value is generated without using a coagulation time of normal plasma.

10. The method according to claim 1, further comprising preparing a third measurement sample, by mixing the blood specimen with a third coagulation time measurement reagent, and measuring coagulation time to obtain a third coagulation time,
preparing a fourth measurement sample, by mixing the blood specimen with a fourth coagulation time measurement reagent, and measuring coagulation time to obtain a fourth coagulation time, and
acquiring a second value based on the third coagulation time and the fourth coagulation time, wherein said second value is selected from the group consisting of a product of the third coagulation time and the fourth coagulation time, and a ratio of the third coagulation time and the fourth coagulation time,
wherein each of said third and fourth coagulation time measurement reagents comprises one or more coagulation-enhancing agents selected from the group consisting of activators, snake venom and tissue factors, and wherein each of said third and fourth coagulation time measurement reagents further comprises phospholipids,
and wherein the third coagulation time measurement reagent contains a higher concentration of phospholipids than the fourth coagulation time measurement reagent.

11. The method according to claim 10, wherein said determining comprises determining that said blood specimen contains a lupus anticoagulant, or contains a direct anticoagulant, based on the acquired first and second values.

12. The method according to claim 11, wherein said determining comprises comparing the value of an index calculated by equation (4) or (5) below with a threshold value corresponding to the index, and determining that said blood specimen contains a lupus anticoagulant, or contains a direct anticoagulant, based on the comparison result, $$(\text{Index}) = [(\text{Second coagulation time})/(\text{First coagulation time})] \times [(\text{Fourth coagulation time})/(\text{Third coagulation time})] \quad \text{Equation (4) or}$$

$$(\text{Index}) = [(\text{First coagulation time})/(\text{Second coagulation time})] \times [(\text{Third coagulation time})/(\text{Fourth coagulation time})] \quad \text{Equation (5).}$$

* * * * *